(12) United States Patent
Verner et al.

(10) Patent No.: US 7,517,988 B2
(45) Date of Patent: Apr. 14, 2009

(54) HYDROXAMATES AS THERAPEUTIC AGENTS

(75) Inventors: Erik J. Verner, Belmont, CA (US); Hon C. Hui, San Mateo, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 0 days.

(21) Appl. No.: 11/940,273

(22) Filed: Nov. 14, 2007

(65) Prior Publication Data

US 2008/0255221 A1  Oct. 16, 2008

Related U.S. Application Data

(62) Division of application No. 11/834,558, filed on Aug. 6, 2007, now Pat. No. 7,420,089, which is a division of application No. 10/818,755, filed on Apr. 6, 2004, now Pat. No. 7,276,612.

(60) Provisional application No. 60/641,286, filed on Apr. 7, 2003, provisional application No. 60/464,448, filed on Apr. 21, 2003.

(51) Int. Cl.
*C07D 215/38* (2006.01)
*A61K 31/53* (2006.01)

(52) U.S. Cl. ............ 546/169; 546/146; 544/235; 544/236; 544/283; 544/349; 514/243; 514/246; 514/249; 514/258.1; 514/299

(58) Field of Classification Search ............ 546/146, 546/169; 544/235, 236, 283, 349; 514/243, 514/246, 249, 258.1, 299

See application file for complete search history.

(56) References Cited

U.S. PATENT DOCUMENTS

| | | | |
|---|---|---|---|
| 4,999,378 | A | 3/1991 | Fujii et al. |
| 5,972,978 | A | 10/1999 | Andersen et al. |
| 6,211,197 | B1 | 4/2001 | Belley et al. |
| 6,960,685 | B2 | 11/2005 | Watkins et al. |
| 7,276,612 | B2 | 10/2007 | Verner et al. |
| 2004/0053908 | A1 | 3/2004 | Funahashi et al. |
| 2004/0077726 | A1 | 4/2004 | Watkins et al. |
| 2007/0293540 | A1 | 12/2007 | Verner et al. |
| 2008/0004331 | A1 | 1/2008 | Verner et al. |

FOREIGN PATENT DOCUMENTS

| | | |
|---|---|---|
| EP | 0084236 A2 | 7/1983 |
| EP | 0394440 A1 | 10/1990 |
| JP | 3-215470 * | 9/1991 |
| WO | WO-95-05358 A1 | 2/1995 |
| WO | WO-00-20371 A1 | 4/2000 |
| WO | WO-01-14331 A2 | 3/2001 |
| WO | WO-01-38322 A1 | 5/2001 |
| WO | WO-03-013493 A1 | 2/2002 |
| WO | WO-02-26703 A1 | 4/2002 |
| WO | WO-02-30879 A2 | 4/2002 |
| WO | WO-03-070691 A1 | 8/2003 |
| WO | WO-2004-013130 A1 | 2/2004 |

OTHER PUBLICATIONS

U.S. Appl. No. 11/940,260, filed Nov. 14, 2007, Verner et al.
Brzozowski, Z. et al., "Derivatives of 2-Mercapobenzenesulphonamide XI. Synthesis and Some Pharmacological Properties of 2-{2—[2-(3,4,5-Trimethoxybenzamido)Ethylthio]Benzenesulphonyl} Guanadines," Acta Poloniae Pharmaceutica-Drug Research 50(4-5):345-352 (1993).
Carter et al., Chemotherapy of Cancer, 2nd ed., John Wiley & Sons, N.Y., N.Y. 1981, pp. 362-365.
Hines, J.W. and Stammer, C.H., "3-Hydroxyisoxazole-5-hydroxamic Acid," J. Med. Chem 20(7):965-967 (1977).
LaVoie, R., "Design and Synthesis of a Novel Class of Histone Deacetylase Inhibitors," Bioorg. Med. Chem. Ltrs. 11:2847-2850 (2001).
Uesato, S., "Novel Histone Deacetylase Inhibitors: N-Hydroxycarboxamides Possessing a Terminal Bicyclic Aryl Group," Bioorg. Med. Chem. Ltrs. 12:1347-1349 (2002).
Watanabe, S. et al., "Synthesis of 4-[1-(substituted phenyl)-2-oxopyrrolidin4-yl]methyloxybenzoic acids and related compounds, and their inhibitory capacities toward fatty-acid and sterol biosynthesis," Eur. J. Med. Chem. 29:675-686 (1994).

* cited by examiner

*Primary Examiner*—Shailendra Kumar
(74) *Attorney, Agent, or Firm*—Wilson Sonsini Goodrich & Rosati

(57) ABSTRACT

The present invention is directed to certain hydroxamate derivatives that are useful in the treatment of hepatitis C. These compounds are also inhibitors of histone deacetylase and are therefore useful in the treatment of diseases associated with histone deacetylase activity. Pharmaceutical compositions and processes for preparing these compounds are also disclosed.

15 Claims, No Drawings

HYDROXAMATES AS THERAPEUTIC AGENTS

CROSS-REFERENCE

This application is a divisional patent application of U.S. patent application Ser. No. 11/834,558, filed Aug. 6, 2007, now U.S. Pat. No. 7,420,089 which is a divisional patent application of U.S. patent application Ser. No. 10/818,755, now issued U.S. Pat. No. 7,276,612 which claims priority to U.S. Provisional Application Ser. Nos. 60/461,286 and 60/464,448, filed on Apr. 7, 2003, and April 21, 2003, respectively. The disclosures of the above cited patent and these applications are incorporated herein by reference in their entirety.

BACKGROUND OF THE INVENTION

1. Field of the Invention

The present invention is directed to certain hydroxamate derivatives that are useful in the treatment of hepatitis C. These compounds are also inhibitors of histone deacetylase and are therefore useful in the treatment of diseases associated with histone deacetylase activity. Pharmaceutical compositions and processes for preparing these compounds are also disclosed.

2. State of the Art

Hepatitis C:

Chronic hepatitis C is a slowly progressive disease having a significant impact on morbidity and mortality. While many patients who contract hepatitis C will have sub clinical or mild disease, at least 80% of the individuals who contract HCV develop chronic infection and hepatitis. Twenty to fifty percent of these eventually progress to cirrhosis and 1-2% develop liver cancer (Hoofnagle, J. H.; 1997; *Hepatology* 26: 15S-20S). There are an estimated 170 million HCV carriers world-wide, and HCV-associated end-stage liver disease is now one of the leading cause of liver transplantation. In the United States alone, hepatitis C is responsible for 8,000 to 10,000 deaths annually.

At the present time, interferon-α2b/ribavirin combination therapy is the only available treatment. Sustained virologic response to IFN-α2b-ribavirin combination therapy occurs in about 40-45% of those treated. For those patients who fail interferon-α2b/ribavirin combination therapy, there is currently no alternative to prevent the progression of liver disease. Thus, a need exists for alternative therapies for the treatment of chronic HCV infection. The present invention fulfills this need.

Histone Deacetylases:

Interest in histone deacetylase enzymes (HDACs) as targets for pharmaceutical development has centered on the role of HDACs in regulating genes associated with cell-cycle progression and the development and progression of cancer (reviewed in Kramer et. al. 2001. *Trends Endocrinol. Metab.* 12:294-300). Several studies have shown that treatment of various cell lines with HDAC inhibitors leads to hyper acetylation of histone proteins and cell-cycle arrest in late $G_1$ phase or at the $G_2$/M transition. Genes involved in the cell cycle that have been shown to be up regulated by HDAC inhibitors include p21, p27, p53 and cyclin E. Cyclin A and cyclin D have been reported to be down regulated by HDAC inhibitors. In tumor cell lines, several studies have shown that treatment with HDAC inhibitors can lead to growth inhibition, growth arrest, terminal differentiation and/or apoptosis. In vivo studies have demonstrated growth inhibition of tumors and a reduction in tumor metastasis as a result of treatment with HDAC inhibitors.

The clearest link between abnormal HDAC activity and cancer occurs in acute promyelocytic leukemia. In this condition, a chromosomal translocation leads to the fusion of the retinoic acid receptor RARα with the promyelocytic leukemia (PML) or promyelocytic leukemia zinc-finger (PLZF) proteins. Both PML-RARα and PLZF-RARα promote the progression of leukemia by repressing retinoic acid-regulated genes through the abnormal recruitment of SMRT-mSin3-HDAC complex (Lin et. al., 1998, *Nature* 391:811-814; Grignani et al., 1998, *Nature* 391:815-818). Whereas the PML-RARα form of the disease is treatable with retinoic acid, the PLZF-RARα form is resistant to this treatment. For a patient with the retinoic acid-resistant form of the disease, the addition of the HDAC inhibitor sodium butyrate to the dosing regimen led to complete clinical and cytogenic remission (Warrell et al., 1998, *J. Natl. Cancer. Inst.* 90:1621-1625). HDACs have also been associated with Huntington's disease (Steffan, et al., *Nature* 413:739-744, "Histone deacetylase inhibitors arrest polyglutamine-dependent neurodegeneration in Drosophila").

In summary, an increase in HDAC activity contributes to the pathology and/or symptomatology of a number of diseases. Accordingly, molecules that inhibit the activity of HDAC are useful as therapeutic agents in the treatment of such diseases.

SUMMARY OF THE INVENTION

In a first aspect, this invention provides a compound of Formula (I):

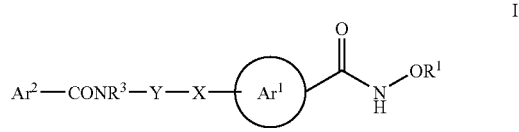

wherein:

$R^1$ is hydrogen or alkyl;

X is —O—, —$NR^2$—, or —S(O)ₙ, where n is 0-2 and $R^2$ is hydrogen or alkyl;

Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;

$Ar^1$ is phenylene or heteroarylene wherein said $Ar^1$ is optionally substituted with one or two groups independently selected from alkyl, halo, hydroxy, alkoxy, haloalkoxy, or haloalkyl;

$R^3$ is hydrogen, alkyl, hydroxyalkyl, or optionally substituted phenyl; and $Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl; or a pharmaceutically acceptable salt thereof.

In a second aspect, this invention is directed to a pharmaceutical composition comprising a therapeutically effective amount of a compound of Formula (I) or pharmaceutically acceptable salts thereof and a pharmaceutically acceptable excipient.

In a third aspect, this invention is directed to a method for treating a disease in an animal mediated by HDAC which method comprises administering to the animal a pharmaceutical composition comprising a therapeutically effective amount of a compound of Formula (I) or a pharmaceutically acceptable salt thereof and a pharmaceutically acceptable excipient. Preferably, the disease is a proliferative disorder such as cancer and bipolar disorders and the animal is a human. Preferably, the cancer is prostate cancer, breast cancer, lung melanoma, stomach cancer, neuroblastoma, colon cancer, pancreatic cancer, ovarian cancer, T-cell lymphoma, or leukemia such as myelogenous leukemia (MM) and acute myelogenous leukemia (AML).

In a fourth aspect, this invention is directed to a method for treating cancer in an animal which method comprises administering to the animal a pharmaceutical composition comprising a therapeutically effective amount of a compound of Formula (I) or a pharmaceutically acceptable salt thereof and a pharmaceutically acceptable excipient in combination with radiation therapy and optionally in combination with one or more compound(s) independently selected from an estrogen receptor modulator, an androgen receptor modulator, a retinoid receptor modulator, a cytotoxic agent, another antiproliferative agent, a prenyl-protein transferase inhibitor, an HMG-CoA reductase inhibitor, an HIV protease inhibitor, a reverse transcriptase inhibitor, an angiogenesis inhibitor, or a DNA methyl transferase inhibitor.

Applicants have also discovered that the compounds of the present invention are useful in the treatment of hepatitis C. Accordingly, in a fifth aspect, this invention is directed to a method of treating hepatitis C in an animal comprising administering the animal a pharmaceutical composition comprising a therapeutically effective amount of a compound of Formula (I) or a pharmaceutically acceptable salt thereof and a pharmaceutically acceptable excipient optionally in combination with one or more other hepatitis C agent. Preferably, the hepatitis C agents are interferon-α2b, ribavirin, and hcv polymerase inhibitors.

In a sixth aspect, this invention is direct to an intermediate of Formula (II):

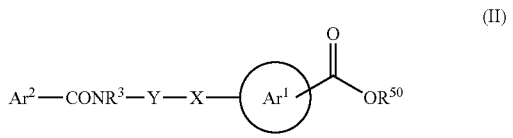

where $R^{50}$ is hydrogen or alkyl and $Ar^1$, $Ar^2$, $R^3$, X and Y are as defined for compounds of Formula (I) above; or a salt thereof. Preferably, $Ar^1$, $Ar^2$, $R^3$, X and Y are as defined in Preferred embodiments below.

In a seventh aspect, this invention is directed to a process of preparing a compound of Formula (I) comprising:

(i) reacting a compound of Formula (III):

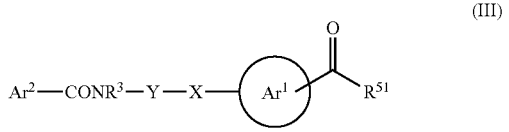

were $R^{51}$ is hydroxy, alkoxy, halo, or succinimido ester with a hydroxylamine of formula $NH_2OR''$ where R'' is hydrogen, alkyl, or an oxygen protecting group; or (ii) treating a compound of Formula (IV):

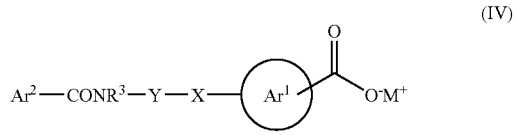

where $M^+$ is an alkali metal with an acid; followed by treatment with $NH_2OR''$ where R'' is hydrogen, alkyl, or an oxygen protecting group;

to give a compound of Formula (V):

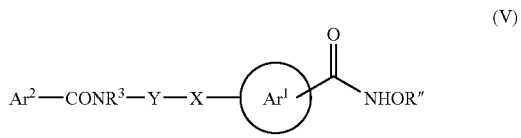

(iii) optionally removing R'' group in compound (V) to give a compound of Formula (I) where $R^1$ is hydrogen;

(iv) optionally forming an acid addition salt of the product formed in Step (i), (ii), or (iii) above;

(v) optionally forming free base of the product formed in Step (i), (ii), (iii), or (iv) above; or (vi) optionally modifying any of the X, Y, $R^1$, $R^2$, $R^3$, $Ar^1$ and $Ar^2$ groups in the product formed in Step (i), (ii), (iii), (iv), or (v) above.

In a eighth aspect, this invention is directed to the use of a compound of Formula (I) or a pharmaceutically acceptable salt thereof in the manufacture of a medicament for the treatment of cancer.

In a ninth aspect, this invention is directed to the use of a compound of Formula (I) or (II) or a pharmaceutically acceptable salt thereof in the manufacture of a medicament for the treatment of hepatitis C.

DETAILED DESCRIPTION OF THE INVENTION

Definitions:

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenylene" means a linear divalent hydrocarbon radical of two to six carbon atoms or a branched monovalent hydrocarbon radical of three to six carbon atoms containing one or two double bonds, e.g., ethenylene, propenylene, 2-propenylene, butenylene (including all isomeric forms), and the like.

"Alkylthio" means a —SR radical where R is alkyl as defined above, e.g., methylthio, ethylthio, propylthio (including all isomeric forms), butylthio (including all isomeric forms), and the like.

"Alkylsulfinyl" means a —S(O)R radical where R is alkyl as defined above, e.g., methylsulfinyl, ethylsulfinyl, propylsulfinyl (including all isomeric forms), and the like.

"Alkylsulfonyl" means a —SO$_2$R radical where R is alkyl as defined above, e.g., methylsulfonyl, ethylsulfonyl, and the like.

"Amino" means a —NH$_2$; or an N-oxide derivative or a protected derivative thereof e.g., —NH→O, —NHBoc, —NHCbz, and the like. Preferably, —NH$_2$.

"Alkylamino" means a —NHR radical where R is alkyl as defined above; or an N-oxide derivative, or a protected derivative thereof, e.g., methylamino, ethylamino, n-, iso-propylamino, n-, iso-, tert-butylamino, methylamino-N-oxide, —N(Boc)CH$_3$, and the like.

"Alkoxy" means a —OR radical where R is alkyl as defined above, e.g., methoxy, ethoxy, propoxy, or 2-propoxy, n-, iso-, or tert-butoxy, and the like.

"Alkoxycarbonyl" means a —C(O)OR radical where R is alkyl as defined above, e.g., methoxycarbonyl, ethoxycarbonyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" means a —OR radical where R is alkoxyalkyl as defined above, e.g., methoxyethoxy, 2-ethoxyethoxy, and the like.

"Alkoxyalkyloxyalkyl" means a -(alkylene)-R radical where R is alkoxyalkyloxy as defined above, e.g., methoxyethoxymethyl, 2-ethoxyethoxymethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, and R' is selected from hydrogen, alkyl, hydroxyalkyl, alkoxyalkyl, optionally substituted phenyl, optionally substituted phenylalkyl, optionally substituted heteroaryl, optionally substituted heteroaralkyl, or haloalkyl; or an N-oxide derivative or a protected derivative thereof. Preferably, R and R' are independently selected from hydrogen, alkyl, or —COR$^a$ where R$^a$ is alkyl; or an N-oxide derivative, or a protected derivative e.g., aminomethyl, methylaminoethyl, 2-ethylamino-2-methylethyl, 1,3-diaminopropyl, dimethylaminomethyl, diethylaminoethyl, acetylaminopropyl, aminomethyl-N-oxide, and the like.

"Aminoalkoxy" means a —OR radical where R is aminoalkyl as defined above, e.g., 2-aminoethoxy, 2-dimethylaminopropoxy, and the like.

"Aminocarbonyl" means a —CONRR radical where each R is independently hydrogen or alkyl as defined above, e.g., —CONH$_2$, methylaminocarbonyl, 2-dimethylaminocarbonyl, and the like.

"Acylamino" means a —NHCOR radical where R is alkyl as defined above, e.g., acetylamino, propionylamino, and the like.

"Aryl" means a monovalent monocyclic or bicyclic aromatic hydrocarbon radical of 6 to 12 ring atoms e.g., phenyl, naphthyl or anthracenyl. Unless stated otherwise, the aryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted phenylalkyl, optionally substituted heteroaryl, cycloalkyloxy, cycloalkenyloxy, optionally substituted phenylcarbonylamino, optionally substituted heteroaryloxy, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—R$^a$ (where n is 0 to 2 and R$^a$ is alkyl, haloalkyl, hydroxyalkyl, alkoxyalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, optionally substituted heteroaralkyl, or optionally substituted heterocycloalkyl), -alkylene-NHCO—R$^c$ (where R$^c$ is alkyl, haloalkyl, optionally substituted phenyl, optionally substituted phenylalkyl, optionally substituted heteroaryl, optionally substituted heteroaralkyl, or optionally substituted heterocycloalkyl), or -(alkylene)n1-CONR$^d$R$^e$ (where n1 is 0 or 1, R$^d$ and R$^e$ are independently, hydrogen, alkyl, haloalkyl, hydroxyalkyl, alkoxyalkyl, aminoalkyl, optionally substituted phenyl, optionally substituted phenylalkyl, optionally substituted heteroaryl, optionally substituted heteroaralkyl, or optionally substituted heterocycloalkylalkyl, or R$^d$ and R$^e$ together with the nitrogen atom to which they are attached form heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. Preferably, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)-ethoxy, methoxymethyl, phenoxymethyl, 2-morpholino-4-ylethyl, morpholino-4-ylmethyl, N,N-dimethylaminomethyl, i-propoxymethyl, or phenoxymethyl.

"Aralkyl" means a -(alkylene)-R radical where R is aryl as defined above.

"Aralkenyl" means a -(alkenylene)-R radical where R is aryl as defined above.

"Cycloalkyl" means a cyclic saturated monovalent hydrocarbon radical of three to ten carbon atoms, e.g., cyclopropyl, cyclobutyl, cyclopentyl, cyclohexyl, or adamantyl. The cycloalkyl is optionally substituted with optionally substituted phenyl.

"Cycloalkenyl" means a cyclic unsaturated monovalent hydrocarbon radical of three to six carbon atoms, e.g., cyclopropenyl, cyclobutenyl, cyclohexenyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Cycloalkyloxy" means a —OR radical where R is cycloalkyl as defined above, e.g., cyclopropyloxy, cyclohexyloxy, and the like.

"Cycloalkenyloxy" means a —OR radical where R is cycloalkenyl as defined above, e.g., cyclopropenyloxy, cyclohexenyloxy, and the like.

"Dialkylamino" means a —NRR' radical where R and R' are independently alkyl as defined above, e.g., dimethylamino, diethylamino, methylpropylamino, methylethylamino, n-, iso-, or tert-butylamino, and the like.

"Halo" means fluoro, chloro, bromo, and iodo, preferably fluoro or chloro.

"Haloalkyl" means alkyl substituted with one or more halogen atoms, preferably one to five halogen atoms, preferably fluorine or chlorine, including those substituted with different halogens, e.g., —CH$_2$Cl, —CF$_3$, —CHF$_2$, —CF$_2$CF$_3$, —CF(CH$_3$)$_3$, and the like.

"Haloalkoxy" means a —R radical where R is haloalkyl as defined above e.g., —OCF$_3$, —OCHF$_2$, and the like.

"Haloalkoxyalkyl" means a -(alkylene)-OR radical where R is haloalkyl as defined above e.g., trifluoromethyloxymethyl, 2,2,2-trifluoroethyloxymethyl, 2-trifluoromethoxyethyl, and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" or "hydroxyalkyloxy" means a OR radical where R is hydroxyalkyl as defined above.

"Hydroxyalkoxyalkyl" or "hydroxyalkyloxyalkyl" means a -(alkylene)-OR radical where R is hydroxyalkyl as defined above e.g., hydroxymethyloxymethyl, hydroxyethyloxymethyl, and the like.

"Heterocycloalkyl" means a saturated or unsaturated monovalent cyclic group of 3 to 8 ring atoms in which one or two ring atoms are heteroatom selected from N, O, or S(O)$_n$, where n is an integer from 0 to 2, the remaining ring atoms being C. One or two ring carbon atoms can optionally be replaced by a —CO— group. More specifically the term heterocycloalkyl includes, but is not limited to, pyrrolidino, piperidino, morpholino, piperazino, tetrahydropyranyl, tetrahydroquinolinyl and thiomorpholino, and the derivatives thereof (formed when the heterocycloalkyl ring is substituted with a substituent listed below); and an N-oxide or a protected derivative thereof. The heterocycloalkyl is optionally fused to aryl. Unless stated otherwise, the heterocyloalkyl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted phenylalkyl, cycloalkyloxy, cycloalkenyloxy, optionally substituted phenylcarbonylamino, optionally substituted heteroaryl, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—R$^a$ (where n is 0 to 2 and R$^a$ is alkyl, haloalkyl, hydroxyalkyl, alkoxyalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, or optionally substituted heteroaralkyl), -alkylene-NHCO—R$^c$ (where R$^c$ is alkyl, haloalkyl, optionally substituted phenyl, optionally substituted phenylalkyl, optionally substituted heteroaryl, or optionally substituted heteroaralkyl), or -(alkylene)n1-CONR$^d$R$^e$ (where n1 is 0 or 1, R$^d$ and R$^e$ are independently, hydrogen, alkyl, haloalkyl, hydroxyalkyl, alkoxyalkyl, aminoalkyl, optionally substituted phenyl, optionally substituted phenylalkyl, optionally substituted heteroaryl, optionally substituted heteroaralkyl, or optionally substituted heterocycloalkylalkyl, or R$^d$ and R$^e$ together with the nitrogen atom to which they are attached form heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. Preferably, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl.

"Heterocycloalkylalkyl" means a -(alkylene)-R radical where R is heterocycloalkyl ring as defined above e.g., furanylmethyl, piperazinylmethyl, morpholinylethyl, and the like.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. More specifically the term heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isoxazolyl, benzoxazolyl, benzothiophenyl, benzthiazolyl, quinolinyl, isoquinolinyl, benzofuranyl, benzopyranyl, and thiazolyl, and the derivatives thereof (formed when the heterocyloalkyl ring is substituted with a substituent listed below); or an N-oxide or a protected derivative thereof. Unless stated otherwise, the heteroaryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, cycloalkyloxy, cycloalkenyloxy, optionally substituted phenylcarbonylamino, optionally substituted heteroaryl, optionally substituted heteroaryloxy, optionally substituted heteroaralkyloxy, aminoalkyl, aminoalkoxy, alkoxyalkyl, alkoxyalkyloxy, methylenedioxy, haloalkoxyalkyl, optionally substituted phenylalkyl, optionally substituted phenyloxy, optionally substituted phenylalkyloxy, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—R$^a$ (where n is 0 to 2 and R$^a$ is alkyl, hydroxyalkyl, haloalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, optionally substituted heteroaralkyl, or optionally substituted heterocycloalkyl), -alkylene-NHCO—R$^c$ (where R$^c$ is alkyl, haloalkyl, hydroxyl, optionally substituted phenyl, optionally substituted phenylalkyl, optionally substituted heteroaryl, optionally substituted heteroaralkyl, or optionally substituted heterocycloalkyl), -(alkylene)n1-CONR$^d$R$^f$ (where n1 is 0 or 1, R$^d$ is hydrogen or alkyl, and R$^f$ is hydrogen, alkyl, hydroxylalkyl, alkoxyalkyl, optionally substituted phenyl, optionally substituted phenylalkyl, optionally substituted heteroaryl, optionally substituted heteroaralkyl, or optionally substituted heterocycloalkylalkyl, or R$^d$ and R$^f$ together with the nitrogen atom to which they are attached form heterocycloalkyl), -alkylene-NR$^e$-alkyleneCONR$^c$R$^d$ (where R$^c$ is as defined above and R$^d$ and R$^e$ are independently hydrogen or alkyl), or carboxyalkylaminoalkyl wherein the alkyl chain in haloalkoxyalkyl, optionally substituted phenyloxyalkyl, optionally substituted heteroaryloxyalkyl, or aminoalkyl is optionally substituted with one or two fluoro. Preferably, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl.

When the heteroaryl ring is divalent it has been referred to as heteroarylene in this application.

"Heteroarylamino" means a NHR radical where R is heteroaryl as defined above.

"Heteroaralkyl" means a -(alkylene)-R radical where R is heteroaryl as defined above.

"Heteroaralkenyl" means a -(alkenylene)-R radical where R is heteroaryl as defined above.

"Methylenedioxy" means —O—CH$_2$—O—.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this invention.

The present invention also includes N-oxide derivatives and protected derivatives of compounds of Formula (I). For example, when compounds of Formula (I) contain an oxidizable nitrogen atom, the nitrogen atom can be converted to an N-oxide by methods well known in the art. When compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. 1981, the disclosure of which is incorporated herein by reference in its entirety. The protected derivatives of compounds of Formula (I) can be prepared by methods well known in the art.

"Phenylene" means a divalent phenyl radical.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated.

Certain compounds of Formula (I) can exist as tautomers and/or geometric isomers. All possible tautomers and cis and trans isomers, individual and mixtures thereof are within the scope of this invention. Additionally, as used herein the terms alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth. Furthermore, all polymorphic forms and hydrates of a compound of Formula (I) are within the scope of this invention.

"Optionally substituted phenyl" means a phenyl ring optionally substituted with one, two, or three substituents independently selected from alkyl, halo, alkoxy, alkylthio, haloalkyl, haloalkoxy, heteroaryl (that is optionally substituted with one or two substituents independently selected from alkyl, halo, hydroxy, alkoxy, carboxy, amino, alkylamino, or dialkylamino), heterocycloalkyl (that is optionally substituted with one or two substituents independently selected from alkyl, halo, hydroxy, alkoxy, carboxy, amino, alkylamino, or dialkylamino), amino, alkylamino, dialkylamino, hydroxy, cyano, nitro, methylenedioxy, aminocarbonyl, acylamino, hydroxyalkyl, alkoxycarbonyl, aminoalkyl, or carboxy or optionally substituted with five fluorine atoms. When the phenyl is substituted it is referred herein as "substituted phenyl".

"Optionally substituted phenyloxy or phenoxy" means a —OR radical where R is optionally substituted phenyl as defined above e.g., phenoxy, chlorophenoxy, and the like.

"Optionally substituted phenylcarbonylamino" means a —NHCOR radical where R is optionally substituted phenyl as defined above e.g., benzoylamino, and the like.

"Optionally substituted phenylalkyl" means a -(alkylene)-R radical where R is optionally substituted phenyl as defined above e.g., benzyl, phenylethyl, and the like.

"Optionally substituted phenylalkyloxy" means a —OR radical where R is optionally substituted phenylalkyl as defined above e.g., benzyloxy, phenylethyloxy, and the like.

"Optionally substituted phenylalkylthio" means a —S-(alkylene)-R radical where R is optionally substituted phenyl as defined above e.g., benzylthio, phenylethylthio, and the like.

"Optionally substituted phenylalkylsulfonyl" means a —SO$_2$-(alkylene)-R radical where R is optionally substituted phenyl as defined above e.g., benzylsulfonyl, phenylethylsulfonyl, and the like.

"Optionally substituted phenylalkenyl" means a -(alkenylene)-R radical where R is optionally substituted as defined above e.g., phenylethenyl, phenylpropenyl, and the like.

"Optionally substituted phenoxyalkyl" means a -(alkylene)-OR radical where R is optionally substituted phenyl as defined above e.g., phenoxymethyl, phenoxyethyl, and the like.

"Optionally substituted heteroaryl" means a monovalent monocyclic or bicyclic aromatic radical of 5 to 10 ring atoms where one or more, preferably one, two, or three, ring atoms are heteroatoms selected from N, O, or S, the remaining ring atoms being carbon that is optionally substituted with one, two, or three substituents independently selected from alkyl, halo, alkoxy, haloalkyl, haloalkoxy, amino, alkylamino, dialkylamino, hydroxy, cyano, nitro, aminocarbonyl, hydroxyalkyl, alkoxycarbonyl, aminoalkyl, optionally substituted phenyl, optionally substituted phenoxy, carboxy, or heteroaryl that is optionally substituted with alkyl, halo, hydroxy, alkoxy, carboxy, amino, alkylamino, or dialkylamino, heterocycloalkyl optionally substituted with one or two substituents independently selected from alkyl, halo, hydroxy, alkoxy, amino, alkylamino or dialkylamino, heterocycloalkylalkyl optionally substituted with one or two substituents independently selected from alkyl, halo, hydroxy, alkoxy, amino, alkylamino or dialkylamino, or heteroarylamino optionally substituted with one or two substituents independently selected from alkyl, halo, hydroxy, alkoxy, amino, alkylamino or dialkylamino. More specifically the term optionally substituted heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isoxazolyl, benzoxazolyl, quinolinyl, isoquinolinyl, benzopyranyl, and thiazolyl, and the derivatives thereof (formed when the heteroaryl ring is substituted with a substituent listed above); or an N-oxide or a protected derivative thereof.

"Optionally substituted heteroaryloxy" means a —OR radical where R is optionally substituted heteroaryl as defined above e.g., furanyloxy, pyridinyloxy, and the like.

"Optionally substituted heteroaralkyloxy" means a —OR radical where R is optionally substituted heteroaralkyl ring as defined below.

"Optionally substituted heteroaryloxyalkyl" means a -(alkylene)-OR radical where R is optionally substituted heteroaryl ring as defined above.

"Optionally substituted heteroaralkyl" means a -(alkylene)-R radical where R is optionally substituted heteroaryl ring as defined above.

"Optionally substituted heterocycloalkyl" means a saturated or unsaturated monovalent cyclic group of 3 to 8 ring atoms in which one or two ring atoms are heteroatoms selected from N, O, or S(O)$_n$, where n is an integer from 0 to 2, the remaining ring atoms being C. One or two ring carbon atoms can optionally be replaced by a —CO— group. More specifically the term heterocycloalkyl includes, but is not limited to, pyrrolidino, piperidino, morpholino, piperazino, tetrahydropyranyl, and thiomorpholino and the derivatives thereof (formed when the heterocycloalkyl ring is substituted with a substituent listed below); or an N-oxide or a protected derivative thereof. The heterocycloalkyl is optionally fused to aryl and is optionally substituted with one, two, or three substituents independently selected from alkyl, cycloalkyl, halo, alkoxy, haloalkyl, haloalkoxy, amino, alkylamino, dialkylamino, hydroxy, cyano, nitro, optionally substituted phenylalkyl, optionally substituted heteroaralkyl aminocarbonyl, hydroxyalkyl, alkoxycarbonyl, aminoalkyl, or carboxy.

"Optionally substituted heterocycloalkyloxy" means a —OR radical where R is optionally substituted heterocycloalkyl ring as defined above.

"Optionally substituted heterocycloalkylalkyl" means a -(alkylene)-R radical where R is optionally substituted heterocycloalkyl ring as defined above.

"Optionally substituted heterocycloalkylalkyloxy" means a —OR radical where R is optionally substituted heterocycloalkylalkyl ring as defined above.

"Optionally substituted heterocycloalkyloxyalkyl" means a -(alkylene)-OR radical where R is optionally substituted heterocycloalkyl as defined above e.g., piperidinyloxymethyl, pyrrolidinyloxyethyl, and the like.

"Optional" or "optionally" means that the subsequently described event or circumstance may but need not occur, and that the description includes instances where the event or circumstance occurs and instances in which it does not. For example, "heterocycloalkyl group optionally mono- or disubstituted with an alkyl group" means that the alkyl may but need not be present, and the description includes situations where the heterocycloalkyl group is mono- or disubstituted with an alkyl group and situations where the heterocycloalkyl group is not substituted with the alkyl group.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Treating" or "treatment" of a disease includes:

(i) preventing the disease, i.e. causing the clinical symptoms of the disease not to develop in a mammal that may be exposed to or predisposed to the disease but does not yet experience or display symptoms of the disease;

(ii) inhibiting the disease, i.e., arresting or reducing the development of the disease or its clinical symptoms; or (iii) relieving the disease, i.e., causing regression of the disease or its clinical symptoms.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

Representative compounds of Formula (I) are disclosed in Table I-IV below.

Compounds of Formula (I) where $R^1$ and $R^3$ are hydrogen, $Ar^1$ is phenyl and $Ar^2$ and Y are as defined in Table 1 below are:

TABLE I

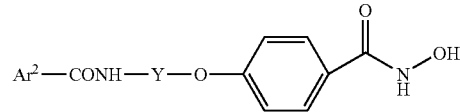

| Cpd # | $Ar^2$ | Y |
|---|---|---|
| 1 | phenyl | —CH$_2$—CH$_2$— |
| 2 | trans phenyl-CH=CH— | —CH$_2$—CH$_2$— |
| 3 | trans phenylcyclopropyl | —CH$_2$—CH$_2$— |
| 4 | trans 4-MeO-phenyl-CH=CH— | —CH$_2$—CH$_2$— |
| 5 | 2-phenylethyl | —CH$_2$—CH$_2$— |
| 6 | 1H-indol-3-ylmethyl | —CH$_2$—CH$_2$— |
| 7 | thiophen-2-yl | —CH$_2$—CH$_2$— |
| 8 | pyridin-3-yl | —CH$_2$—CH$_2$— |
| 9 | 4-biphenyl | —CH$_2$—CH$_2$— |
| 10 | 3-biphenyl | —CH$_2$—CH$_2$— |
| 11 | 5-phenylthiophen-2-yl | —CH$_2$—CH$_2$— |
| 12 | thiophen-2-ylmethyl | —CH$_2$—CH$_2$— |
| 13 | naphth-2-yl | —CH$_2$—CH$_2$— |
| 14 | quinolin-6-yl | —CH$_2$—CH$_2$— |
| 15 | 4-phenylthiazol-2-yl | —CH$_2$—CH$_2$— |
| 16 | 4-tert-butylphenyl | —CH$_2$—CH$_2$— |
| 17 | trans pyridin-3-yl-CH=CH— | —CH$_2$—CH$_2$— |
| 18 | 4-pyrrol-1-ylphenyl | —CH$_2$—CH$_2$— |
| 19 | 4-(cyclohexene-3-oxy)-phenyl | —CH$_2$—CH$_2$— |
| 20 | benzothiazol-2-yl | —CH$_2$—CH$_2$— |
| 21 | benzoxazol-2-yl | —CH$_2$—CH$_2$— |
| 22 | octahydroisoquinolin-2-ylmethyl | —CH$_2$—CH$_2$— |
| 23 | 4-pyridin-4-yl-piperazin-1-ylmethyl | —CH$_2$—CH$_2$— |
| 24 | furan-2-yl | —CH$_2$—CH$_2$— |
| 25 | 4-(pyridin-3-yl)-phenyl | —CH$_2$—CH$_2$— |
| 26 | 4-(pyridin-2-yl)-phenyl | —CH$_2$—CH$_2$— |
| 27 | 1H-benzimidazol-2-yl | —CH$_2$—CH$_2$— |
| 28 | 1H-pyrrol-2-yl | —CH$_2$—CH$_2$— |
| 29 | 4-(benzoylamino)-phenyl | —CH$_2$—CH$_2$— |
| 30 | 4-(pyridin-4-yl)-thiazol-2-yl | —CH$_2$—CH$_2$— |
| 31 | adamantan-1-yl | —CH$_2$—CH$_2$— |
| 32 | 2,4-difluorophenyl | —CH$_2$—CH$_2$— |
| 33 | trans 3,4-methylenedioxyphenylCH=CH— | —CH$_2$—CH$_2$— |
| 34 | 3,4-methylenedioxyphenyl | —CH$_2$—CH$_2$— |
| 35 | 3,4-dimethoxyphenyl | —CH$_2$—CH$_2$— |
| 36 | 3,5-dimethoxyphenyl | —CH$_2$—CH$_2$— |
| 37 | 3,4-difluorophenyl | —CH$_2$—CH$_2$— |
| 38 | 2,5-dimethylphenyl | —CH$_2$—CH$_2$— |
| 39 | 2,3-dichlorophenyl | —CH$_2$—CH$_2$— |
| 40 | 2,3-dimethylphenyl | —CH$_2$—CH$_2$— |
| 41 | 4-chloro-2-methoxyphenyl | —CH$_2$—CH$_2$— |
| 42 | 3-ethoxyphenyl | —CH$_2$—CH$_2$— |
| 43 | 4-methoxy-2-methylphenyl | —CH$_2$—CH$_2$— |
| 44 | 3-fluoro-4-methoxyphenyl | —CH$_2$—CH$_2$— |
| 45 | 2-(thiophen-2-ylmethoxy)phenyl | —CH$_2$—CH$_2$— |
| 46 | 3-(thiophen-2-ylmethoxy)-phenyl | —CH$_2$—CH$_2$— |
| 47 | 2-phenylphenyl | —CH$_2$—CH$_2$— |
| 48 | 1H-indol-5-yl | —CH$_2$—CH$_2$— |
| 49 | 1H-indol-3-yl | —CH$_2$—CH$_2$— |
| 50 | quinolin-3-yl | —CH$_2$—CH$_2$— |
| 51 | quinolin-8-yl | —CH$_2$—CH$_2$— |
| 52 | 1H-indazol-3-yl | —CH$_2$—CH$_2$— |
| 53 | 1H-benzotriazol-5-yl | —CH$_2$—CH$_2$— |
| 54 | isoquinolin-1-yl | —CH$_2$—CH$_2$— |
| 55 | isoquinolin-3-yl | —CH$_2$—CH$_2$— |
| 56 | quinoxalin-2-yl | —CH$_2$—CH$_2$— |
| 57 | naphth-1-yl | —CH$_2$—CH$_2$— |
| 58 | quinolin-2-yl | —CH$_2$—CH$_2$— |
| 59 | 2-pyrrol-1-yl-phenyl | —CH$_2$—CH$_2$— |

TABLE I-continued

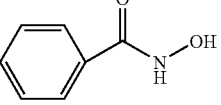

| Cpd # | Ar² | Y |
|---|---|---|
| 60 | 4-fluoronaphth-1-yl | —CH₂—CH₂— |
| 61 | 1H-benzimidazol-5-yl | —CH₂—CH₂— |
| 62 | 1-methyl-indol-3-yl | —CH₂—CH₂— |
| 63 | 4-MeO-quinolin-2-yl | —CH₂—CH₂— |
| 64 | 3-MeO-naphth-2-yl | —CH₂—CH₂— |
| 65 | 2-MeO-naphth-1-yl | —CH₂—CH₂— |
| 66 | quinolin-4-yl | —CH₂—CH₂— |
| 67 | trans phenyl-CH═C(CH₃)— | —CH₂—CH₂— |
| 68 | 2-N,N-dimethylaminomethylbenzofuran-5-yl | —CH₂—CH₂— |
| 69 | indolin-1-yl | —CH₂—CH₂— |
| 70 | 1,2,3,4-tetrahydroquinolin-1-yl | —CH₂—CH₂— |
| 71 | trans 5-hydroxybenzofuran-2-yl-C(CH₃)═CH— | —(S)—CH(CH₂CH₃)—CH₂— |
| 72 | trans 5-(1-cyclopropylpiperidin-4-yloxy)benzofuran-2-yl-C(CH₃)═CH— | —(S)—CH(CH₂CH₃)—CH₂— |
| 73 | benzofuran-2-yl | —(S)—CH(2-phenylethyl)-CH₂— |
| 74 | 5-(1-cyclopropylpiperidin-4-yloxy)benzofuran-2-yl | —CH₂—CH₂— |
| 75 | 5-(1-cyclopropylpiperidin-4-yloxy)benzofuran-2-yl | —(S)—CH(CH₂CH₃)—CH₂— |
| 76 | 5-(1-cyclopropylpiperidin-4-yloxy)benzofuran-2-yl | —(R)—CH₂—CH(CH₃)— |
| 77 | 5-[1-(2,2,2-trifluoroethyl)piperidin-4-yloxy]benzofuran-2-yl | —CH₂—CH₂— |
| 78 | benzofuran-2-yl | —(R)—CH(benzylSO₂-methyl)-CH₂— |
| 79 | benzofuran-2-yl | —(R)—CH(benzylS-methyl)-CH₂— |
| 80 | trans 5-methoxybenzofuran-2-yl-C(CH₃)═CH— | —CH₂—CH₂— |
| 81 | 1,2,3,4-tetrahydroisoquinolin-2-yl | —CH₂—CH₂— |
| 82 | isoindolin-2-yl | —CH₂—CH₂— |
| 83 | morpholin-4-yl | —CH₂—CH₂— |
| 84 | 4-benzyl-piperazin-1-yl | —CH₂—CH₂— |
| 85 | (R)-3-HO-pyrrolidin-1-yl | —CH₂—CH₂— |
| 86 | piperidin-1-yl | —CH₂—CH₂— |
| 87 | 6-CH₃-1,2,3,4-tetrahydroquinolin-1-yl | —CH₂—CH₂— |
| 88 | 2-CH₃-indolin-1-yl | —CH₂—CH₂— |
| 89 | 6-F-2-CH₃-1,2,3,4-tetrahydroquinolin-1-yl | —CH₂—CH₂— |
| 90 | isoindolin-1-yl | —(S)—CH(CH₂CH₃)—CH₂— |
| 91 | trans phenyl-CH═CH— | —CH₂—CH₂—CH₂— |
| 92 | trans 4-CH₃O-phenyl-CH═CH— | —CH₂—CH₂—CH₂— |
| 93 | 4-phenylthiazol-2-yl | —CH₂—CH₂—CH₂— |
| 94 | trans phenyl-CH═CH— | —(S)—CH(methyl)-CH₂— |
| 95 | trans phenyl-CH═CH— | —(R)—CH(methyl)-CH₂— |
| 96 | trans phenyl-CH═CH— | —(S)—CH(i-butyl)-CH₂— |
| 97 | trans phenyl-CH═CH— | —(S)—CH(cyclohexyl-methyl)-CH₂— |
| 98 | trans phenyl-CH═CH— | —(S)—CH(i-propyl)-CH₂— |
| 99 | trans phenyl-CH═CH— | —(S)—CH(benzyl)-CH₂— |
| 100 | trans phenyl-CH═CH— | —(R)—CH(benzyl)-CH₂— |
| 101 | trans phenyl-CH═CH— | —(R)—CH(i-butyl)-CH₂— |
| 102 | trans phenyl-CH═CH— | —(R)—CH(i-propyl)-CH₂— |
| 103 | trans phenyl-CH═CH— | —(RS)—CH(n-butyl)-CH₂— |
| 104 | trans phenyl-CH═CH— | —(RS)—CH(4-Cl-benzyl)-CH₂— |
| 105 | trans phenyl-CH═CH— | —(S)—CH(CH₂CH₃)—CH₂— |
| 106 | trans phenyl-CH═CH— | —(R)—CH(CH₂CH₃)—CH₂— |
| 107 | trans phenyl-CH═CH— | —(S)—CH(2-MeS-ethyl)-CH₂— |
| 108 | trans phenyl-CH═CH— | —(R)—CH(2-MeS-ethyl)-CH₂— |
| 109 | trans phenyl-CH═CH— | —(S)—CH(phenyl)-CH₂— |
| 110 | trans phenyl-CH═CH— | —(R)—CH(phenyl)-CH₂— |
| 111 | trans phenyl-CH═CH— | —(S)—CH(2-MeSO₂-ethyl)-CH₂— |
| 112 | trans phenyl-CH═CH— | —(R)—CH(2-MeSO₂-ethyl)-CH₂— |
| 113 | trans phenyl-CH═CH— | —(R)—CH(benzylSO₂-methyl)-CH₂— |
| 114 | thiophen-2-yl | —(S)—CH(CH₂CH₃)—CH₂— |
| 115 | 4-biphenyl | —(S)—CH(CH₂CH₃)—CH₂— |
| 116 | naphth-2-yl | —(S)—CH(CH₂CH₃)—CH₂— |
| 117 | trans phenyl-CH═CH— | —(R)—CH(benzyl-S-methyl)-CH₂— |
| 118 | phenyl | —(S)—CH(CH₂CH₃)—CH₂— |
| 119 | benzyl | —(S)—CH(CH₂CH₃)—CH₂— |
| 120 | 2-phenylethyl | —(S)—CH(CH₂CH₃)—CH₂— |
| 121 | trans phenyl-CH═CH— | —(S)—CH(hydroxy-methyl)-CH₂— |
| 122 | 4-phenylthiazol-2-yl | —(S)—CH(CH₂CH₃)—CH₂— |

TABLE I-continued $$Ar^2-CONH-Y-O-\underset{}{\underset{}{\bigcirc}}-\underset{H}{\overset{O}{\underset{}{C}}}-N-OH$$

| Cpd # | Ar² | Y |
|---|---|---|
| 123 | trans 4-CH₃O-phenyl-CH=CH— | —(S)—CH(CH₂CH₃)—CH₂— |
| 124 | 2-N,N-dimethylaminomethyl-benzofuran-5-yl- | —(S)—CH(CH₂CH₃)—CH₂— |
| 125 | trans phenyl-CH=CH— | —(R)—CH₂—CH(CH₃)— |
| 126 | trans phenyl-CH=CH— | —(S)—CH₂—CH(CH₃)— |
| 127 | 4-phenyl-thiazol-2-yl | —(R)—CH₂—CH(CH₃)— |
| 128 | 4-phenyl-thiazol-2-yl | —(S)—CH₂—CH(CH₃)— |
| 129 | 4-biphenyl | —(R)—CH₂—CH(CH₃)— |
| 130 | trans 4-CH₃O-phenyl-CH=CH— | —(R)—CH₂—CH(CH₃)— |
| 131 | 4-(2-pyridin-4-ylthiazol-5-yl)phenyl | —CH₂—CH₂— |
| 132 | 7-chloro-4-methylbenzofuran-2-yl | —CH₂—CH₂— |
| 133 | 4-[2-(4-methylpiperazin-1-yl)thiazol-5-yl]-phenyl | —CH₂—CH₂— |
| 134 | 4-(2-pyridin-4-ylaminothiazol-5-yl)phenyl | —CH₂—CH₂— |
| 135 | 4-(4-methylpiperazin-1-yl)phenyl | —CH₂—CH₂— |
| 136 | 4-(4-hydroxypiperidin-1-yl)phenyl | —CH₂—CH₂— |
| 137 | 4-(4-morpholin-4-ylmethylthiazol-2-yl)phenyl | —CH₂—CH₂— |
| 138 | 7-fluoro-4-methylbenzofuran-2-yl | —CH₂—CH₂— |
| 139 | 7-fluoro-4-(2-methoxyethoxymethyl)-benzofuran-2-yl | —CH₂—CH₂— |
| 140 | 4-hydroxyquinolin-2-yl | —CH₂—CH₂— |
| 141 | 7-fluoro-4-phenoxymethylbenzofuran-2-yl | —CH₂—CH₂— |
| 143 | 4-[2-(4-methylpiperazin-1-ylmethyl)thiazol-5-yl]phenyl | —CH₂—CH₂— |
| 144 | pyridin-2-yl | —CH₂—CH₂— |
| 145 | 3-hydroxypyridin-2-yl | —CH₂—CH₂— |
| 146 | 6-hydroxypyridin-2-yl | —CH₂—CH₂— |
| 147 | 6-(4-nitrophenoxy)pyridin-2-yl | —CH₂—CH₂— |
| 148 | 4-(2-methoxyethoxy)quinolin-2-yl | —CH₂—CH₂— |
| 149 | 4-(2-dimethylaminoethoxy)quinolin-2-yl | —CH₂—CH₂— |
| 150 | 6-bromopyridin-2-yl | —CH₂—CH₂— |
| 151 | 5-bromopyridin-3-yl | —CH₂—CH₂— |
| 152 | 4-methoxyquinolin-2-yl | —(S)—CH(CH₂CH₃)—CH₂— |
| 153 | 1-methoxynaphth-2-yl | —CH₂—CH₂— |
| 154 | 4-methoxyquinolin-2-yl | —(R)—CH₂—CH(CH₃)— |
| 155 | 5-phenylpyridin-3-yl | —CH₂—CH₂— |
| 156 | 6-benzyloxypyridin-2-yl | —CH₂—CH₂— |
| 157 | 6-(2-methylpropyloxy)pyridin-2-yl | —CH₂—CH₂— |
| 158 | 6-(2-phenylethyloxy)pyridin-2-yl | —CH₂—CH₂— |
| 159 | 4-(3,3,3-trifluoropropyloxy)quinolin-2-yl | —CH₂—CH₂— |
| 160 | 4-(3,3,3-trifluoropropyloxy)quinolin-2-yl | —(S)—CH(CH₂CH₃)—CH₂— |
| 161 | 4-(3,3,3-trifluoropropyloxy)quinolin-2-yl | —(R)—CH₂—CH(CH₃)— |
| 162 | trans 3-hydroxyphenyl-CH=CH— | —CH₂—CH₂— |
| 163 | trans 4-hydroxyphenyl-CH=CH— | —CH₂—CH₂— |
| 164 | 3'-(2-hydroxyethyl)biphen-4-yl | —CH₂—CH₂— |
| 165 | 3'-(2-hydroxyethyl)biphen-3-yl | —CH₂—CH₂— |
| 166 | 2'-(2-hydroxyethyl)biphen-4-yl | —CH₂—CH₂— |
| 167 | trans benzofuran-2-yl-CH=CH— | —CH₂—CH₂— |
| 168 | 2'-(2-hydroxyethyl)biphen-3-yl | —CH₂—CH₂— |
| 169 | 5-thiophen-3-ylpyridin-3-yl | —CH₂—CH₂— |
| 170 | 6-(4-acetylaminophenoxy)pyridin-2-yl | —CH₂—CH₂— |
| 171 | 6-(4-aminophenoxy)pyridin-2-yl | —CH₂—CH₂— |
| 172 | trans 2-methoxyphenyl-CH=CH— | —CH₂—CH₂— |
| 173 | trans 3-methoxyphenyl-CH=CH— | —CH₂—CH₂— |
| 174 | 5-(4-dimethylaminophenyl)pyridin-3-yl | —CH₂—CH₂— |
| 175 | trans 5-bromothiophen-2-yl-CH=CH— | —CH₂—CH₂— |
| 176 | trans furan-3-yl-CH=CH— | —CH₂—CH₂— |
| 177 | trans thiophen-3-yl-CH=CH— | —CH₂—CH₂— |
| 178 | trans thiophen-2-yl-CH=CH— | —CH₂—CH₂— |
| 179 | trans 3-tolyl-CH=CH— | —CH₂—CH₂— |
| 180 | trans 4-tolyl-CH=CH— | —CH₂—CH₂— |
| 181 | trans benzofuran-2-yl-C(CH₃)=CH— | —CH₂—CH₂— |
| 182 | cis benzofuran-2-yl-C(CH₃)=CH— | —CH₂—CH₂— |
| 183 | trans 4-dimethylaminophenyl-CH=CH— | —CH₂—CH₂— |
| 184 | trans indol-3-yl-CH=CH— | —CH₂—CH₂— |
| 185 | trans 2-tolyl-CH=CH— | —CH₂—CH₂— |
| 186 | trans 2-hydroxyphenyl-CH=CH— | —CH₂—CH₂— |
| 187 | trans 7-methoxybenzofuran-2-yl-CH=CH— | —CH₂—CH₂— |

TABLE I-continued

| Cpd # | Ar² | Y |
|---|---|---|
| 188 | trans 7-methoxybenzofuran-2-yl-CH=CH— | —(R)—CH(CH₂CH₃)—CH₂— |
| 189 | trans 5-methoxybenzofuran-2-yl-C(CH₃)=CH— | —(S)—CH(CH₂CH₃)—CH₂— |
| 190 | trans furan-2-yl-CH=CH— | —CH₂—CH₂— |
| 191 | 4-[4-(2-morpholin-4-ylethyl)thiazol-2-yl]phenyl | —CH₂—CH₂— |

General structure: Ar²—CONH—Y—O—(phenyl)—C(=O)—NH—OH and are named as:
N-hydroxy-4-(2-benzenecarbonylamino-ethoxy)benzamide;
N-hydroxy-4-(2-trans-cinnamoylaminoethoxy)benzamide;
N-hydroxy-4-(2-trans-2-phenylcyclopropylcarbonylaminoethoxy)benzamide;
N-hydroxy-4-(2-trans-4-methoxycinnamoylaminoethoxy)benzamide;
N-hydroxy-4-[2-(2-phenylethylcarbonylamino)ethoxy]benzamide;
N-hydroxy-4-[2-(1H-indol-3-ylmethylcarbonylamino)ethoxy]benzamide;
N-hydroxy-4-(2-thiophen-2-ylcarbonylaminoethoxy)benzamide;
N-hydroxy-4-(2-pyridin-3-ylcarbonylaminoethoxy)benzamide;
N-hydroxy-4-(2-biphen-4-ylcarbonylaminoethoxy)benzamide;
N-hydroxy-4-(2-biphen-3-ylcarbonylaminoethoxy)benzamide;
N-hydroxy-4-[2-(5-phenylthiophen-2-ylcarbonylamino)ethoxy]benzamide;
N-hydroxy-4-[2-(thiophen-2-ylmethylcarbonylamino)ethoxy]benzamide;
N-hydroxy-4-[2-(napth-2-ylcarbonylamino)ethoxy]benzamide;
N-hydroxy-4-[2-(quinolin-6-ylcarbonylamino)ethoxy]benzamide;
N-hydroxy-4-[2-(4-phenylthiazol-2-ylcarbonylamino)ethoxy]benzamide;
N-hydroxy-4-[2-(4-tert-butylphenylcarbonylamino)ethoxy]benzamide;
N-hydroxy-4-[2-(trans-3-pyridin-3-ylacryloylamino)ethoxy]benzamide;
N-hydroxy-4-[2-(4-pyrrol-1-ylphenylcarbonylamino)ethoxy]benzamide;
N-hydroxy-4-[2-(4-cyclohexene-3-oxyphenylcarbonylamino)ethoxy]benzamide;
N-hydroxy-4-[2-(benzthiazol-2-ylcarbonylamino)ethoxy]benzamide;
N-hydroxy-4-[2-(benzoxazol-2-ylcarbonylamino)ethoxy]benzamide;
N-hydroxy-4-[2-(octahydroisoquinolin-2-ylmethylcarbonylamino)ethoxy]benzamide;
N-hydroxy-4-[2-(4-pyridin-4-ylpiperazin-1-ylmethylcarbonylamino)ethoxy]benzamide;
N-hydroxy-4-[2-(furan-2-ylcarbonylamino)ethoxy]benzamide;
N-hydroxy-4-[2-(4-pyridin-3-ylphenylcarbonylamino)ethoxy]benzamide;
N-hydroxy-4-[2-(4-pyridin-2-ylphenylcarbonylamino)ethoxy]benzamide;
N-hydroxy-4-[2-(benzimidazol-2-ylcarbonylamino)ethoxy]benzamide;
N-hydroxy-4-[2-(1H-pyrrol-2-ylcarbonylamino)ethoxy]benzamide;
N-hydroxy-4-[2-(4-benzoylaminophenylcarbonylamino)ethoxy]benzamide;
N-hydroxy-4-[2-(4-pyridin-4-ylthiazol-2-ylcarbonylamino)ethoxy]benzamide;
N-hydroxy-4-[2-(admantan-1-ylcarbonylamino)ethoxy]benzamide;
N-hydroxy-4-[2-(2,4-difluorophenylcarbonylamino)ethoxy]benzamide;
N-hydroxy-4-[2-(3-trans-3,4-methylenedioxyphenylacryloylaminonethoxy]-benzamide;
N-hydroxy-4-[2-(3,4-methylenedioxyphenylcarbonylamino)ethoxy]benzamide;
N-hydroxy-4-[2-(3,4-dimethoxyphenylcarbonylamino)ethoxy]benzamide;
N-hydroxy-4-[2-(3,5-dimethoxyphenylcarbonylamino)ethoxy]benzamide;
N-hydroxy-4-[2-(3,4-difluorophenylcarbonylamino)ethoxy]benzamide;
N-hydroxy-4-[2-(2,5-dimethylphenylcarbonylamino)ethoxy]benzamide;
N-hydroxy-4-[2-(2,3-dichlorophenylcarbonylamino)ethoxy]benzamide;
N-hydroxy-4-[2-(2,3-dimethylphenylcarbonylamino)ethoxy]benzamide;
N-hydroxy-4-[2-(4-chloro-2-methoxyphenylcarbonylamino)ethoxy]benzamide;
N-hydroxy-4-[2-(3-ethoxyphenylcarbonylamino)ethoxy]benzamide;
N-hydroxy-4-[2-(4-methoxy-2-methylphenylcarbonylamino)ethoxy]benzamide;
N-hydroxy-4-[2-(3-fluoro-4-methoxyphenylcarbonylamino)ethoxy]benzamide;
N-hydroxy-4-[2-(2-thiophen-2-ylmethoxyphenylcarbonylamino)ethoxy]benzamide;
N-hydroxy-4-[2-(3-thiophen-2-ylmethoxyphenylarbonylamino)ethoxy]benzamide;
N-hydroxy-4-[2-(biphen-2-ylcarbonylamino)ethoxy]benzamide;
N-hydroxy-4-[2-(1H-indol-5-ylcarbonylamino)ethoxy]benzamide;
N-hydroxy-4-[2-(1H-indol-3-ylcarbonylamino)ethoxy]benzamide;
N-hydroxy-4-[2-(quinolin-3-ylcarbonylamino)ethoxy]benzamide;
N-hydroxy-4-[2-(quinolin-8-ylcarbonylamino)ethoxy]benzamide;

N-hydroxy-4-[2-(1H-indazol-3-ylcarbonylamino)ethoxy]benzamide;
N-hydroxy-4-[2-(1H-benzotriazol-5-ylcarbonylamino)ethoxy]benzamide;
N-hydroxy-4-[2-(isoquinolin-1-ylcarbonylamino)ethoxy]benzamide;
N-hydroxy-4-[2-(isoquinolin-3-ylcarbonylamino)ethoxy]benzamide;
N-hydroxy-4-[2-(quinoxalin-2-ylcarbonylamino)ethoxy]benzamide;
N-hydroxy-4-[2-(naphth-1-ylcarbonylamino)ethoxy]benzamide;
N-hydroxy-4-[2-(quinolin-2-ylcarbonylamino)ethoxy]benzamide;
N-hydroxy-4-[2-(2-pyrrol-1-ylphenylcarbonylamino)ethoxy]benzamide;
N-hydroxy-4-[2-(4-fluoronapth-1-ylcarbonylamino)ethoxy]benzamide;
N-hydroxy-4-[2-(1H-benzimidazol-5-ylcarbonylamino)ethoxy]benzamide;
N-hydroxy-4-[2-(1-methylindol-3-ylcarbonylamino)ethoxy]benzamide;
N-hydroxy-4-[2-(4-methoxyquinolin-2-ylcarbonylamino)ethoxy]benzamide;
N-hydroxy-4-[2-(3-methoxynapth-2-ylcarbonylamino)ethoxy]benzamide;
N-hydroxy-4-[2-(2-methoxynapth-1-ylcarbonylamino)ethoxy]benzamide;
N-hydroxy-4-[2-(quinolin-4-ylcarbonylamino)ethoxy]benzamide;
N-hydroxy-4-[2-(trans-2-methylcinnamoylamino)ethoxy]benzamide;
N-hydroxy-4-[2-(2-N,N-dimethylaminomethylbenzofuran-5-ylcarbonylamino)ethoxy]-benzamide;
N-hydroxy-4-(2-indolin-1-ylcarbonylaminoethoxy)benzamide;
N-hydroxy-4-[2-(1,2,3,4-tetrahydroquinolin-1-ylcarbonylamino)ethoxy]benzamide;
N-hydroxy-4-{2S-[trans-3-(5-hydroxybenzofuran-2-yl)but-2-enoylamino]butoxy}benzamide;
N-hydroxy-4-{2S-[trans-3-(5-(1-cyclopropylpiperidin-4-yloxy)benzofuran-2-yl)but-2-enoyl-amino]butoxy}benzamide;
N-hydroxy-4-[2S-(benzofuran-2-ylcarbonylamino)-4-phenylbutoxy]benzamide;
N-hydroxy-4-{2-[5-(1-cyclopropylpiperidin-4-yloxy)benzofuran-2-ylcarbonylamino]-ethoxy}benzamide;
N-hydroxy-4-{2S-[5-(1-cyclopropylpiperidin-4-yloxy)benzofuran-2-ylcarbonylamino]-butoxy}benzamide;
N-hydroxy-4-{2-[5-(1-cyclopropylpiperidin-4-yloxy)benzofuran-2-ylcarbonylamino]-1R-methylethoxy}benzamide;
N-hydroxy-4-{2-[5-(1-(2,2,2-trifluoroethyl)piperidin-4-yloxy)benzofuran-2-ylcarbonylamino]-ethoxy}benzamide;
N-hydroxy-4-[2R-(benzofuran-2-ylcarbonylamino)-3-benzylsulfonylpropoxy]-benzamide;
N-hydroxy-4-[2R-(benzofuran-2-ylcarbonylamino)-3-benzylthiopropoxy]benzamide;
N-hydroxy-4-[2-(trans-3-(5-methoxybenzofuran-2-yl)but-2-enoylcarbonylamino)ethoxy]benzamide;
N-hydroxy-4-[2-(1,2,3,4-tetrahydroisoquinolin-2-ylcarbonylamino)ethoxy]benzamide;
N-hydroxy-4-[2-(isoindolin-2-ylcarbonylamino)ethoxy]benzamide;
N-hydroxy-4-[2-(morpholin-4-ylcarbonylamino)ethoxy]benzamide;
N-hydroxy-4-[2-(4-benzylpiperazin-1-ylcarbonylamino)ethoxy]benzamide;
N-hydroxy-4-[2-(3(R)-hydroxypyrrolidin-1-ylcarbonylamino)ethoxy]benzamide;
N-hydroxy-4-[2-(piperidin-1-ylcarbonylamino)ethoxy]benzamide;
N-hydroxy-4-[2-(6-methyl-1,2,3,4-tetrahydroquinolin-1-ylcarbonylamino)ethoxy]-benzamide;
N-hydroxy-4-[2-(2-methylindolin-1-ylcarbonylamino)ethoxy]benzamide;
N-hydroxy-4-[2-(6-fluoro-2-methyl-1,2,3,4-tetrahydroquinolin-1-ylcarbonylamino)ethoxy]benzamide;
N-hydroxy-4-[2S-(isoindolin-1-ylcarbonylamino)butoxy]benzamide;
N-hydroxy-4-[3-(trans-cinnamoylamino)propoxy]benzamide;
N-hydroxy-4-[3-(trans-4-methoxycinnamoylamino)propoxy]benzamide;
N-hydroxy-4-[3-(4-phenylthiazol-2-ylcarbonylamino)propoxy]benzamide;
N-hydroxy-4-[2S-trans-cinnamoylamino)propoxy]benzamide;
N-hydroxy-4-[2R-(trans-cinnamoylamino)propoxy]benzamide;
N-hydroxy-4-[2S-trans-cinnamoylamino)-4-methylpentoxy]benzamide;
N-hydroxy-4-[2S-trans-cinnamoylamino)-3-cyclohexylpropoxy]benzamide;
N-hydroxy-4-[2S-(trans-cinnamoylamino)-3-methylbutoxy]benzamide;
N-hydroxy-4-[2S-(trans-cinnamoylamino)-3-phenylpropoxy]benzamide;
N-hydroxy-4-[2R-(trans-cinnamoylamino)-3-phenylpropoxy]benzamide;
N-hydroxy-4-[2R-(trans-cinnamoylamino)-4-methylpentoxy]benzamide;
N-hydroxy-4-[2R-(trans-cinnamoylamino)-3-methylbutoxy]benzamide;
N-hydroxy-4-[2RS-(trans-cinnamoylamino)hexyloxy]benzamide;
N-hydroxy-4-[2RS-(trans-cinnamoylamino)-3-(4-chlorophenyl)propoxy)benzamide;
N-hydroxy-4-[2S-(trans-cinnamoylamino)butoxy]benzamide;
N-hydroxy-4-[2R-(trans-cinnamoylamino)butoxy]benzamide;
N-hydroxy-4-[2S-(trans-cinnamoylamino)-4-methylthiobutoxy)benzamide;
N-hydroxy-4-[2R-(trans-cinnamoylamino)-4-methylthiobutoxy]benzamide;
N-hydroxy-4-[2S-(trans-cinnamoylamino)-2-phenylethoxy]benzamide;
N-hydroxy-4-[2R-(trans-cinnamoylamino)-2-phenylethoxy]benzamide;
N-hydroxy-4-[2S-(trans-cinnamoylamino)-4-methylsulfonylbutoxy]benzamide;
N-hydroxy-4-[2R-(trans-cinnamoylamino)-4-methylsulfonylbutoxy]benzamide;
N-hydroxy-4-[2R-(trans-cinnamoylamino)-3-benzylsulfonylpropoxy]benzamide;
N-hydroxy-4-[2S-(thiophen-2-ylcarbonylamino)butoxy]benzamide;
N-hydroxy-4-[2S-(biphen-4-ylcarbonylamino)butoxy]benzamide;
N-hydroxy-4-[2S-(naphth-2-ylcarbonylamino)butoxy]benzamide;

N-hydroxy-4-[2R-(trans-cinnamoylamino)-3-benzylthiopropoxy]benzamide;
N-hydroxy-4-[2S-(benzenecarbonylamino)butoxy]benzamide;
N-hydroxy-4-[2S-(benzylcarbonylamino)butoxy]benzamide;
N-hydroxy-4-[2S-(2-phenylethylcarbonylamino)butoxy]benzamide;
N-hydroxy-4-[2S-(trans-cinnamoylamino)-3-hydroxypropoxy]benzamide;
N-hydroxy-4-[2S-(4-phenylthiazol-2-ylcarbonylamino)butoxy]benzamide;
N-hydroxy-4-[2S-(trans-4-methoxycinnamoylamino)butoxy]benzamide;
N-hydroxy-4-[2S-(2-N,N-dimethylaminomethylbenzofuran-5-ylcarbonylamino)butoxy]-benzamide;
N-hydroxy-4-[2-(trans-cinnamoylamino)-1R-methylethoxy]benzamide;
N-hydroxy-4-[2-(trans-cinnamoylamino)-1S-methylethoxy]benzamide;
N-hydroxy-4-[2-(4-phenylthiazol-2-ylcarbonylamino)-1R-methylethoxy]benzamide;
N-hydroxy-4-[2-(4-phenylthiazol-2-ylcarbonylamino)-1S-methylethoxy]benzamide;
N-hydroxy-4-[2-(biphen-4-ylcarbonylamino)-1R-methylethoxy]benzamide;
N-hydroxy-4-[2-(trans-4-methoxycinnamoylamino)-4R-methylethoxy]benzamide;
N-hydroxy-4-{2-[4-(2-pyridin-2-ylthiazol-5-yl)phenylcarbonylamino]ethoxy}-benzamide;
N-hydroxy-4-[2-(7-chloro-4-methylbenzofuran-2-ylcarbonylamino)ethoxy]benzamide;
N-hydroxy-4-{2-[4-(2-(4-methylpiperazin-1-yl)thiazol-5-yl)phenylcarbonylamino]-ethoxy}benzamide;
N-hydroxy-4-{2-[4-(2-pyridin-4-ylaminothiazol-5-yl)phenylcarbonylamino]ethoxy}-benzamide;
N-hydroxy-4-{2-[4-(4-methylpiperazin-1-yl)phenylcarbonylamino]ethoxy}benzamide;
N-hydroxy-4-{2-[4-(4-hydroxypiperidin-1-yl)phenylcarbonylamino]ethoxy}-benzamide;
N-hydroxy-4-{2-[4-(4-morpholin-4-ylmethylthiazol-5-yl)phenylcarbonylamino]-ethoxy}-benzamide;
N-hydroxy-4-[2-(7-fluoro-4-methylbenzofuran-2-ylcarbonylamino)ethoxy]benzamide;
N-hydroxy-4-{2-[7-fluoro-4-(2-methoxyethoxymethyl)benzofuran-2-ylcarbonylamino)ethoxy}benzamide;
N-hydroxy-4-[2-(4-hydroxyquinolin-2-ylcarbonylamino)ethoxy]benzamide;
N-hydroxy-4-[2-(7-fluoro-4-phenoxymethylbenzofuran-2-ylcarbonylamino)ethoxy]-benzamide;
N-hydroxy-4-{2-[4-(2-(4-methylpiperazin-1-ylmethyl)thiazol-5-yl)phenylcarbonylamino]-ethoxy}benzamide;
N-hydroxy-4-[2-(pyridin-2-ylcarbonylamino)ethoxy]benzamide;
N-hydroxy-4-[2-(3-hydroxypyridin-2-ylcarbonylamino)ethoxy]benzamide;
N-hydroxy-4-[2-(6-hydroxypyridin-2-ylcarbonylamino)ethoxy]benzamide;
N-hydroxy-4-{2-[6-(4-nitrophenoxy)pyridin-2-ylcarbonylamino]ethoxy}benzamide;
N-hydroxy-4-{2-[4-(2-methoxyethoxy)quinolin-2-ylcarbonylamino]ethoxy}benzamide;
N-hydroxy-4-{2-[4-(2-N,N-dimethylaminoethoxy)quinolin-2-ylcarbonylamino]-ethoxy}-benzamide;
N-hydroxy-4-[2-(6-bromopyridin-2-ylcarbonylamino)ethoxy]benzamide;
N-hydroxy-4-[2-(5-bromopyridin-3-ylcarbonylamino)ethoxy]benzamide;
N-hydroxy-4-[2S-(4-methoxyquinolin-2-ylcarbonylamino)butoxy]benzamide;
N-hydroxy-4-[2-(1-methoxynaphth-2-ylcarbonylamino)ethoxy]benzamide;
N-hydroxy-4-[2-(4-methoxyquinolin-2-ylcarbonylamino)-1R-methylethoxy]benzamide;
N-hydroxy-4-[2-(5-phenylpyridin-3-ylcarbonylamino)ethoxy]benzamide;
N-hydroxy-4-[2-(6-benzyloxypyridin-2-ylcarbonylamino)ethoxy]benzamide;
N-hydroxy-4-{2-[6-(2-methylpropyloxy)pyridin-2-ylcarbonylamino]-ethoxy}benzamide;
N-hydroxy-4-{2-[6-(2-phenylethyloxy)pyridin-2-ylcarbonylamino]ethoxy}benzamide;
N-hydroxy-4-{2-[4-(3,3,3-trifluoropropyloxy)quinolin-2-ylcarbonylamino]ethoxy}benzamide;
N-hydroxy-4-{2S-[4-(3,3,3-trifluoropropyloxy)quinolin-2-ylcarbonylamino]butoxy}-benzamide;
N-hydroxy-4-{2-[4-(3,3,3-trifluoropropyloxy)quinolin-2-ylcarbonylamino]-1R-methylethoxy}-benzamide;
N-hydroxy-4-[2-(trans-3-hydroxycinnamoylamino)ethoxy]benzamide;
N-hydroxy-4-[2-(trans-4-hydroxycinnamoylamino)ethoxy]benzamide;
N-hydroxy-4-{2-[3'-(2-hydroxyethyl)biphen-4-ylcarbonylamino]ethoxy}benzamide;
N-hydroxy-4-{2-[3'-(2-hydroxyethyl)biphen-3-ylcarbonylamino]ethoxy}benzamide;
N-hydroxy-4-{2-[2'-(2-hydroxyethyl)biphen-4-ylcarbonylamino]ethoxy}-benzamide;
N-hydroxy-4-[2-(trans-2-benzofuran-2-ylacryloylamino)ethoxy]benzamide;
N-hydroxy-4-{2-[2'-(2-hydroxyethyl)biphen-3-ylcarbonylamino]ethoxy}benzamide;
N-hydroxy-4-{2-[5-(thiophen-3-yl)pyridin-3-ylcarbonylamino]ethoxy}benzamide;
N-hydroxy-4-{2-[6-(4-acetylaminophenoxy)pyridin-2-ylcarbonylamino]ethoxy}-benzamide;
N-hydroxy-4-{2-[6-(4-aminophenoxy)pyridin-2-ylcarbonylamino]ethoxy}benzamide;
N-hydroxy-4-[2-(trans-2-methoxycinnamoylamino)ethoxy]benzamide;
N-hydroxy-4-[2-(trans-3-methoxycinnamoylamino)ethoxy]benzamide;
N-hydroxy-4-{2-[5-(4-dimethylaminophenyl)pyridin-3-ylcarbonylamino]ethoxy}-benzamide;
N-hydroxy-4-{2-[trans-3-(5-bromothiophen-2-yl)acryloylamino]ethoxy}benzamide;
N-hydroxy-4-[2-(trans-3-furan-3-ylacryloylamino)ethoxy]benzamide;
N-hydroxy-4-[2-(trans-3-thiophen-3-ylacryloylamino)ethoxy]benzamide;
N-hydroxy-4-[2-(trans-thiophen-2-ylacryloylamino)ethoxy]benzamide;
N-hydroxy-4-{2-[trans-3-methylcinnamoylamino]ethoxy}benzamide;
N-hydroxy-4-{2-[trans-4-methylcinnamoylamino]ethoxy}benzamide;
N-hydroxy-4-{2-[trans-3-(benzofuran-2-yl)but-2-enoylamino]ethoxy}benzamide;
N-hydroxy-4-{2-[cis-3-(benzofuran-2-yl)but-2-enoylamino]ethoxy}benzamide;
N-hydroxy-4-[2-(trans-4-dimethylaminocinnamoylamino)ethoxy]benzamide;

N-hydroxy-4-[2-(trans-3-indol-3-ylacryloylamino)ethoxy]benzamide;
N-hydroxy-4-{2-[trans-2-methylcinnamoyl amino]ethoxy}benzamide;
N-hydroxy-4-[2-(trans-2-hydroxycinnamoylamino)ethoxy]benzamide;
N-hydroxy-4-{2-[trans-3-(7-methoxybenzofuran-2-yl)acryloylamino]ethoxy}-benzamide;
N-hydroxy-4-{2R-[trans-3-(7-methoxybenzofuran-2-yl)acryloylamino]butoxy}-benzamide;
N-hydroxy-4-{2S-[trans-3-(5-methoxybenzofuran-2-yl)but-2-enoylamino]butoxy}-benzamide;
N-hydroxy-4-[2-(trans-3-furan-2-ylacryloylamino)ethoxy]benzamide; and
N-hydroxy-4-{2-[4-(4-(2-morpholin-4-ylethyl)thiazol-2-yl)phenylcarbonylamino]-ethoxy}-benzamide.

Compounds of Formula (I) where $R^1$ is hydrogen, $Ar^1$ is phenyl and $R^3$, $Ar^2$ and Y are as defined in Table II below are:

TABLE II

| Cpd # | $R^3$ | $Ar^2$ | Y |
|---|---|---|---|
| 1 | 2-HO-ethyl | trans phenyl-CH=CH— | —CH$_2$—CH$_2$— |
| 2 | phenyl | trans phenyl-CH=CH— | —CH$_2$—CH$_2$— |

TABLE II-continued

| Cpd # | $R^3$ | $Ar^2$ | Y |
|---|---|---|---|
| 3 | CH$_3$ | trans phenyl-CH=CH— | —CH$_2$—CH$_2$— |
| 4 | i-propyl | benzothiophen-2-yl | —CH$_2$—CH$_2$— |
| 5 | i-propyl | trans phenyl-CH=CH— | —CH$_2$—CH$_2$— |
| 6 | CH$_3$ | trans phenyl-CH=CH— | —CH$_2$—CH$_2$—CH$_2$— | and are named as:
N-hydroxy-4-(2-N-trans-cinnamoyl-N-hydroxyethylaminoethoxy)benzamide;
N-hydroxy-4-(2-N-trans-cinnamoyl-N-phenylaminoethoxy)benzamide;
N-hydroxy-4-(2-N-trans-cinnamoyl-N-methylaminoethoxy)benzamide;
N-hydroxy-4-(2-N-benzothiophen-2-yl-N-isopropylaminoethoxy)benzamide;
N-hydroxy-4-(2-N-trans-cinnamoyl-N-isopropylaminoethoxy)benzamide; and
N-hydroxy-4-(3-N-trans-cinnamoyl-N-methylaminopropoxy)benzamide.

Compounds of Formula (I) where $R^1$ and $R^3$ are hydrogen, $Ar^1$ is phenyl, $Ar^2$ and Y are as defined in Table III below are:

TABLE III

| Cpd # | Z | R | Y |
|---|---|---|---|
| 1 | S | H | —CH$_2$—CH$_2$— |
| 2 | O | H | —CH$_2$—CH$_2$— |
| 3 | NH | H | —CH$_2$—CH$_2$— |
| 4 | NMe | H | —CH$_2$—CH$_2$— |
| 5 | S | H | —CH$_2$—CH$_2$—CH$_2$— |
| 6 | O | H | —CH$_2$—CH$_2$—CH$_2$— |
| 7 | S | H | —(S)—CH(i-propyl)-CH$_2$— |
| 8 | S | H | —(S)—CH(ethyl)-CH$_2$— |
| 9 | S | H | —(S)—CH(methyl)-CH$_2$— |
| 10 | S | H | —(R)—CH(methyl)-CH$_2$— |
| 11 | O | H | —(S)—CH(ethyl)-CH$_2$— |
| 12 | S | H | —(R)—CH$_2$—CH(CH$_3$)— |
| 13 | S | H | —(S)—CH$_2$—CH(CH$_3$)— |
| 14 | O | H | —(R)—CH$_2$—CH(CH$_3$)— |
| 15 | S | 6-methoxy | —CH$_2$—CH$_2$— |
| 16 | S | 5-methyl | —CH$_2$—CH$_2$— |
| 17 | S | 3-chloro | —CH$_2$—CH$_2$— |
| 18 | O | 5-methyl | —CH$_2$—CH$_2$— |
| 19 | O | 6-methyl | —CH$_2$—CH$_2$— |
| 20 | S | 4-CF$_3$ | —CH$_2$—CH$_2$— |
| 21 | S | 5-fluoro | —CH$_2$—CH$_2$— |
| 22 | S | 5-methoxy | —CH$_2$—CH$_2$— |
| 23 | O | 5-chloro | —CH$_2$—CH$_2$— |
| 24 | O | 7-methoxy | —CH$_2$—CH$_2$— |
| 25 | O | 5-methoxy | —CH$_2$—CH$_2$— |
| 26 | O | 5-(2-methoxyethoxy)- | —CH$_2$—CH$_2$— |
| 27 | O | 5-(2-morpholin-4-ylethoxy)- | —CH$_2$—CH$_2$— |
| 28 | O | 5-pyridin-3-ylmethoxy- | —CH$_2$—CH$_2$— |
| 29 | O | 3-methyl | —CH$_2$—CH$_2$— |
| 30 | S | 3 methyl | —CH$_2$—CH$_2$— |
| 31 | O | 5-(2-hydroxyethoxy)- | —CH$_2$—CH$_2$— |

TABLE III-continued

| Cpd # | Z | R | Y |
|---|---|---|---|
| 32 | O | 5-(2-N,N-dimethylaminoethoxy)- | —CH₂—CH₂— |
| 33 | O | 6-CH₃OCH₂CH₂O | —CH₂—CH₂— |
| 34 | O | 6-(2-morpholin-4-ylethoxy)- | —CH₂—CH₂— |
| 35 | O | 6-pyridin-3ylmethoxy- | —CH₂—CH₂— |
| 36 | O | 3-ethyl | —CH₂—CH₂— |
| 37 | NH | 5-fluoro | —CH₂—CH₂— |
| 38 | NH | 5-methoxy | —CH₂—CH₂— |
| 39 | O | 3-CH₃OCH₂ | —CH₂—CH₂— |
| 40 | O | 3-phenoxymethyl | —CH₂—CH₂— |
| 41 | NH | 5,6-dimethoxy | —CH₂—CH₂— |
| 42 | O | 3-morpholino-4-ylmethyl | —CH₂—CH₂— |
| 43 | O | 3-N,N-dimethylaminomethyl | —CH₂—CH₂— |
| 44 | O | 3-i-propoxymethyl | —CH₂—CH₂— |
| 45 | O | 7-phenoxymethyl | —CH₂—CH₂— |
| 46 | O | 7-CH₃OCH₂ | —CH₂—CH₂— |
| 47 | O | 7-morpholino-4-ylmethyl | —CH₂—CH₂— |
| 48 | O | 7-N,N-dimethylaminomethyl | —CH₂—CH₂— |
| 49 | S | 5-methyl | —CH₂—CH₂—CH₂— |
| 50 | S | 6-methoxy | —CH₂—CH₂—CH₂— |
| 51 | O | 7-CH₃OCH₂ | —CH₂—CH₂—CH₂— |
| 52 | O | 7-phenoxymethyl | —CH₂—CH₂—CH₂— |
| 53 | O | 5-CH₃OCH₂CH₂O | —(R)—CH₂—CH(CH₃)— |
| 54 | O | H | (R)—CH(CH₃Smethyl)-CH₂— |
| 55 | O | H | (R)—CH(CH₃SO₂-methyl)-CH₂— |
| 56 | O | 3 -(2-phenylethyl)- | —CH₂—CH₂— |
| 57 | O | 3-(N-methyl-N-benzylaminomethyl)- | —CH₂—CH₂— |
| 58 | O | 3-(N-methyl-N-2-phenylethylamino-methyl)- | —CH₂—CH₂— |
| 59 | O | 3-(3-hydroxypropylthiomethyl)- | —CH₂—CH₂— |
| 60 | O | 3-(3-hydroxypropylsulfinyl-methyl)- | —CH₂—CH₂— |
| 61 | O | 3-(3-hydroxypropylsulfonyl-methyl)- | —CH₂—CH₂— |
| 62 | O | 3-(N-methyl-N-2-indol-3-yl-ethylaminomethyl)- | —CH₂—CH₂— |
| 63 | O | 3-[2-(3-trifluoromethyl-phenyl)ethyl]- | —CH₂—CH₂— |
| 64 | O | 3-[2-(3-trifluoromethoxy-phenyl)ethyl]- | —CH₂—CH₂— |
| 65 | O | 3-(N-hydroxyaminocarbonyl-methylaminomethyl)- | —CH₂—CH₂— |
| 66 | O | 3-(2-carboxyethylamino-methyl)- | —CH₂—CH₂— |
| 67 | O | H | (RS)—CH₂CH—(phenoxymethyl)- |
| 68 | O | 3-(3-hydroxypropyloxy-methyl)- | —CH₂—CH₂— |
| 69 | O | 3-(2-fluorophenoxymethyl)- | —CH₂—CH₂— |
| 70 | O | 3-(3-fluorophenoxymethyl)- | —CH₂—CH₂— |
| 71 | O | 3-(4-fluorophenoxymethyl)- | —CH₂—CH₂— |
| 72 | O | 3-(2-methoxyethyloxymethyl)- | —CH₂—CH₂— |
| 73 | O | 3-(pyridin-4-yloxymethyl)- | —CH₂—CH₂— |
| 74 | O | 3-(2,4,6-trifluorophenoxy-methyl)- | —CH₂—CH₂— |
| 75 | O | 3-(2-oxopyridin-1-ylmethyl)- | —CH₂—CH₂— |
| 76 | O | 3-(2,2,2-trifluoroethoxy-methyl)- | —CH₂—CH₂— |
| 77 | O | 3-(4-imidazol-1-ylphenoxy-methyl)- | —CH₂—CH₂— |
| 78 | O | 3-(4-[1.2.4]-triazin-1-yl-phenoxy-methyl)- | —CH₂—CH₂— |
| 79 | O | 3-(pyrrolidin-1-ylmethyl)- | —CH₂—CH₂— |
| 80 | O | 3-(piperidin-1-ylmethyl)- | —CH₂—CH₂— |
| 81 | O | 3-(4-trifluoromethylpiperidin-ylmethyl)- | —CH₂—CH₂— |
| 82 | O | 3-(4-methylpiperazin-1-yl-methyl)- | —CH₂—CH₂— |
| 83 | O | 3-(3,3,3-trifluoropropyloxy-methyl)- | —CH₂—CH₂— |
| 84 | O | 4-methyl | —CH₂—CH₂— |
| 85 | O | 3-(4-fluorophenylthiomethyl)- | —CH₂—CH₂— |
| 86 | O | 3-(4-fluorophenylsulfinyl-methyl)- | —CH₂—CH₂— |
| 87 | O | 3-(4-fluorophenylsulfonyl-methyl)- | —CH₂—CH₂— |
| 88 | O | 3-(2,2,2-trifluoroethoxy-methyl)- | (S)—CH(ethyl)-CH₂— |
| 89 | O | 4-hydroxy | —CH₂—CH₂— |
| 90 | O | 5-chloro | (S)—CH(ethyl)-CH₂— |
| 91 | O | 5-chloro | (R)—CH₂—CH(methyl)- |
| 92 | O | 4-pyridin-3-ylmethyloxy-methyl | —CH₂—CH₂— |

TABLE III-continued

| Cpd # | Z | R | Y |
|---|---|---|---|
| 93 | O | 4-methoxy | —CH$_2$—CH$_2$— |
| 94 | O | 4-(2-methoxyethyloxy)- | —CH$_2$—CH$_2$— |
| 95 | O | 4-pyridin-3-ylmethyloxy | —CH$_2$—CH$_2$— |
| 96 | NH | 4-methoxy | —CH$_2$—CH$_2$— |
| 97 | O | 3-(2-methoxyethyloxymethyl)- | (S)—CH(ethyl)-CH$_2$— |
| 98 | O | 3-(2-methoxyethyloxymethyl)- | (R)—CH$_2$—CH(methyl)- |
| 99 | O | 3-N,N-diethylaminomethyl | —CH$_2$—CH$_2$— |
| 100 | O | 5-(2-methoxyethyloxy)- | (S)—CH(ethyl)-CH$_2$— |
| 101 | O | 5-tetrahydropyran-4-yloxy | —CH$_2$—CH$_2$— |
| 102 | O | 5-tetrahydropyran-4-yloxy | (S)—CH(ethyl)-CH$_2$— |
| 103 | O | 5-tetrahydropyran-4-yloxy | (R)—CH$_2$—CH(methyl)- |
| 104 | O | 5-(2,2,2-trifluoroethyloxy)- | —CH$_2$—CH$_2$— |
| 105 | O | 5-(2-pyrrolidin-1-ylethyloxy)- | —CH$_2$—CH$_2$— |
| 106 | O | 5-(2-pyrrolidin-1-ylethyloxy)- | (S)—CH(ethyl)-CH$_2$— |
| 107 | O | 5-(2-pyrrolidin-1-ylethyloxy)- | (R)—CH$_2$—CH(methyl)- |
| 108 | O | 5-(piperidin-4-yloxy)- | —CH$_2$—CH$_2$— |
| 109 | O | H | (S)—CH(2-CH$_3$Sethyl)-CH$_2$— |
| 110 | O | H | (S)—CH(2-CH$_3$SO$_2$-ethyl)-CH$_2$— | and are named as:
N-hydroxy-4-[2-(benzothiophen-2-ylcarbonylamino)ethoxy]-benzamide;
N-hydroxy-4-[2-(benzofuran-2-ylcarbonylamino)ethoxy]-benzamide;
N-hydroxy-4-[2-(1H-indol-2-ylcarbonylamino)ethoxy]-benzamide;
N-hydroxy-4-[2-(1-methylindol-2-ylcarbonylamino)ethoxy]-benzamide;
N-hydroxy-4-[3-(benzothiophen-2-ylcarbonylamino)propoxy]-benzamide;
N-hydroxy-4-[3-(benzofuran-2-ylcarbonylamino)propoxy]-benzamide;
N-hydroxy-4-[2S-(benzothiophen-2-ylcarbonylamino)-3-methylbutoxy]-benzamide;
N-hydroxy-4-[2S-(benzothiophen-2-ylcarbonylamino)butoxy]-benzamide;
N-hydroxy-4-[2S-(benzothiophen-2-ylcarbonylamino)-propoxy]-benzamide;
N-hydroxy-4-[2R-(benzothiophen-2-ylcarbonylamino)-propoxy]-benzamide;
N-hydroxy-4-[2S-(benzofuran-2-ylcarbonylamino)butoxy]-benzamide;
N-hydroxy-4-[2-(benzothiophen-2-ylcarbonylamino)-1R-methylethoxy]-benzamide;
N-hydroxy-4-[2-(benzothiophen-2-ylcarbonylamino)-1S-methylethoxy]-benzamide;
N-hydroxy-4-[2-(benzofuran-2-ylcarbonylamino)-1R-methylethoxy]-benzamide;
N-hydroxy-4-[2-(6-methoxybenzothiophen-2-ylcarbonylamino)ethoxy]-benzamide;
N-hydroxy-4-[2-(5-methylbenzothiophen-2-ylcarbonylamino)ethoxy]-benzamide;
N-hydroxy-4-[2-(3-chlorobenzothiophen-2-ylcarbonylamino)ethoxy]-benzamide;
N-hydroxy-4-[2-(5-methylbenzofuran-2-ylcarbonylamino)ethoxy]-benzamide;
N-hydroxy-4-[2-(6-methylbenzofuran-2-ylcarbonylamino)ethoxy]-benzamide;
N-hydroxy-4-[2-(4-trifluoromethylbenzothiophen-2-ylcarbonylamino)ethoxy]-benzamide;
N-hydroxy-4-[2-(5-fluorobenzothiophen-2-ylcarbonylamino)ethoxy]-benzamide;
N-hydroxy-4-[2-(5-methoxybenzothiophen-2-ylcarbonylamino)ethoxy]-benzamide;
N-hydroxy-4-[2-(5-chlorobenzofuran-2-ylcarbonylamino)ethoxy]-benzamide;
N-hydroxy-4-[2-(7-methoxybenzofuran-2-ylcarbonylamino)ethoxy]-benzamide;
N-hydroxy-4-[2-(5-methoxybenzofuran-2-ylcarbonylamino)ethoxy]-benzamide;
N-hydroxy-4-{2-[5-(2-methoxyethoxy)benzofuran-2-ylcarbonylamino]ethoxy}benzamide;
N-hydroxy-4-{2-[5-(2-morpholin-4-ylethoxy)benzofuran-2-ylcarbonylamino]ethoxy}-benzamide;
N-hydroxy-4-{2-[5-(pyridin-3-ylmethoxy)benzofuran-2-ylcarbonylamino]ethoxy}-benzamide;
N-hydroxy-4-[2-(3-methylbenzofuran-2-ylcarbonylamino)ethoxy]-benzamide;
N-hydroxy-4-[2-(3-methylbenzothiophen-2-ylcarbonylamino)ethoxy]-benzamide;
N-hydroxy-4-{2-[5-(2-hydroxyethoxy)benzofuran-2-ylcarbonylamino]ethoxy}benzamide;
N-hydroxy-4-{2-[5-(2-N,N-dimethylaminoethoxy)benzofuran-2-ylcarbonylamino]-ethoxy}-benzamide;
N-hydroxy-4-{2-[6-(2-methoxyethoxy)benzofuran-2-ylcarbonylamino]ethoxy}-benzamide;
N-hydroxy-4-{2-[6-(2-morpholin-4-ylethoxy)benzofuran-2-ylcarbonylamino]ethoxy}-benzamide;
N-hydroxy-4-{2-[6-(pyridin-3-ylmethoxy)benzofuran-2-ylcarbonylamino]ethoxy}-benzamide;
N-hydroxy-4-[2-(3-ethylbenzofuran-2-ylcarbonylamino)ethoxy]-benzamide;
N-hydroxy-4-[2-(5-fluoroindol-2-ylcarbonylamino)ethoxy]-benzamide;

N-hydroxy-4-[2-(5-methoxyindol-2-ylcarbonylamino)ethoxy]-benzamide;
N-hydroxy-4-{2-[3-(methoxymethyl)benzofuran-2-ylcarbonylamino]ethoxy}benzamide;
N-hydroxy-4-{2-[3-(phenoxymethyl)benzofuran-2-ylcarbonylamino]ethoxy}-benzamide;
N-hydroxy-4-[2-(5,6-dimethoxyindol-2-ylcarbonylamino)ethoxy]-benzamide;
N-hydroxy-4-{2-[3-morpholin-4-ylmethyl)benzofuran-2-ylcarbonylamino]ethoxy}-benzamide;
N-hydroxy-4-{2-[3-(N,N-dimethylaminomethyl)benzofuran-2-ylcarbonylamino]-ethoxy}-benzamide;
N-hydroxy-4-{2-[3-(i-propoxymethyl)benzofuran-2-ylcarbonylamino]ethoxy}-benzamide;
N-hydroxy-4-{2-[7-(phenoxymethyl)benzofuran-2-ylcarbonylamino]ethoxy}-benzamide;
N-hydroxy-4-{2-[7-(methoxymethyl)benzofuran-2-ylcarbonylamino]ethoxy}-benzamide;
N-hydroxy-4-{2-[7-(morpholin-4-ylmethyl)benzofuran-2-ylcarbonylamino]ethoxy}-benzamide;
N-hydroxy-4-{2-[7-(N,N-dimethylaminomethyl)benzofuran-2-ylcarbonylamino]-ethoxy}-benzamide;
N-hydroxy-4-{3-[5-(methyl)benzothiophen-2-ylcarbonylamino]propoxy}-benzamide;
N-hydroxy-4-{3-[6-(methoxy)benzothiophen-2-ylcarbonylamino]propoxy}-benzamide;
N-hydroxy-4-{3-[7-(methoxymethyl)benzofuran-2-ylcarbonylamino]propoxy}-benzamide;
N-hydroxy-4-{3-[7-(phenoxymethyl)benzofuran-2-ylcarbonylamino]propoxy}-benzamide;
N-hydroxy-4-{2-[5-(2-methoxyethoxy)benzofuran-2-ylcarbonylamino]-1R-methyl ethoxy}benzamide.
N-hydroxy-4-(2R-benzofuran-2-ylcarbonylamino-3-methylthiopropoxy)benzamide;
N-hydroxy-4-(2R-benzofuran-2-ylcarbonylamino-3-methylsulfonylpropoxy)benzamide;
N-hydroxy-4-{2-[3-(2-phenylethyl)benzofuran-2-ylcarbonylamino]ethoxy}benzamide;
N-hydroxy-4-{2-[3-(N-methyl-N-benzylaminomethyl)benzofuran-2-ylcarbonylamino]-ethoxy}benzamide;
N-hydroxy-4-{2-[3-(N-methyl-N-2-phenylethylaminomethyl)benzofuran-2-ylcarbonylamino]-ethoxy}benzamide;
N-hydroxy-4-{2-[3-(3-hydroxypropylthiomethyl)benzofuran-2-ylcarbonylamino]-ethoxy}benzamide;
N-hydroxy-4-{2-[3-(3-hydroxypropylsulfinylmethyl)benzofuran-2-ylcarbonylamino]-ethoxy}benzamide;
N-hydroxy-4-{2-[3-(3-hydroxypropylsulfonylmethyl)benzofuran-2-ylcarbonylamino]-ethoxy}benzamide;
N-hydroxy-4-{2-[3-(N-methyl-N-2-indol-3-ylethylaminomethyl)benzofuran-2-ylcarbonylamino]-ethoxy}benzamide;
N-hydroxy-4-{2-[3-(2-(3-trifluoromethylphenyl)ethyl)benzofuran-2-ylcarbonylamino]-ethoxy}benzamide;
N-hydroxy-4-{2-[3-(2-(3-trifluoromethoxyphenyl)ethyl)benzofuran-2-ylcarbonylamino]-ethoxy}benzamide;
N-hydroxy-4-{2-[3-(N-hydroxyaminocarbonylmethylaminomethyl)benzofuran-2-ylcarbonylamino]ethoxy}benzamide;
N-hydroxy-4-{2-[3-(2-carboxyethylaminomethy)benzofuran-2-ylcarbonylamino]-ethoxy}benzamide; and
N-hydroxy-4-{2-(benzofuran-2-ylcarbonylamino)-1RS-phenoxymethylethoxy}-benzamide.
N-hydroxy-4-{2-[3-(3-hydroxypropoxymethyl)benzofuran-2-ylcarbonylamino]-ethoxy}-benzamide;
N-hydroxy-4-{2-[3-(2-fluorophenoxymethyl)benzofuran-2-ylcarbonylamino]ethoxy}-benzamide;
N-hydroxy-4-{2-[3-(3-fluorophenoxymethyl)benzofuran-2-ylcarbonylamino]ethoxy}-benzamide;
N-hydroxy-4-{2-[3-(4-fluorophenoxymethyl)benzofuran-2-ylcarbonylamino]ethoxy}-benzamide;
N-hydroxy-4-{2-[3-(2-methoxyethyloxymethyl)benzofuran-2-ylcarbonylamino]-ethoxy}-benzamide;
N-hydroxy-4-{2-[3-(pyridin-4-yloxymethyl)benzofuran-2-ylcarbonylamino]ethoxy}-benzamide;
N-hydroxy-4-{2-[3-(2,4,6-trifluorophenoxymethyl)benzofuran-2-ylcarbonylamino]-ethoxy}benzamide;
N-hydroxy-4-{2-[3-(2-oxopyridin-1-ylmethyl)benzofuran-2-ylcarbonylamino]ethoxy}-benzamide;
N-hydroxy-4-{2-[3-(2,2,2-trifluoroethoxymethyl)benzofuran-2-ylcarbonylamino]-ethoxy}benzamide;
N-hydroxy-4-{2-[3-(4-imidazol-1-ylphenoxymethyl)benzofuran-2-ylcarbonylamino]-ethoxy}benzamide;
N-hydroxy-4-{2-[3-(4-[1.2.4]-triazin-1-ylphenoxymethyl)benzofuran-2-ylcarbonylamino]ethoxy}benzamide;
N-hydroxy-4-{2-[3-(pyrrolidin-1-methyl)benzofuran-2-ylcarbonylamino]ethoxy}-benzamide;
N-hydroxy-4-{2-[3-(piperidin-1-methyl)benzofuran-2-ylcarbonylamino]ethoxy}-benzamide;
N-hydroxy-4-{2-[3-(4-trifluoromethylpiperidin-1-methyl)benzofuran-2-ylcarbonylamino]ethoxy}benzamide;
N-hydroxy-4-{2-[3-(4-methylpiperazin-1-methyl)benzofuran-2-ylcarbonylamino]-ethoxy}benzamide;
N-hydroxy-4-{2-[3-(3,3,3-trifluoropropyloxymethyl)benzofuran-2-ylcarbonylamino]-ethoxy}benzamide;
N-hydroxy-4-[2-(4-methylbenzofuran-2-ylcarbonylamino)ethoxy]benzamide;
N-hydroxy-4-{2-[3-(4-fluorophenylthiomethyl)benzofuran-2-ylcarbonylamino]-ethoxy}-benzamide;
N-hydroxy-4-{2-[3-(4-fluorophenylsulfinylmethyl)benzofuran-2-ylcarbonylamino]-ethoxy}benzamide;
N-hydroxy-4-{2-[3-(4-fluorophenylsulfonylmethyl)benzofuran-2-ylcarbonylamino]-ethoxy}benzamide;
N-hydroxy-4-{2S-[3-(2,2,2-trifluoroethoxymethyl)benzofuran-2-ylcarbonylamino]-butoxy}benzamide;
N-hydroxy-4-[2-(4-hydroxybenzofuran-2-ylcarbonylamino)ethoxy]benzamide;
N-hydroxy-4-[2S-(5-chlorobenzofuran-2-ylcarbonylamino)butoxy]benzamide;
N-hydroxy-4-[2-(5-chlorobenzofuran-2-ylcarbonylamino)-1R-methylethoxy]-benzamide;
N-hydroxy-4-[2-(4-pyridin-3-ylmethyloxymethylbenzofuran-2-ylcarbonylamino)ethoxy]benzamide;
N-hydroxy-4-[2-(4-methoxybenzofuran-2-ylcarbonylamino)ethoxy]benzamide;
N-hydroxy-4-{2-[4-(2-methoxyethyloxy)benzofuran-2-ylcarbonylamino)ethoxy}-benzamide;
N-hydroxy-4-[2-(4-pyridin-3-ylmethyloxybenzofuran-2-ylcarbonylamino)ethoxy]benzamide;
N-hydroxy-4-[2-(4-methoxyindol-2-ylcarbonylamino)ethoxy]benzamide;
N-hydroxy-4-{2S-[3-(2-methoxyethyloxymethyl)benzofuran-2-ylcarbonylamino]-butoxy}-benzamide;
N-hydroxy-4-{2-[3-(2-methoxyethyloxymethyl)benzofuran-2-ylcarbonylamino]-1R-methyl-ethoxy}benzamide;
N-hydroxy-4-{2-[3-(N,N-diethylaminomethyl)benzofuran-2-ylcarbonylamino]ethoxy}-benzamide;
N-hydroxy-4-{2S-[5-(2-methoxyethyloxy)benzofuran-2-ylcarbonylamino]butoxy}-benzamide;
N-hydroxy-4-{2-[5-(tetrahydropyran-4-yloxy)benzofuran-2-ylcarbonylamino]ethoxy}-benzamide;
N-hydroxy-4-{2S-[5-(tetrahydropyran-4-yloxy)benzofuran-2-ylcarbonylamino]-butoxy}-benzamide;

N-hydroxy-4-{2-[5-(tetrahydropyran-4-yloxy)benzofuran-2-ylcarbonylamino]-1R-methyl-ethoxy}benzamide;
N-hydroxy-4-{2-[5-(2,2,2-trifluoroethyloxy)benzofuran-2-ylcarbonylamino]ethoxy}-benzamide;
N-hydroxy-4-{2-[5-(2-pyrrolidin-1-ylethyloxy)benzofuran-2-ylcarbonylamino]-ethoxy}-benzamide;
N-hydroxy-4-{2S-[5-(2-pyrrolidin-1-ylethyloxy)benzofuran-2-ylcarbonylamino]-butoxy}-benzamide;
N-hydroxy-4-{2-[5-(2-pyrrolidin-1-ylethyloxy)benzofuran-2-ylcarbonylamino]-1R-methyl-ethoxy}benzamide;
N-hydroxy-4-{2-[5-(piperidin-4-yloxy)benzofuran-2-ylcarbonylamino]ethoxy}-benzamide;
N-hydroxy-4-[2S-(benzofuran-2-ylcarbonylamino)-4-methylthiobutoxy]benzamide; and
N-hydroxy-4-[2S-(benzofuran-2-ylcarbonylamino)-4-methylsulfonylbutoxy]benzamide.

Compounds of Formula (I) where $R^1$ and $R^3$ are hydrogen, $Ar^1$ is isoxazol-5-yl and $Ar^2$ and Y are as defined in Table IV below are:

TABLE IV

Ar²—CONH—Y—O—[isoxazole ring]—C(=O)—NH—OH

| Cpd # | Ar² | Y |
|---|---|---|
| 1 | 4-biphenyl | (R)—CH₂—CH(CH₃)— |
| 2 | 4-biphenyl | (S)—CH(ethyl)-CH₂— |
| 3 | benzofuran-2-yl | —CH₂—CH₂— |
| 4 | trans phenyl-CH=CH— | —CH₂—CH₂— |
| 5 | 4-(2-ethoxyphenyl)phenyl | —CH₂—CH₂—CH₂— |
| 6 | 3-biphenyl | —CH₂—CH₂—CH₂— |
| 7 | 4-biphenyl | —CH₂—CH₂—CH₂— |
| 8 | naphth-2-yl | —CH₂—CH₂— |
| 9 | 3-methylbiphen-4-yl | —CH₂—CH₂— |
| 10 | 2'-ethoxybiphen-4-yl | —CH₂—CH₂— |
| 11 | 3-methylbiphen-4-yl | —CH₂—CH₂—CH₂— |
| 12 | 4-phenylthiazol-2-yl | —CH₂—CH₂—CH₂— |
| 13 | naphth-2-yl | —CH₂—CH₂—CH₂— |
| 14 | naphth-1-yl | —CH₂—CH₂—CH₂— |
| 15 | 2-(2-phenylethyl)phenyl | —CH₂—CH₂—CH₂— |
| 16 | naphth-1-yl | —CH₂—CH₂— |
| 17 | benzofuran-2-yl | (S)—CH(ethyl)-CH₂— |
| 18 | 3-biphenyl | (S)—CH(ethyl)-CH₂— |
| 19 | benzofuran-2-yl | (R)—CH₂—CH(methyl)- |
| 20 | 3-biphenyl | (R)—CH₂—CH(methyl)- |
| 21 | 3-biphenyl | —CH₂—CH₂— |
| 22 | 4-biphenyl | —CH₂—CH₂— |
| 23 | 4-phenylthiazol-2-yl | —CH₂—CH₂— |
| 24 | 2-(2-phenylethyl)phenyl | —CH₂—CH₂— |
| 25 | 2-biphenyl | —CH₂—CH₂— |
| 26 | 2-biphenyl | —CH₂—CH₂—CH₂— |
| 27 | naphth-2-yl | (S)—CH(ethyl)-CH₂— |
| 28 | naphth-1-yl | (S)—CH(ethyl)-CH₂— |
| 29 | naphth-2-yl | (R)—CH₂—CH(methyl)- |
| 30 | naphth-1-yl | (R)—CH₂—CH(methyl)- |
| 31 | benzofuran-2-yl | —CH₂—CH₂—CH₂— |
| 32 | trans phenylCH=CH— | —CH₂—CH₂—CH₂— |
| 33 | 3-(phenoxymethyl)benzofuran-2-yl | —CH₂—CH₂— | and are named as:
N-hydroxy-3-[2-(biphen-4-ylcarbonylamino)-1R-methyl-ethoxy]isoxazol-5-ylcarboxamide;
N-hydroxy-3-[2S-(biphen-4-ylcarbonylamino)butoxy]isoxazol-5-ylcarboxamide;
N-hydroxy-3-[2-(benzofuran-2-ylcarbonylamino)ethoxy]isoxazol-5-ylcarboxamide;
N-hydroxy-3-[2-(trans-cinnamoylamino)ethoxy]isoxazol-5-ylcarboxamide;
N-hydroxy-3-[3-(4-(2-ethoxyphenyl)phenylcarbonylamino)propoxy]isoxazol-5-ylcarboxamide;
N-hydroxy-3-[3-(biphen-3-ylcarbonylamino)propoxy]isoxazol-5-ylcarboxamide;
N-hydroxy-3-[3-(biphen-4-ylcarbonylamino)propoxy]isoxazol-5-ylcarboxamide;
N-hydroxy-3-[2-(naphth-2-ylcarbonylamino)ethoxy] isoxazol-5-ylcarboxamide;
N-hydroxy-3-[2-(3-methylbiphen-4-ylcarbonylamino)ethoxy]isoxazol-5-ylcarboxamide;
N-hydroxy-3-[2-(2'-ethoxybiphen-4-ylcarbonylamino)ethoxy]isoxazol-5-ylcarboxamide;
N-hydroxy-3-[3-(3-methylbiphen-4-ylcarbonylamino)propoxy]isoxazol-5-ylcarboxamide;
N-hydroxy-3-[3-(4-phenylthiazol-2-ylcarbonylamino)propoxy]isoxazol-5-ylcarboxamide;
N-hydroxy-3-[3-(naphth-2-ylcarbonylamino)propoxy]isoxazol-5-ylcarboxamide;
N-hydroxy-3-[3-(naphth-1-ylcarbonylamino)propoxy]isoxazol-5-ylcarboxamide;
N-hydroxy-3-{3-[2-(2-phenylethyl)phenylcarbonylamino]propoxy}isoxazol-5-ylcarboxamide;
N-hydroxy-3-[2-(naphth-1-ylcarbonylamino)ethoxy]isoxazol-5-ylcarboxamide;
N-hydroxy-3-[2S-(benzofuran-2-ylcarbonylamino)butoxy] isoxazol-5-ylcarboxamide;
N-hydroxy-3-[2S-(biphen-3-ylcarbonylamino)butoxy]isoxazol-5-ylcarboxamide;
N-hydroxy-3-[2-(benzofuran-2-ylcarbonylamino)-1R-methylethoxy]isoxazol-5-ylcarboxamide;
N-hydroxy-3-[2-(biphen-3-ylcarbonylamino)-1R-methyl-ethoxy]isoxazol-5-ylcarboxamide;
N-hydroxy-3-[2-(biphen-3-ylcarbonylamino)ethoxy]isoxazol-5-ylcarboxamide;
N-hydroxy-3-[2-(biphen-4-ylcarbonylamino)ethoxy]isoxazol-5-ylcarboxamide;
N-hydroxy-3-[2-(4-phenylthiazol-2-ylcarbonylamino)ethoxy]isoxazol-5-ylcarboxamide;
N-hydroxy-3-{2-[2-(2-phenylethyl)phenylcarbonylamino]ethoxy} isoxazol-5-ylcarboxamide;
N-hydroxy-3-[2-(biphen-2-ylcarbonylamino)ethoxy]isoxazol-5-ylcarboxamide;
N-hydroxy-3-[3-(biphen-2-ylcarbonylamino)propoxy]isoxazol-5-ylcarboxamide;
N-hydroxy-3-[2S-(naphth-2-ylcarbonylamino)butoxy]isoxazol-5-ylcarboxamide;
N-hydroxy-3-[2S-(naphth-1-ylcarbonylamino)butoxy]isoxazol-5-ylcarboxamide;
N-hydroxy-3-[2-(naphth-2-ylcarbonylamino)-1R-methyl-ethoxy] isoxazol-5-ylcarboxamide;
N-hydroxy-3-[2-(naphth-1-ylcarbonylamino)-1R-methyl-ethoxy]isoxazol-5-ylcarboxamide;
N-hydroxy-3-[3-(benzofuran-2-ylcarbonylamino)propoxy] isoxazol-5-ylcarboxamide;
N-hydroxy-3-[3-(trans-cinnamoylamino)propoxy]isoxazol-5-ylcarboxamide; and
N-hydroxy-3-[2-(3-phenoxymethylbenzofuran-2-ylcarbonylamino)ethoxy]isoxazol-5-yl-carboxamide.

Preferred Embodiments

While the broadest definition of this invention is set forth in the Summary of the Invention, certain compounds of Formula (I) are preferred. For example:

I. A preferred group of compounds of Formula (I) is that wherein:

$R^1$ is hydrogen or alkyl;

X is —O—, —$NR^2$—, or —S(O)$_n$ where n is 0-2 and $R^2$ is hydrogen or alkyl;

Y is alkylene optionally substituted with cycloalkyl, optionally substituted phenyl, alkylthio, alkysulfonyl, optionally substituted phenylalkylthio, optionally substituted phenylalkylsulfonyl, or hydroxy;

$Ar^1$ is phenylene or heteroarylene wherein said $Ar^1$ is optionally substituted with one or two groups independently selected from alkyl, halo, hydroxy, alkoxy, haloalkoxy, or haloalkyl;

$R^3$ is hydrogen, alkyl, hydroxyalkyl, or optionally substituted phenyl; and $Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl;

wherein the terms aryl, heteroaryl, heterocycloalkyl, optionally substituted phenyl, optionally substituted heteroaryl, optionally substituted heterocycloalkyl, and aminoalkyl either alone or as part of another term (e.g., aralkyl, optionally substituted phenylalkylthio, aminoalkoxy, optionally substituted phenylcarbonylamino, optionally substituted heteroaryl, etc) contained within the scope of preferred Group I above, have the meaning given below:

"aryl" means a monovalent monocyclic or bicyclic aromatic hydrocarbon radical of 6 to 12 ring atoms e.g., phenyl, naphthyl or anthracenyl optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted heteroaryl, cycloalkyloxy, cycloalkenyloxy, optionally substituted phenylcarbonylamino, optionally substituted heteroaryloxy, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—$R^a$ (where n is 0 to 2 and $R^a$ is alkyl, haloalkyl, optionally substituted phenyl, optionally substituted phenylalkyl, optionally substituted heteroaryl, or optionally substituted heteroaralkyl), -alkylene-NHSO$_2$—$R^b$ (where $R^b$ is alkyl, haloalkyl, optionally substituted phenyl, optionally substituted phenylalkyl, optionally substituted heteroaryl, optionally substituted heteroaralkyl, or optionally substituted heterocycloalkyl), or -alkylene-NHCO—$R^c$ (where $R^c$ is alkyl, haloalkyl, optionally substituted phenyl, optionally substituted phenylalkyl, optionally substituted heteroaryl, optionally substituted heteroaralkyl, or optionally substituted heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. More preferably, the aryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, optionally substituted phenyl, optionally substituted phenylalkyl, optionally substituted heteroaryl, cycloalkyloxy, cycloalkenyloxy, optionally substituted phenylcarbonylamino, optionally substituted heteroaryl, optionally substituted heteroaralkyloxy, aminoalkyl, aminoalkoxy, alkoxyalkyl, alkoxyalkyloxy, methylenedioxy, optionally substituted phenyloxyalkyl, optionally substituted heteroaryloxyalkyl, optionally substituted heterocycloalkylalkyl, optionally substituted heterocycloalkylalkyloxy, optionally substituted heterocycloalkyloxyalkyl, or optionally substituted heterocycloalkyloxy. Preferably, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl;

"heterocycloalkyl" means a saturated monovalent cyclic group of 3 to 8 ring atoms in which one or two ring atoms are heteroatoms selected from N, O, or S(O)$_n$, where n is an integer from 0 to 2, the remaining ring atoms being C. More specifically the term heterocycloalkyl includes, but is not limited to, pyrrolidino, piperidino, morpholino, piperazino, tetrahydropyranyl, and thiomorpholino, and the derivatives thereof (formed when the heterocycloalkyl ring is substituted with a substituent listed below); or an N-oxide or a protected derivative thereof. The heterocycloalkyl is optionally fused to aryl and is optionally substituted with one, two, or three substituents independently selected from alkyl, alkoxy, halo, haloalkyl, haloalkoxy, hydroxy, amino, alkylamino, dialkylamino, hydroxyalkyl, hydroxyalkyloxy, optionally substituted phenyl, optionally substituted heteroaryl, cycloalkyloxy, cycloalkenyloxy, optionally substituted phenylcarbonylamino, optionally substituted heteroaryl, optionally substituted heteroaralkyloxy, aminoalkyl, aminoalkoxy, alkoxyalkyl, alkoxyalkyloxy, methylenedioxy, optionally substituted phenyloxyalkyl, optionally substituted heterocycloalkylalkyl, optionally substituted heterocycloalkylalkyloxy, or optionally substituted heterocycloalkyloxy. Preferably, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl;

"heteroaryl" means a monovalent monocyclic or bicyclic aromatic radical of 5 to 10 ring atoms containing one or more, preferably one, two, or three ring heteroatoms selected from N, O, or S, the remaining ring atoms being carbon. More specifically the term heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isoxazolyl, benzoxazolyl, benzothiophenyl, benzthiazolyl, quinolinyl, isoquinolinyl, benzopyranyl, and thiazolyl, and the derivatives thereof (formed when the heteroaryl ring is substituted with a substituent listed below), or an N-oxide or a protected derivative thereof. The heteroaryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted heteroaryl, cycloalkyloxy, cycloalkenyloxy, optionally substituted phenylcarbonylamino, optionally substituted heteroaryl, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—R$^a$ (where n is 0 to 2 and R$^a$ is alkyl, haloalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, optionally substituted heteroaralkyl, or optionally substituted heterocycloalkyl), or -alkylene-NHCO—R$^c$ (where R$^c$ is alkyl, haloalkyl, optionally substituted phenyl, optionally substituted phenylalkyl, optionally substituted heteroaryl, optionally substituted heteroaralkyl, or optionally substituted heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. More preferably, the substituents are independently selected from alkyl, alkoxy, halo, haloalkyl, haloalkoxy, amino, alkylamino, dialkylamino, hydroxy, hydroxyalkyl, hydroxyalkyloxy, optionally substituted phenyl, optionally substituted heteroaryl, cycloalkyloxy, cycloalkenyloxy, optionally substituted phenylcarbonylamino, optionally substituted heteroaryl, optionally substituted heteroaralkyloxy, aminoalkyl, aminoalkoxy, alkoxyalkyl, alkoxyalkyloxy, methylenedioxy, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, or optionally substituted heterocycloalkyloxy. Preferably, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl;

"optionally substituted phenyl" means a phenyl ring optionally substituted with one, two, or three substituents independently selected from alkyl, halo, alkoxy, alkylthio, haloalkyl, haloalkoxy, heteroaryl (that is optionally substituted with one or two substituents independently selected from alkyl, halo, hydroxy, alkoxy, carboxy, amino, alkylamino, or dialkylamino), heterocycloalkyl (that is optionally substituted with one or two substituents independently selected from alkyl, halo, hydroxy, alkoxy, carboxy, amino, alkylamino, or dialkylamino), amino, alkylamino, dialkylamino, hydroxy, cyano, nitro, methylenedioxy, aminocarbonyl, hydroxyalkyl, alkoxycarbonyl, aminoalkyl, or carboxy or optionally substituted with five fluorine atoms. More preferably, the substituents are independently selected from alkyl, halo, alkoxy, alkylthio, trifluoromethyl, trifluoromethoxy, amino, alkylamino, dialkylamino, hydroxy, cyano, nitro, methylenedioxy, aminocarbonyl, hydroxyalkyl, alkoxycarbonyl, aminoalkyl, or carboxy or optionally substituted with five fluorine atoms;

"optionally substituted heteroaryl" means a monovalent monocyclic or bicyclic aromatic radical of 5 to 10 ring atoms containing one or more, preferably one, two, or three ring heteroatoms selected from N, O, or S, the remaining ring atoms being carbon which is optionally substituted with one, two, or three substituents independently selected from alkyl, halo, alkoxy, trifluoromethyl, trifluoromethoxy, amino, alkylamino, dialkylamino, hydroxy, cyano, nitro, aminocarbonyl, hydroxyalkyl, alkoxycarbonyl, aminoalkyl, optionally substituted phenyl, optionally substituted phenoxy, carboxy, or heteroaryl that is optionally substituted with alkyl, halo, hydroxy, alkoxy, carboxy, amino, alkylamino, or dialkylamino. More specifically the term optionally substituted heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isoxazolyl, benzoxazolyl, quinolinyl, isoquinolinyl, benzopyranyl, and thiazolyl, and the derivatives thereof (formed when the heteroaryl ring is substituted with a substituent listed below), or an N-oxide or a protected derivative thereof;

"optionally substituted heterocycloalkyl" a saturated monovalent cyclic group of 3 to 8 ring atoms in which one or two ring atoms are heteroatoms selected from N, O, or S(O)$_n$, where n is an integer from 0 to 2, the remaining ring atoms being C. The heterocycloalkyl is optionally fused to aryl and is optionally substituted with one, two, or three substituents independently selected from alkyl, halo, alkoxy, trifluoromethyl, trifluoromethoxy, amino, alkylamino, dialkylamino, hydroxy, cyano, nitro, optionally substituted phenylalkyl, optionally substituted heteroalkyl, aminocarbonyl, hydroxyalkyl, alkoxycarbonyl, aminoalkyl, or carboxy. More specifically the term heterocycloalkyl includes, but is not limited to, pyrrolidino, piperidino, morpholino, piperazino, tetrahydropyranyl, and thiomorpholino, and the derivatives thereof (formed when the heterocycloalkyl ring is substituted with a substituent listed below); or an N-oxide or a protected derivative thereof; and "aminoalkyl" means a linear monovalent hydrocarbon radical of two to six carbon atoms or a branched monovalent hydrocarbon radical of three to six carbons substituted with at least one, preferably one or two, —NRR' where R and R' are independently selected from hydrogen, alkyl, or —COR$^a$ where R$^a$ is alkyl, or an N-oxide derivative, or a protected derivative e.g., aminomethyl, methylaminoethyl, 2-ethylamino-2-methylethyl, 1,3-diaminopropyl, dimethylaminomethyl, diethylaminoethyl, acetylaminopropyl, and the like; and the other terms contained within the scope of preferred Group I are as defined in the definition section of this Application.

Within this group I:

(A). A preferred group of compounds is that wherein R$^1$ and R$^3$ are hydrogen, X is —O— and Y is ethylene or n-propylene, preferably ethylene.

(B). Another preferred group of compounds is that wherein R$^1$ and R$^3$ are hydrogen, X is —O— and Y is —CH(C$_2$H$_5$)CH$_2$—, —CH(i-C$_3$H$_7$)CH$_2$—, or CH(CH$_3$)CH$_2$— and the stereochemistry at the chiral carbon is (S). More preferably, Y is —CH(C$_2$H$_5$)CH$_2$—.

(C). Yet another preferred group of compounds is that wherein R$^1$ and R$^3$ are hydrogen, X is —O— and Y is CH$_2$CH(CH$_3$)— and the stereochemistry at the chiral carbon is (R).

(i) Within the groups (A)-(C), a more preferred group of compounds is that wherein Ar$^1$ is phenylene in which the hydroxamate and the X group are para to each other and Ar$^2$ is aryl. Preferably Ar$^2$ is phenyl and is optionally substituted with one or two substituents independently selected from methoxy, ethoxy, phenyl, methyl, tert-butyl, pyrrol-1-yl, cyclohexene-3-oxy, pyridin-3-yl, pyridin-2-yl, benzoylamino, fluoro, chloro, or thiophen-2-ylmethoxy. More preferably, Ar$^2$ is phenyl, 4-biphenyl, 3-biphenyl, 4-tert-butylphenyl, 4-pyrrol-1-ylphenyl, 4-(cyclohexene-3-oxy)phenyl, 4-(pyridin-2-yl)phenyl, 4-(pyridin-3-yl)phenyl, 2,4-difluorophenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro-4-methoxyphenyl, 2-thiophen-2-ylmethoxyphenyl, 3-thiophen-2-ylmethoxyphenyl, 2-biphenyl, or 2-pyrrol-1-ylphenyl.

(ii) Within the groups (A)-(C), another more preferred group of compounds is that wherein $Ar^1$ is phenylene in which the hydroxamate and the X group are para to each other and $Ar^2$ is trans aryl-CH=CH—. Preferably $Ar^2$ is trans phenyl-CH=CH— and is optionally substituted with alkoxy, preferably methoxy. Preferably, $Ar^2$ is trans phenyl-CH=CH—.

(iii) Within the groups (A)-(C), another more preferred group of compounds is that wherein $Ar^1$ is phenylene in which the hydroxamate and the X group are para to each other and $Ar^2$ is heteroaryl-CH=CH—. Preferably $Ar^2$ is pyridinyl-CH=CH—. Preferably, $Ar^2$ is trans 5-bromothiophen-2-yl-CH=CH— or trans indol-3-yl-CH=CH—.

(iv) Within the groups (A)-(C), another more preferred group of compounds is that wherein $Ar^1$ is phenylene in which the hydroxamate and the X group are para to each other and $Ar^2$ is heteroaryl. Preferably $Ar^2$ is pyridin-3-yl, thiophen-2-yl, quinolin-6-yl, thiazol-2-yl, benzthiazol-2-yl, benzoxazol-2-yl, furanyl, pyrrol-2-yl, indol-5-yl, indol-3-yl, indazol-3-yl, quinolin-3-yl, quinolin-1-yl, quinolin-8-yl, benzotriazol-4-yl, benzofuran-5-yl, isoquinolin-1-yl, isoquinolin-3-yl, quinoxalin-2-yl, quinolin-2-yl, or benzimidazol-5-yl wherein said rings are optionally substituted with phenyl, pyridin-4-yl, methyl, methoxy, or dimethylaminomethyl.

(v) Within the groups (A)-(C), another more preferred group of compounds is that wherein $Ar^1$ is phenylene in which the hydroxamate and the X group are para to each other and $Ar^2$ is indol-2-yl, benzofuran-2-yl or benzothiophen-2-yl which are optionally substituted with alkyl, alkoxy, halo, haloalkyl, alkoxyalkyloxy, optionally substituted heterocycloalkylalkyloxy, optionally substituted heteroaralkyloxy, hydroxyalkoxy, aminoalkyl, aminoalkyloxy, alkoxyalkyloxy, alkoxyalkyl, optionally substituted phenyloxyalkyl, or optionally substituted heterocycloalkylalkyl. Preferably, $Ar^2$ is benzofuran-2-yl or benzothiophen-2-yl wherein benzofuran-2-yl or benzothiophen-2-yl is optionally substituted with methoxy, methyl, chloro, trifluoromethyl, fluoro, 2-methoxyethoxy, 2-morpholin-4-ylethoxy, pyridin-3-ylmethoxy, 2-hydroxyethoxy, 2-N,N-dimethylaminoethoxy, ethyl, methoxymethyl, 2-propyloxymethyl, phenoxymethyl, morpholin-4-ylmethyl, or N,N-dimethylaminomethyl which is located at the 3-position or 5-position, preferably 3-position of the benzothiophen-2-yl or benzofuran-2-yl ring. Even more preferably, $Ar^2$ is benzofuran-2-yl, 3-N,N-dimethylaminomethyl-benzofuran-2-yl, or 3-phenoxymethylbenzofuran-2-yl.

(vi) Within the groups (A)-(C), another more preferred group of compounds is that wherein $Ar^1$ is phenylene in which the hydroxamate and the X group are para to each other and $Ar^2$ is indol-2-yl, benzofuran-2-yl or benzothiophen-2-yl and is substituted with phenyloxyalkyl, substituted heteroaryloxyalkyl, substituted heterocycloalkyloxyalkyl, or haloalkoxyalkyl which are located at the 3-position of the benzothiophen-2-yl and benzofuran-2-yl rings. Even more preferably, $Ar^2$ is 3-(2,2,2-trifluoroethyloxymethyl)benzofuran-2-yl.

(vii) Within the groups (A)-(C), another more preferred group of compounds is that wherein $Ar^1$ is heteroarylene and $Ar^2$ is aryl. Preferably $Ar^1$ is five membered heteroarylene ring containing one, two, or three heteroatoms independently selected from N, O or S, more preferably $Ar^1$ is isoxazolyl where the hydroxamate and the X groups are located at the 5- and 3-position of the isoxazolyl ring, the oxygen atom in the ring being position 1 and $Ar^2$ is aryl. Preferably $Ar^2$ is phenyl that is optionally substituted with one or two substituents independently selected from methoxy, ethoxy, phenyl optionally substituted with ethoxy or methyl, tert-butyl, pyrrol-1-yl, cyclohexene-3-oxy, pyridin-3-yl, pyridin-2-yl, benzoylamino, fluoro, chloro, or thiophen-2-ylmethoxy.

More preferably, $Ar^2$ is phenyl, 4-biphenyl, 3-biphenyl, 2-(2-ethoxyphenyl)phenyl, 3-methylbiphen-4-yl, 4-tert-butylphenyl, 4-pyrrol-1-ylphenyl, 4-(cyclohexene-3-oxy)phenyl, 4-(pyridin-2-yl)phenyl, 4-(pyridin-3-yl)phenyl, 2,4-difluorophenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro-4-methoxyphenyl, 2-thiophen-2-ylmethoxyphenyl, 3-thiophen-2-ylmethoxyphenyl, 2-biphenyl, or 2-pyrrol-1-ylphenyl.

(viii) Within the groups (A)-(C), another more preferred group of compounds is that wherein $Ar^1$ is heteroarylene and $Ar^2$ is aryl-CH=CH—. Preferably $Ar^1$ is five membered heteroarylene ring containing one, two, or three heteroatoms independently selected from N, O or S, more preferably $Ar^1$ is isoxazolyl where the hydroxamate and the X groups are located at the 5- and 3-position of the isoxazolyl ring, the oxygen atom in the ring being position 1 and $Ar^2$ is phenyl-CH=CH— and is optionally substituted with alkoxy.

(ix) Within the groups (A)-(C), another more preferred group of compounds is that wherein $Ar^1$ is heteroarylene and $Ar^2$ is heteroaryl-CH=CH—. Preferably $Ar^1$ is five membered heteroarylene ring containing one, two, or three heteroatoms independently selected from N, O or S, more preferably $Ar^1$ is isoxazolyl where the hydroxamate and the X groups are located at the 5- and 3-position of the isoxazolyl ring, the oxygen atom in the ring being position 1 and $Ar^2$ is pyridinylCH=CH—.

(x) Within the groups (A)-(C), another more preferred group of compounds is that wherein $Ar^1$ is heteroarylene and $Ar^2$ is heteroaryl. Preferably $Ar^1$ is five membered heteroarylene ring containing one, two, or three heteroatoms independently selected from N, O or S, more preferably $Ar^1$ is isoxazolyl where the hydroxamate and the X groups are located at the 5- and 3-position of the isoxazolyl ring, the oxygen atom in the ring being position 1 and $Ar^2$ is pyridin-3-yl, thiophen-2-yl, quinolin-6-yl, thiazol-2-yl, benzthiazol-2-yl, benzoxazol-2-yl, furanyl, pyrrol-2-yl, indol-5-yl, indol-3-yl, indazol-3-yl, quinolin-3-yl, quinolin-8-yl, benzotriazol-4-yl, isoquinolin-1-yl, isoquinolin-3-yl, quinoxalin-2-yl, quinolin-2-yl, or benzimidazol-5-yl wherein said rings are optionally substituted with phenyl, pyridin-4-yl, methyl, methoxy, or dimethylaminomethyl.

(xi) Within the groups (A)-(C), another more preferred group of compounds is that wherein $Ar^1$ is heteroarylene and $Ar^2$ is indol-2-yl, benzofuran-2-yl or benzothiophen-2-yl which are optionally substituted with alkyl, alkoxy, halo, haloalkyl, alkoxyalkyloxy, optionally substituted heterocycloalkylalkyloxy, optionally substituted heteroaralkyloxy, hydroxyalkoxy, aminoalkyloxy, alkoxyalkyloxy, alkoxyalkyl, optionally substituted phenyloxyalkyl, or optionally substituted heterocycloalkylalkyl. Preferably $Ar^1$ is a five membered heteroarylene ring containing one, two, or three heteroatoms independently selected from N, O or S, more preferably $Ar^1$ is isoxazolyl where the hydroxamate and the X groups are located at the 5- and 3-position of the isoxazolyl ring, the oxygen atom in the ring being position 1 and $Ar^2$ is benzofuran-2-yl and benzothiophen-2-yl which are optionally substituted with methoxy, methyl, chloro, trifluoromethyl, fluoro, 2-methoxyethoxy, 2-morpholin-4-ylethoxy, pyridin-3-ylmethoxy, 2-hydroxyethoxy, 2-N,N-dimethylaminoethoxy, ethyl, methoxymethyl, phenoxymethyl, morpholin-4-ylmethyl, or dimethylaminomethyl and are located at the 3-position of the benzothiophen-2-yl and benzofuran-2-yl rings. Even more preferably, $Ar^2$ is benzofuran-2-yl or 3-phenoxymethylbenzofuran-2-yl.

(xii) Within the groups (A) and (B), another more preferred group of compounds is that wherein Ar² is substituted with alkoxyalkyloxy, optionally substituted heterocycloalkylalkyloxy, hydroxyalkoxy, aminoalkyloxy, alkoxyalkyloxy, alkoxyalkyl, optionally substituted phenyloxyalkyl, optionally substituted heteroaryloxyalkyl, or optionally substituted heterocycloalkylalkyl. Within this group, a more preferred group of compounds is that wherein Ar¹ and Ar² are as described in preferred embodiments above.

II. Another preferred group of compounds of Formula (I) is that wherein X is —O—, R¹ is hydrogen, Ar¹ is phenylene and Ar² is heteroaryl; where the scope of the terms contained within preferred Group II are as defined in the definition section of the Application.

Preferably, the compound is represented by Formula (Ia):

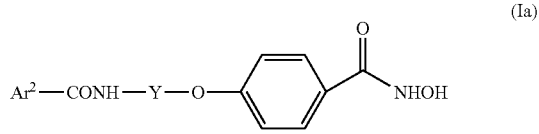

(Ia)

wherein:

Y is alkylene optionally substituted with cycloalkyl, optionally substituted phenyl, alkylthio, alkysulfonyl, optionally substituted phenylalkylthio, optionally substituted phenylalkylsulfonyl, hydroxy, or optionally substituted phenoxy; and Ar² is heteroaryl.

Preferably, Ar² is heteroaryl optionally substituted with one or two substituent(s) independently selected from alkyl, halo, haloalkyl, alkoxy, alkoxyalkyl, hydroxyalkoxy, hydroxyalkoxyalkyl, alkoxyalkyloxy, alkoxyalkyloxyalkyl, aminoalkyl, aminoalkoxy, haloalkoxy, haloalkoxyalkyl, optionally substituted phenyl, optionally substituted phenoxy, optionally substituted phenylalkyloxy, optionally substituted phenylalkyl, optionally substituted phenyloxyalkyl, optionally substituted heteroaryl, optionally substituted heteroaralkyloxy, optionally substituted heteroaryloxyalkyl, optionally substituted heterocycloalkylalkyl, optionally substituted heterocycloalkyloxy, optionally substituted heterocycloalkylalkyloxy, -alkylene-S(O)ₙRᵃ (where n is 0 to 2 and Rᵃ is hydroxyalkyl or optionally substituted phenyl), -alkylene-NRᵉ-alkyleneCONRᶜRᵈ (where Rᶜ is hydroxyl and Rᵈ and Rᵉ are independently hydrogen or alkyl), or carboxyalkylaminoalkyl.

Preferably, Ar² is thiophen-2-yl, pyridin-3-yl, quinolin-6-yl, benzothiazol-2-yl, benzoxazol-2-yl, benzofuran-2-yl, benzofuran-5-yl, benzothien-2-yl, furan-2-yl, 1H-benzimidazol-2-yl, 1H-pyrrol-2-yl, thiazol-2-yl, 1H-indol-2-yl, 1H-indol-5-yl, 1H-indol-3-yl, quinolin-3-yl, quinolin-8-yl, 1H-indazol-3-yl, 1H-benzotriazol-5-yl, isoquinolin-1-yl, isoquinolin-3-yl, quinoxalin-2-yl, quinolin-2-yl, 1H-benzimidazol-5-yl, quinolin-1-yl, pyridin-2-yl, pyridine-2-yl, quinolin-2-yl, furan-3-yl, thiophen-2-yl, or thiophen-3-yl, more preferably benzofuran-2-yl, or benzothien-2-yl that is optionally substituted with one or two substituents described in the paragraph immediately above.

Even more preferably Ar² is benzofuran-2-yl and is monosubstituted at the 3-, 4- or 5-position or disubstituted at the 4 and 7 positions, preferably the benzofuran-2-Y1 is monosubstituted at the 3 or 5 position with a substituent described in the paragraph immediately above. More preferably, the substituents are independently selected from chloro, fluoro, trifluoromethyl, methyl, ethyl, methoxy, 1-cyclopropylpiperidin-4-yloxy, 1-(2,2,2-trifluoroethyl)piperidin-4-yloxy, N,N-dimethylaminomethyl, N,N-diethylaminomethyl, 2-methoxyethoxymethyl, phenoxymethyl, 2-methoxyethoxy, 2-morpholin-4-ylethoxy, pyridin-3-yl-methoxy, 2-hydroxyethoxy, 2-N,N-dimethylaminoethoxy, methoxymethyl, 3-i-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1.2.4-triazin-1-yl-phenoxymethyl, 2-phenylethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-N-2-phenylethylaminomethyl, 3-hydroxypropylthiomethyl, 3-hydroxypropylsulfinylmethyl, 3-hydroxypropylsulfonyl-methyl, N-methyl-N-2-indol-3-ylethylaminomethyl, 2-(4-trifluoromethylphenyl)ethyl, 2-(3-trifluoromethoxyphenyl)ethyl, N-hydroxyaminocarbonyl-methylaminomethyl, or 3-(2-carboxyethylaminomethyl.

Even more preferably, Ar² is benzofuran-2-yl that is substituted at the 3-position with N,N-dimethylaminomethyl, N,N-diethylaminomethyl, 2-fluorophenoxymethyl, 3-fluorophenoxymethyl, 4-fluorophenoxymethyl, pyridin-4-yloxymethyl, 2,4,6-trifluorophenoxymethyl, 2-oxopyridin-1-ylmethyl, 2,2,2-trifluoroethoxy-methyl, 4-imidazol-1-ylphenoxymethyl, 4-[1.2.4]-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenylethyl)-, N-methyl-N-benzylaminomethyl, N-methyl-N-2-phenylethylaminomethyl, 3-hydroxypropylthiomethyl, 3-hydroxypropylsulfinyl-methyl, 3-hydroxypropylsulfonylmethyl, N-methyl-N-2-indol-3-ylethylaminomethyl, 2-(4-trifluoromethylphenyl)ethyl, N-hydroxyaminocarbonyl-methylaminomethyl, or 2-carboxyethylamino-methyl.

Even more preferably, Ar² is benzofuran-2-yl that is substituted at the 5-position with 1-cyclopropylpiperidin-4-yloxy, piperidin-4-yloxy, tetrahydropyran-4-yloxy, 2,2,2-trifluoroethoxy, 2-pyrrolidin-1-ylethyloxy, or 1-(2,2,2-trifluoroethyl)piperidin-4-yloxy.

Even more preferably, Ar² is 7-chloro-4-methylbenzofuran-2-yl, 4-methylbenzofuran-2-yl, 7-fluoro-4-methylbenzofuran-2-yl, or 7-fluoro-4-phenoxymethylbenzofuran-2-yl.

Even more preferably, Ar² is thiophen-2-yl, pyridin-3-yl, 5-phenylthiophen-2-yl, quinolin-6-yl, 4-phenylthiazol-2-yl, benzothiazol-2-yl, benzoxazol-2-yl, furan-2-yl, 1H-benzimidazol-2-yl, 1H-pyrrol-2-yl, 4-(pyridin-4-yl)-thiazol-2-yl, 1H-indol-5-yl, 1H-indol-3-yl, quinolin-3-yl, quinolin-8-yl, 1H-indazol-3-yl, 1H-benzotriazol-5-yl, isoquinolin-1-yl, isoquinolin-3-yl, quinoxalin-2-yl, quinolin-2-yl, 1H-benzimidazol-5-yl, 1-methyl-indol-3-yl, 4-MeO-quinolin-2-yl, quinolin-4-yl, 4-hydroxyquinolin-2-yl, pyridin-2-yl, 3-hydroxypyridin-2-yl, 6-hydroxypyridin-2-yl, 6-(4-nitrophenoxy)pyridin-2-yl, 4-(2-methoxyethoxy)quinolin-2-yl, 4-(2-dimethylaminoethoxy)quinolin-2-yl, 6-bromopyridin-2-yl, 5-bromopyridin-3-yl, 4-methoxyquinolin-2-yl, 5-phenylpyridin-3-yl, 6-benzyloxypyridin-2-yl, 6-(2-methylpropyloxy)pyridin-2-yl, 6-(2-phenylethyloxy)pyridin-2-yl, 4-(3,3,3-trifluoropropyloxy)quinolin-2-yl, 5-thiophen-3-ylpyridin-3-yl, 6-(4-acetylaminophenoxy)-pyridin-2-yl, 6-(4-aminophenoxy)pyridin-2-yl, or 5-(4-dimethylaminophenyl)pyridin-3-yl.

Within the preferred and more preferred embodiments in group (II):

(D) A more preferred group of compounds is that wherein Y is straight alkylene, preferably ethylene or n-propylene, preferably ethylene.

(E) Another more preferred group of compounds is that wherein Y is branched alkylene, preferably —CH($C_2H_5$)$CH_2$—, —CH(i-$C_3H_7$)$CH_2$—, or —CH($CH_3$)$CH_2$— and the stereochemistry at the chiral carbon is (S). More preferably, Y is —CH($C_2H_5$)$CH_2$—.

(F) Yet another more preferred group of compounds is that wherein Y is —$CH_2$CH($CH_3$)— and the stereochemistry at the chiral carbon is (R).

(G) Yet another more preferred group of compounds is that wherein Y is —CH(CHR')$CH_2$— where R' is alkylthio, alkylsulfonyl, optionally substituted phenylalkylthio, optionally substituted phenylalkylsulfonyl, hydroxy, or optionally substituted phenoxy.

III. Another preferred group of compounds of Formula (I) is that wherein X is —O—, $R^1$ is hydrogen, $Ar^1$ is phenylene and $Ar^2$ is aralkenyl; where the scope of the terms contained within preferred Group III are as defined in the definition section of the Application.

Preferably, the compound is represented by Formula (Ib):

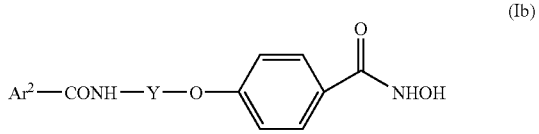

(Ib)

wherein:

Y is alkylene optionally substituted with cycloalkyl, optionally substituted phenyl, alkylthio, alkylsulfonyl, optionally substituted phenylalkylthio, optionally substituted phenylalkylsulfonyl, hydroxy, or optionally substituted phenoxy; and $Ar^2$ is aryl($C_{2-3}$)alkenyl.

Preferably $Ar^2$ represented by the formulae:

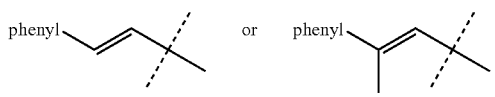

where phenyl is optionally substituted with one or two substituents independently selected from alkyl, alkoxy, methylenedioxy, dialkylamino, or hydroxy.

Preferably, $Ar^2$ is trans phenyl-CH═CH—, trans 4-MeO-phenyl-CH═CH—, trans 3,4-methylenedioxyphenylCH═CH—, trans 3-hydroxyphenyl-CH═CH—, trans 4-hydroxyphenyl-CH═CH—, trans 2-methoxyphenyl-CH═CH—, trans 3-methoxyphenyl-CH═CH—, trans 3-tolyl-CH═CH—, trans 4-tolyl-CH═CH—, trans 4-dimethylaminophenyl-CH═CH—, trans 2-tolyl-CH═CH—, or trans 2-hydroxyphenyl-CH═CH—.

Within this group of compounds, more preferred groups are where Y is as described in (II) D-G above.

IV. Another preferred group of compounds of Formula (I) is represented by Formula (Ic):

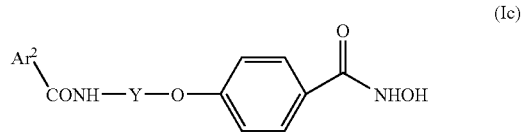

(Ic)

wherein:

Y is alkylene optionally substituted with cycloalkyl, optionally substituted phenyl, alkylthio, alkylsulfonyl, optionally substituted phenylalkylthio, optionally substituted phenylalkylsulfonyl, hydroxy, or optionally substituted phenoxy; and $Ar^2$ is heteroaryl($C_{2-3}$)alkenyl; where the scope of the terms contained within preferred Group IV are as defined in the definition section of the Application.

Preferably, $Ar^2$ is trans heteroaryl-CH═CH— or trans heteroaryl-C($CH_3$)═CH—, preferably heteroaryl ring is pyridinyl, benzofuranyl, thienyl (thiophene), furanyl, or indolyl optionally substituted with one or two substituents selected from hydroxyl, alkoxy, halo, or optionally substituted heterocycloalkoxy.

Preferably, $Ar^2$ is trans pyridin-3-yl-CH═CH—, trans 5-hydroxybenzofuran-2-yl —C($CH_3$)═CH—, trans 5-(1-cyclopropylpiperidin-4-yloxy)benzofuran-2-yl —C($CH_3$)═CH—, trans 5-methoxybenzofuran-2-yl —C($CH_3$)═CH—, trans benzofuran-2-yl-CH═CH—, trans 5-bromothiophen-2-yl-CH═CH—, trans furan-3-yl-CH═CH—, trans thiophen-3-yl-CH═CH—, trans thiophen-2-yl-CH═CH—, trans benzofuran-2-yl —C($CH_3$)═CH—, cis benzofuran-2-yl —C($CH_3$)═CH—, trans indol-3-yl CH═CH—, trans 7-methoxybenzofuran-2-yl —CH═CH—, trans 5-methoxybenzofuran-2-yl —C($CH_3$)═CH—, or trans furan-2-yl-CH═CH.

Within this group of compounds, more preferred groups are where Y is as described in (II) D-G above.

V. Another preferred group of compounds of Formula (I) is that wherein X is —O—, $R^1$ is hydrogen, $Ar^1$ is phenylene and $Ar^2$ is aryl; where the scope of the terms contained within preferred Group V are as defined in the definition section of the Application.

Preferably, the compound is represented by Formula (Id):

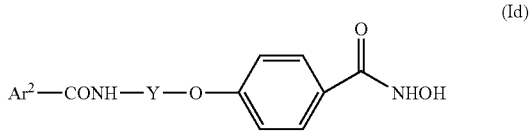

(Id)

wherein:

Y is alkylene optionally substituted with cycloalkyl, optionally substituted phenyl, alkylthio, alkylsulfonyl, optionally substituted phenylalkylthio, optionally substituted phenylalkylsulfonyl, hydroxy, or optionally substituted phenoxy; and $Ar^2$ is aryl.

Preferably, the substituents on the aryl ring are independently selected from optionally substituted phenyl, alkyl, alkoxy, halo, optionally substituted heteroaryl, optionally substituted cycloalkenyloxy, optionally substituted heteroaralkyloxy, optionally substituted heterocycloalkyl, optionally substituted phenylcarbonylamino, or methylenedioxy. More preferably, Ar² is phenyl, 4-biphenyl, 3-biphenyl, 4-tert-butylphenyl, 4-pyrrol-1-ylphenyl, 4-(pyridin-3-yl)phenyl, 4-(pyridin-2-yl)phenyl, 4-benzoylamino)phenyl, 2,4-difluorophenyl, 3,4-methylenedioxyphenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro-4-methoxyphenyl, 2-(thiophen-2-ylmethoxy)phenyl, 3-(thiophen-2-ylmethoxy)-phenyl, 2-biphenyl, naphth-1-yl, 2-pyrrol-1-ylphenyl, 4-fluoronaphth-1-yl, 3-MeO-naphth-2-yl, 2-MeO-naphth-1-yl, naphth-2-yl, 4-(2-pyridin-4-ylthiazol-5-yl)phenyl, 4-[2-(4-methylpiperazin-1-yl)thiazol-5-yl]-phenyl, 4-(2-pyridin-4-ylaminothiazol-5-yl)phenyl, 4-(4-methylpiperazin-1-yl)phenyl, 4-(4-hydroxypiperidin-1-yl)phenyl, 4-(4-morpholin-4-ylmethylthiazol-2-yl)phenyl, 4-[2-(4-methylpiperazin-1-ylmethyl)thiazol-5-yl]phenyl, 1-methoxynaphth-2-yl, 3'-(2-hydroxyethyl)biphen-4-yl, 3'-(2-hydroxyethyl)biphen-3-yl, 2'-(2-hydroxyethyl)biphen-4-yl, 2'-(2-hydroxyethyl)biphen-3-yl or 4-[4-(2-morpholin-4-ylethyl)thiazol-2-yl]phenyl.

Within this group of compounds, more preferred groups are where Y is as described in (II) D-G above.

Reference to the preferred embodiments set forth above is meant to include all combinations of particular and preferred groups unless stated otherwise.

General Synthesis

Compounds of this invention can be made by the methods depicted in the reaction scheme shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 140 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where X is —O— or —S(O)$_n$— where n is 0 to 2 and other groups are as described in the Summary of the Invention can be prepared by the procedure illustrated and described in Scheme A below.

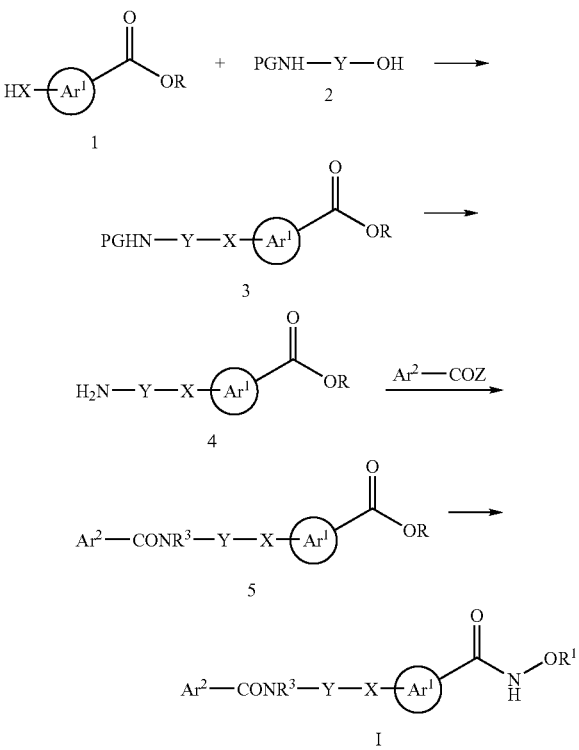

Reaction of a compound of formula I where R is alkyl, X is —O— or —S— and Ar¹ is as defined in the Summary of the Invention with an aminoalcohol of formula 2 where PG is a suitable amino protecting group provides a compound of formula 3. The reaction is carried out in the presence of triphenylphosphine and diisopropyl azodicarboxylate in a suitable organic solvent such as tetrahydrofuran, and the like.

Compounds of formula I such as methyl 4-hydroxybenzoate, methyl 4-mercaptobenzoate, and methyl 3-hydroxyisoxazole-5-carboxylate are commercially available. Compounds of formula 2 can be prepared from commercially available aminoalcohols by reacting the amine with a suitable amino protecting group such as benzyloxycarbonyl, tert-butoxycarbonyl and the like under reaction conditions well known in the art. A detailed description of suitable amino protecting groups and reaction conditions for their preparation can be found in T. W. Greene, *Protecting Groups in Organic Synthesis*, John Wiley & Sons, Inc. 1981 the teaching of which is incorporated herein by reference in its entirety. Aminoalcohols such as 2-ethanolamine, 2-amino-1-propanol, 2-methylaminoethanol, 2-amino-2-methyl-1-propanol, 2-amino-1-propanol, 4-amino-2-butanol, and 1-amino-2-butanol are commercially available. Alternatively, compounds of formula 2 can be prepared from commercially available aminoacids by protecting the amino group with a suitable protecting group followed by reduction of the acid group to the hydroxy group with a suitable reducing agent under conditions well known in the art. If compounds of Formula (I) where X is —SO₂— are desired, the corresponding compound of formula 3 where X is —S— can be treated with an oxidizing agent such as OXONE®, m-chloroperbenzoic acid, and the like.

Removal of the amino protecting group in 3 provides a compound of formula 4. The reaction conditions employed for removal of the amino protecting group depend on the nature of the protecting group. For example, if the protecting group is tert-butoxycarbonyl, it is removed under acid reaction conditions. Suitable acids are trifluoroacetic acid, hydrochloric acid, and the like in a suitable organic solvent such as methanol, dioxane, tetrahydrofuran, and the like. If the protecting group is benzyl or benzyloxycarbonyl, it is removed under catalytic hydrogenation reaction conditions. Suitable catalyst are palladium based catalysts and others known in the art. Other suitable reaction conditions for their removal can be found in T. W. Greene, *Protecting Groups in Organic Synthesis*, John Wiley & Sons, Inc. 1981. The reaction is carried out in an inert organic solvent methylene chloride, tetrahydrofuran, dioxane, and the like.

Reaction of 4 with an acid or acid derivative (e.g., acid halide) of formula $Ar^2$—COZ where Z is hydroxy or halo provides a compound of formula 5. Again, the reaction conditions employed depend on the nature of the Z group. If Z is hydroxy, the reaction is typically carried out in the presence of a suitable coupling agent e.g., benzotriazole-1-yloxy-trispyrrolidino-phosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC. HCl), or 1,3-dicyclohexylcarbodiimide (DCC), optionally in the presence of 1-hydroxybenzotriazole hydrate (HOBT. $H_2O$), and a base such as N,N-diisopropylethylamine, triethylamine, N-methylmorpholine, and the like. The reaction is typically carried out at 20 to 30° C., preferably at about 25° C., and requires 2 to 24 hours to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. Preferably, the reaction is carried out with HOBt. $H_2O$, EDC.HCl in dichloromethane or N,N-dimethylformamide.

When $Ar^2COZ$ is an acid halide, the reaction is carried out in the presence of a suitable base (e.g. triethylamine, diisopropylethylamine, pyridine, and the like). Suitable reaction solvents are polar organic solvents such as tetrahydrofuran, acetonitrile, N,N-dimethylformamide (DMF), dichloromethane, or any suitable mixtures thereof. The acid halide such as acid chloride can be prepared by reacting the corresponding acids with a halogenating agent such as oxalyl chloride, thionyl chloride, phosphorus oxychloride, and the like. Acids of formula $Ar^2COZ$ are either commercially available or they can be prepared from commercially available starting materials by methods known in the art. For example, benzoic acid, cinnamic acid, phenylacetic acid, nicotinic acid, isonicotinic acid, 3-methylbenzofuran-2-carboxylic acid, and benzofuran-2-carboxylic acid are commercially available. Others such as 3-phenoxymethylbenzofuran-2-carboxylic acid can be readily prepared from commercially available 3-methylbenzofuran-2-carboxylic acid by first converting it to 2-bromomethylbenzofuran-2-carboxylic acid (brominating it with N-bromosuccinimide under conditions well known in the art) followed by reacting with phenol. Compound 5 where $R^3$ is hydrogen can optionally be converted to a corresponding compound of formula 5 where $R^3$ is other than hydrogen by reacting it with an alkylating agent under conditions well known in the art.

Compound 5 is then converted to a compound of Formula (I) by reacting it with aqueous hydroxylamine in the presence of a base such as sodium hydroxide and a mixture of organic solvents such as tetrahydrofuran and methanol. Alternatively, the acid group in 5 is first activated with a suitable coupling agent such as 1-(3-dimethylaminopropyl)-3-ethylcarbodiimide hydrochloride (EDC. HCl), or 1,3-dicyclohexylcarbodiimide (DCC), optionally in the presence of 1-hydroxybenzotriazole hydrate (HOBT. $H_2O$) in a suitable organic solvent such as dimethylformamide, and the like, and then reacted with hydroxylamine hydrochloride in the presence of a base such as N,N-diisopropylethylamine, triethylamine, N-methylmorpholine, and the like. Compounds of Formula (I) can also be prepared from compound 5 by the methods disclosed in U.S. Pat. No. 5,998,412, the disclosure of which is incorporated herein by reference in its entirety.

A compound of Formula (I) can be converted to other compounds of Formula (I). For example, a compound of Formula (I) where $Ar^1$ is phenylene, X is —O—, Y is ethylene, $Ar^2$ is 3-dimethylaminomethylbenzofuran-2-yl, $R^1$ and $R^3$ are hydrogen can be prepared by reacting a compound of formula 4 where $Ar^1$ is phenylene, X is —O—, Y is ethylene, and R is alkyl with 3-methylbenzofuran-2-carboxylic acid as described above to give a compound of formula 5 where $Ar^2$ is 3-methylbenzofuran-2-yl. Bromination of the methyl group with a suitable brominating agent such as N-bromosuccinimide, followed by reaction with dimethylamine provides the corresponding 3-dimethylaminobenzofuran-2-yl compound which is then converted to the desired compound under the reaction conditions described above.

Utility

The compounds of this invention are inhibitors of histone deacetylase enzymes and are therefore useful in the treatment of proliferative diseases such as cancer such as lung, colon, AML, MML, skin, breast, ovarian, prostate, liver, brain and skin, psoriasis, fibroproliferative disorder such as liver fibrosis, smooth muscle proliferative disorder such as atherosclerosis and restenosis, inflammatory diseases such as arthritis, diseases involving angiogenesis such as cancer, diabetic retinopathy, haematopoietic disorder such as anaemia, fungal, parasitic and bacterial infections, viral infection, autoimmune diseases such as arthritis, multiple sclerosis, lupus, allergies, asthma, allergic rhinitis, and organ transplant, and bipolar disorders. Additionally, the compounds of the present invention are useful in the treatment of hepatitis C infection.

Testing

The ability of the compounds of this invention to inhibit histone deacetylase enzymes can be tested in vitro and in vivo assays described in biological assays Example 1 and 2 below. The hcv activity of the compounds of this invention was tested in a hcv replicon assay at Georgetown University. The compounds can also be tested for hcv activity utilizing the replicon assay described in Korner, V. L. et al., *Science* 1999 Jul. 2:285 (5424):110-3.

Administration and Pharmaceutical Compositions

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.1-50 mg per kilogram body weight of the recipient per day; preferably about 0.5-20 mg/kg/day. Thus, for administration to a 70 kg person, the dosage range would most preferably be about 35 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral or parenteral using a convenient daily dosage regimen, which can be adjusted according to the degree of affliction. Oral compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18$^{th}$ ed., 1990).

The amount of the compound in a formulation can vary within the full range employed by those skilled in the art. Typically, the formulation will contain, on a weight percent (wt %) basis, from about 0.01-99.99 wt % of a compound of Formula (I) based on the total formulation, with the balance being one or more suitable pharmaceutical excipients. Preferably, the compound is present at a level of about 1-80 wt %.

Representative pharmaceutical formulations containing a compound of Formula (I) are described below.

As stated previously, the compounds of this invention can be administered in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, DNA methyl tranferase inhibitors, and other angiogenesis inhibitors. The compound of the present invention compounds are particularly useful when administered in combination with radiation therapy. Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF.

Preferred estrogen receptor modulators are tamoxifen and raloxifene.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro)platinum(II)]-tetrachloride, diarizidinyispermine, arsenic trioxide, 1-(11-odecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxy-caminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)colchic(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)-amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine oefosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]-adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetra cyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein. It has been reported that (Int. J. Cancer, 20; 97(6):746-50, 2002) combination therapy with lovastatin, a HMG-CoA reductase inhibitor, and butyrate, an inducer of apoptosis in the Lewis lung carcinoma model in mice showed potentiating antitumor effects Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911, 165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and □olchicin the use of such salts, esters, open-acid and lactone forms is included within the scope of this invention.

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin.

Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium hydroxyl, camsylate, carbonate, chloride, clavulanate, citrate, dihydrochloride, hydroxyl, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)quinolinone, (−)-6-[amino(4-chlorophenyl)(1-methyl-1H-imidazol-5-yl) methyl]-4-(3-chloro phenyl)-1-methyl-2(1H)-quinolinone, (+)-6-[amino(4-chlorophenyl)(1-methyl-1H-imidazol-5-yl) methyl]-4-(3-chloro phenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)-methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-{3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4] dioxa-azacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]-oxatriazacyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacyclo-eicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9, 12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see J. Of Cancer, Vol. 35, No. 9, pp. 1394-1401 (1999).

Examples of HIV protease inhibitors include amprenavir, abacavir, CGP-73547, CGP-61755, DMP450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HB Y097, lamivudine, nevirapine, AZT, 3TC, ddC, and ddI. It has been reported (Nat. Med.; 8(3):225-32, 2002) that HIV protease inhibitors, such as indinavir or saquinavir, have potent anti-angiogenic activities and promote regression of Kaposi sarcoma "Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-$\alpha$, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin., Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 µM or less as measured by the cell or microsomal assay known in the art.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or microsomal assay disclosed hereinunder. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference. Other examples of specific inhibitors of COX-2 include those disclosed in U.S. Pat. No. 6,313,138 the disclosure of which is incorporated herein by reference in its entirety.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

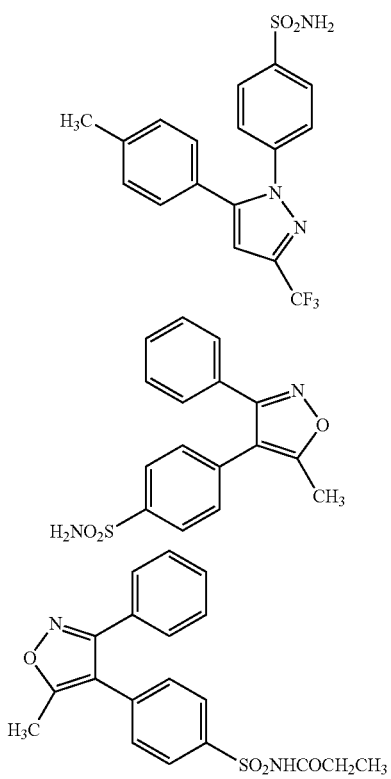

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RP14610, NX31838, sulfated mannopentose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$; $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, SU11248, STI571A, N-4-chlorophenyl-4-(4-pyridylmethyl)-1-phthalazinamine, and EMD121974.

The instant compounds are also useful, alone or in combination with platelet fibrinogen receptor (GP Iib/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, Platelets 10, 285-292, 1999). Therefore, the present compounds can serve to inhibit metastasis, alone or in combination with GP lib/IIIa) antagonists. Examples of other fibrinogen receptor antagonists include abciximab, eptifibatide, sibrafiban, lamifiban, lotrafiban, cromofiban, and CT50352.

"DNA methyltransferase inhibitor" refers to compounds which inhibit the methylation of the DNA base cytosine at the C-5 position of that base by the DNA methyltransferase enzyme. Examples of such DNA methyltransferase inhibitor include compounds disclosed in U.S. Pat. Nos. 6,329,412 and 6,268,137. Specific DNA methyltransferase inhibitors include 5-azacytosine and Zebularine®.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

The term administration and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the farnesyl-protein transferase inhibitors disclosed in U.S. Pat. No. 6,313,138 and an antineoplastic agent. It is also understood that such a combination of antineoplastic agent and inhibitor of farnesyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®, epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, caminomycin, daunorubicin, aminopterin, methotrexate, methopterin, dichloromethotrexate, mitomycin C, porfiromycin, Herceptin®, Rituxan®, 5-fluorouracil, 6-mercaptopurine, gemcitabine, cytosine arabinoside, podophyllotoxin or podo-phyllotoxin derivatives such as colchicines, etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. The preferred class of antineoplastic agents is the taxanes and the preferred antineoplastic agent is paclitaxel.

Radiation therapy, including x-rays or gamma rays that are delivered from either an externally applied beam or by implantation of tiny radioactive sources, may also be used in combination with the compounds of this invention alone to treat cancer.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of N-hydroxy-4-(2-benzenecarbonylamino-ethoxy)benzamide

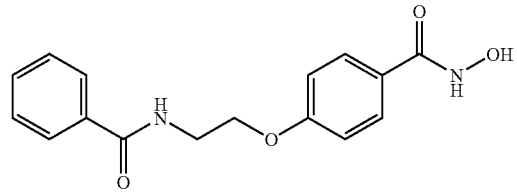

Step 1

To a solution of 2-aminoethanol (3.1 g, 50 mmol) in THF (10 ml) was added tert-butyloxycarbonyl anhydride (10.9 g, 50 mmol) in THF (150 ml). The reaction mixture was stirred for 3 h, then diluted with ethyl acetate, washed with 0.5 M aqueous HCl, and brine. The organic layer was dried ($MgSO_4$), filtered and concentrated in vacuo to give 2-N-Boc-aminoethanol which was directly used in the next step.

Step 2

To a solution of triphenylphosphine (17.7 g, 67.5 mmol) in anhydrous THF (135 ml) was added DIAD (13.6 g, 67.5 mmol). The solution was stirred until a white precipitate was formed (2 to 10 min). After additional 60 min., a solution of 2-N-Boc aminoethanol (7.2 g, 45 mmol) and methyl 4-hydroxybenzoate (6.8 g, 45 mmol) in THF (25 ml) was added and stirring was continued for 5 h. The reaction mixture was concentrated in vacuo and purified by flash chromatography to give methyl 4-(2-N-Boc aminoethoxy)benzoate. Alternatively, the crude material can directly be used in the next step.

Step 3

To a solution of crude methyl 4-(2-N-Boc aminoethoxy) benzoate in methanol (20 ml) was added 4M HCl/dioxane (180 ml). After stirring for 3 h, diethyl ether (300 ml) was added providing a white precipitate. The solid was collected, suspended in ethyl acetate and stirred for 15-20 min. The solid was collected again and dried under high vacuo providing methyl 4-(2-aminoethoxy)benzoate hydrochloride 6.3 g (60% over 2 steps).

Step 4

To a suspension of methyl 4-(2-amino-ethoxy)benzoate hydrochloride (0.232 g, 1 mmol) in THF (6 ml) was added benzoyl chloride (0.140 g, 1 mmol) followed by triethylamine (0.121 g, 1.2 mmol). The reaction mixture was stirred for 1 h and then diluted with ethyl acetate. The organic layer was washed with 0.5 M aqueous HCl, saturated sodium bicarbonate solution, and brine. The organic layer was concentrated in vacuo to give methyl 4-(2-benzenecarbonylamino-ethoxy)benzoate which was directly used in the next step.

Step 5

To a solution of crude methyl 4-(2-benzenecarbonylamino-ethoxy)benzoate (0.5 mmol) in a 1:1 mixture of THF/methanol (20 ml) was added 50 wt. % aqueous hydroxylamine (3 ml) followed by 1M aqueous NaOH (1 ml) adjusting the pH between 10-11. The reaction mixture was stirred for 14 h, neutralized to pH=7-8 with 6 M aqueous HCl and concentrated in vacuo. The precipitate was collected and purified by HPLC providing the title compound as a white solid. $^1$H NMR (DMSO-$d_6$): δ 8.69 (t, J=5.8 Hz, 1H), 7.83 (d, J=7.5 Hz, 2H), 7.69 (d, J=9.1 Hz, 2H), 7.46 (m, 3H), 6.99 (d, J=9.1 Hz, 2H), 4.16 (t, J=5.8 Hz, 2H), 3.63 (q, J=5.8 Hz, 2H). EM (calc.): 300.1; MS (ESI) m/e: 301.1 (M−1)$^+$, 299.0 (M+1)$^-$.

Proceeding as described in Example 1, Steps 1-4 above, but substituting 2-aminoethanol with (S)-(+)-2-amino-1-butanol provided methyl 4-(2S-aminobutoxy)benzoate hydrochloride.

Example 2

Synthesis of N-hydroxy-4-[2-(benzofuran-2-yl-carbonylamino)-ethoxy]-benzamide

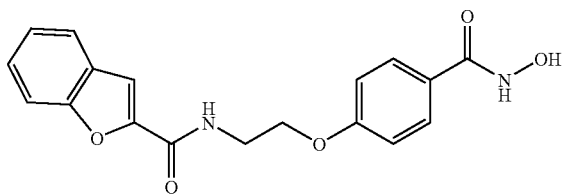

Step 1

A mixture of benzofuran-2-carboxylic acid (0.162 g, 1 mmol), EDC-HCl (0.268 g, 1.4 mmol) and HOBT.H$_2$O (0.203 g, 1.5 mmol) in DMF (6 ml) was stirred for 2 h. Methyl 4-(2-aminoethoxy)benzoate hydrochloride (0.232 g, 1 mmol) was added followed by triethylamine (0.121 g, 1.2 mmol). The reaction mixture was stirred for 2 h and then diluted with ethyl acetate, washed with saturated sodium bicarbonate solution, and brine. The organic layer was concentrated in vacuo and the crude 4-[2-(benzofuran-2-ylcarbonylamino)ethoxy]-benzoate was converted to the title compound as described in Example 1, Step 5 above. $^1$H NMR (DMSO-$d_6$) δ 11.05 (s, 1H), 8.92 (t, J=5.6 Hz, 1H), 8.88 (s, 1H), 7.76 (d, J=8.0 Hz, 1H), 7.70 (d, J=9.2 Hz, 2H), 7.64 (d, J=8.0 Hz, 1H), 7.55 (s, 1H), 7.46 (t, J=6.8 Hz, 1H), 7.32 (t, J=8.0 Hz, 1H), 7.01 (d, J=8.2 Hz, 2H), 4.18 (t, J=5.6 Hz, 2H), 3.67 (m, 2H). EM (calc.): 340.1; MS (ESI) m/e: (M+1H)$^+$: 341.0, (M−1H)$^-$: 339.1.

Example 3

Synthesis of N-hydroxy-4-[2-(benzothiophen-2-yl-carbonylamino)-ethoxy]-benzamide

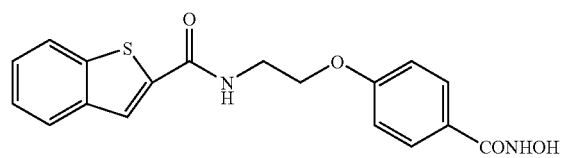

To a suspension of methyl 4-(2-aminoethoxy)benzoate hydrochloride (0.232 g, 1 mmol) in THF (6 ml) was added benzothiophene-2-carbonyl chloride (0.150 g, 1 mmol) followed by triethylamine (0.121 g, 1.2 mmol). The reaction mixture was stirred for 1 h and diluted with ethyl acetate (50 ml). The organic layer was washed with 0.5 M aqueous HCl, saturated sodium bicarbonate solution, and brine. The organic layer was concentrated in vacuo and the crude methyl 4-[2-(benzothiophen-2-yl-carbonylamino)ethoxy]benzoate was converted to the title compound as described in Example 1, Step 5 above.

Proceeding as described in Example 3 above, but substituting methyl 4-(2-aminoethoxy)benzoate hydrochloride with methyl 4-(2S-aminobutoxy)benzoate hydrochloride and benzothiophene-2-carbonyl chloride with cinnamoyl chloride provided N-hydroxy-4-[2S-(trans-cinnamoylamino)butoxy]benzamide.

Example 4

Synthesis of N-hydroxy-4-[2-(3-dimethylaminobenzofuran-2-ylcarbonylamino)ethoxy]-benzamide

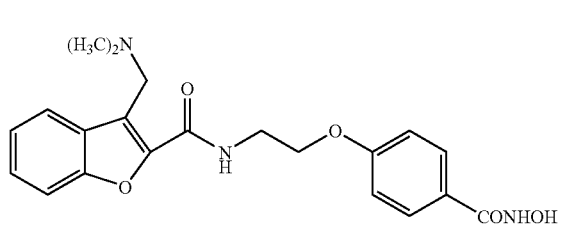

Step 1

To a solution of 3-methyl-benzofuran-2-carboxylic acid (0.98 g, 5.6 mmol) and 5 drops of DMF in THF (25 ml) was added oxalyl chloride (0.53 ml, 6.1 mmol). After stirring the solution for 1 h at room temperature, methanol (20 ml) and TEA (7 ml) were added. The slurry was stirred overnight at room temperature, then concentrated and dissolved in ethyl acetate (100 ml) and washed with mild NaHCO$_3$ (100 ml). The organic layer was dried (MgSO$_4$), filtered and concentrated to collect 3-methylbenzofuran-2-carboxylic acid methyl ester (1 g) as a tan solid. The crude methyl ester was used without further purification.

Step 2

A solution of 3-methylbenzofuran-2-carboxylic acid methyl ester (1.0 g, 5.3 mmol), NBS (0.95 g, 5.3 mmol) and AIBN (87 mg, 0.53 mmol) was heat to reflux in CCl$_4$ (40 ml) for 3 h, then cooled to room temperature and concentrated. The residue was dissolved in ethyl acetate (100 ml) and washed with water (100 ml). The organic layer was dried (MgSO$_4$), filtered and concentrated to collect 3-bromomethylbenzofuran-2-carboxylic acid methyl ester (1.55 g) of a tan/yellow solid which was used in the next step without further purification.

Step 3

3-Bromomethylbenzofuran-2-carboxylic acid methyl ester (269 mg, 1 mmol) was dissolved in anhydrous DMF and added 2M dimethylamine/THF solution (1.5 ml, 3 mmol). After 1-2 h, the reaction was diluted with EtOAc and washed twice with saturated NaHCO$_3$ (aq.) and brine. The organic extract over was dried over Na$_2$SO$_4$ and then concentrated in vacuo. The crude was purified on a silica gel column (5% MeOH in dichloromethane) to give 3-dimethylaminomethyl-benzofuran-2-carboxylic acid methyl ester (131 mg).

Step 4

To a solution of 3-dimethylaminomethylbenzofuran-2-carboxylic acid methyl ester (131 mg, 0.56 mmol) in MeOH was added 1N NaOH(aq.) till the pH of the solution was 13. The reaction mixture was stirred for 60-90 min. Upon completion, the reaction mixture was acidified to pH 3 with HCl (aq.) and concentrated to dryness to give 3-dimethylaminomethylbenzofuran-2-carboxylic acid as the HCl salt, which was used for next step without further purification.

Step 5

To 3-dimethylaminomethylbenzofuran-2-carboxylic acid (140 mg, 0.56 mmol) was added EDC.HCl (150 mg, 0.784 mmol) and HOBt.H$_2$O (114 mg, 0.84 mmol) in anhydrous DMF. The reaction mixture was stirred for 30-60 min., after which methyl-(4-(2-ethoxyamine))benzoate hydrochloric salt (130 mg, 0.56 mmol) and triethylamine (94 μL, 0.672 mmol) were added and the reaction was stirred overnight. The reaction mixture was diluted with EtOAc and washed twice with saturated NaHCO$_3$ (aq.) and brine. The organic extract was concentrated in vacuo to give methyl 4-[2-(3-dimethylaminobenzofuran-2-ylcarbonylamino)ethoxy]benzoate, which was then used without further purification.

Step 6

To a solution of crude methyl 4-[2-(3-dimethylaminobenzofuran-2-ylcarbonylamino)-ethoxy]-benzoate in MeOH and THF was added excess aqueous hydroxylamine solution and NaOH(aq.) to give pH 10-11. The reaction mixture was stirred overnight and then neutralized to pH 7-8 with aqueous hydrochloric acid and concentrated in vacuo. The residue was dissolved in acetonitrile and water and purified with prep HPLC to give the title compound (107 mg). $^1$H NMR (400 MHz, DMSO-d$_6$) δ 9.88 (m, 1H), 9.31 (t, J=6.0 Hz, 1H), 8.04 (d, J=7.6 Hz, 1H), 7.70 (m, 3H), 7.57 (t, J=7.6 Hz, 1H), 7.45 (t, J=7.6 Hz, 1H), 6.99 (d, J=9.2 Hz, 2H), 4.76 (d, J=4.8 Hz, 2H), 4.23 (t, J=6.0 Hz, 2H), 3.71 (m, 2H), 2.84 (s, 3H), 2.83 (s, 3H). EM (calc.): 397.2; MS (ESI) m/e (M+1H)$^+$: 398.1, (M−1H)$^-$: 396.2.

Example 5

Synthesis of N-hydroxy-4-{2-[3-(2,2,2-trifluoroethyloxymethyl)benzofuran-2-ylcarbonylamino]ethoxy}benzamide

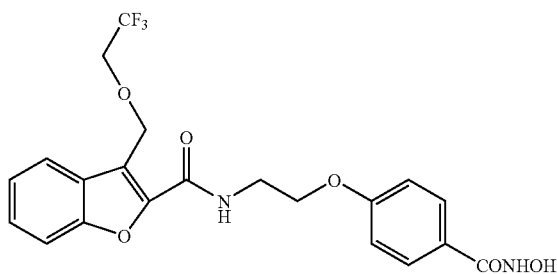

Step 1

Sodium hydride (15 mg, 0.56 mmol) was suspended in anhydrous DMF and stirred under N$_2$(g). 2,2,2-Trifluoroethanol (270 μL, 3.7 mmol) was added and after stirring the reaction mixture for 15-20 min., 3-bromomethylbenzofuran-2-carboxylic acid methyl ester was added. After 8 h, 1N NaOH (aq.) was added and the reaction mixture was stirred for 10-15 min. The reaction mixture was acidified reaction to pH 3 with aqueous hydrochloric acid and the product was extracted with EtOAc. The organic layer was dried organic over Na$_2$SO$_4$ and concentrated in vacuo to give 3-(2,2,2-trifluoroethoxymethyl)benzofuran-2-carboxylic acid (38 mg) which was then used without purification.

Step 2

To a solution of 3-(2,2,2-trifluoroethoxymethyl)benzofuran-2-carboxylic acid (38 mg, 0.139 mmol) in anhydrous DMF was added EDC.HCl (37 mg, 0.195 mmol) and HOBt.H$_2$O (26 mg, 0.195 mmol). After 60-90 min., methyl-(4-(2-ethoxyamine))benzoate hydrochloric salt (32 mg, 0.139 mmol) and triethylamine (23 μL, 0.167 mmol) were added and the reaction mixture was stirred for 1-2 h. The reaction mixture was diluted with EtOAc and washed twice with saturated NaHCO$_3$(aq.) and the organic extract was concentrated to give methyl 4-{2-[3-(2,2,2-trifluoroethoxymethyl)benzofuran-2-yl-carbonylamino]ethoxy}-benzoate, which was then used without further purification.

Step 3

4-{2-[3-(2,2,2-Trifluoroethoxymethyl)benzofuran-2-yl-carbonylamino]-ethoxy}-benzoate was dissolved in MeOH and excess aqueous hydroxylamine solution and NaOH(aq) were added to give pH 10-11. After stirring overnight, the reaction mixture was neutralized reaction to pH 7-8 with aqueous hydrochloric acid. The reaction mixture was concentrated in vacuo to give a solid which was collected and washed with water, then dissolved in acetonitrile and water and purified with prep HPLC to give the title compound (35 mg). $^1$H NMR (400 MHz, DMSO-d$_6$) δ 11.04 (s, 1H), 8.95 (t, J=5.6 Hz, 1H), 8.89 (s, 1H), 7.81 (d, J=7.6 Hz, 1H), 7.70 (d, J=8.8 Hz, 2H), 7.63 (d, J=8.8 Hz, 1H), 7.50 (t, J=8.8 Hz, 1H), 7.36 (t, J=8.0 Hz, 1H), 7.00 (d, J=9.2 Hz, 2H), 5.25 (s, 2H), 4.18 (m, 4H), 3.67 (m, 2H). EM (calc.): 452.1; MS (ESI) m/e (M+1H)$^+$: 453.0, (M−1H)$^-$: 451.0.

Example 6

Synthesis of N-hydroxy-4-{2-[5-(2-pyrrolidin-1-ylethyloxy)benzofuran-2-ylcarbonylamino]ethoxy}benzamide

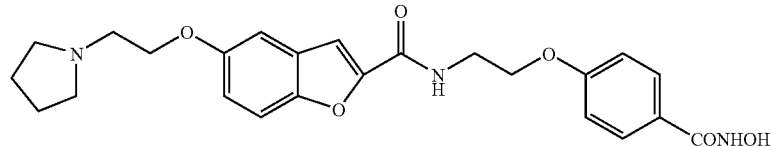

Step 1

5-Methoxybenzofuran-2-carboxylic acid (5.04 g, 26 mmol) was weighed into a 200 ml round bottom flask fitted with a stir bar, septum and nitrogen inlet. Anhydrous MeOH (50 ml) was added under nitrogen atmosphere. The solution was cooled in an ice bath and thionyl chloride (2.3 ml, 32 mmol) was added dropwise with vigorous stirring. After stirring for 72 h at room temperature, the reaction mixture was poured into water (150 ml) and the white solid was collected. The solid was dissolved in toluene (100 ml) and the solution was washed with 1M NaHCO$_3$ and brine and dried over MgSO$_4$. Removal of the organic layer provided 5-methoxybenzofuran-2-carboxylic acid methyl ester as a white solid (5.15 g).

Step 2

A solution of 5-methoxybenzofuran-2-carboxylic acid methyl ester (5.15 g, 25 mmol) in anhydrous methylene chloride (15 ml) was cooled to 40l under nitrogen atmosphere. Boron tribromide in CH$_2$Cl$_2$ (27 ml of 1.0 M) was added over 1 h using a syringe pump. The reaction mixture was allowed to warm to room temperature. After 16 h, the reaction mixture was cooled in an ice bath and quenched with MeOH (15 ml). The reaction mixture was poured into brine (100 ml) and extracted with EtOAc. The organic extracts were dried over anhydrous MgSO$_4$, and the solvent was removed on rotary evaporator. The residue was triturated with hexane and the yellow solid was filtered and dissolved in anhydrous MeOH (30 ml). The solution was cooled in an ice bath and thionyl chloride (1.9 ml, 26 mmol) was added dropwise. After 72 h, water (100 ml) was added and solid was collected. Purification of the crude product on a 300 cm$^3$ silica gel in a 5×15 cm plug using EtOAc provided 5-hydroxy-benzofuran-2-carboxylic acid methyl ester (4.53 g).

Step 3

Anhydrous tetrahydrofuran (15 ml) was added to a mixture of 5-hydroxybenzofuran-2-carboxylic acid methyl ester (1.10 g, 5.7 mmol), triphenylphosphine (1.50 g, 5.7 mmol), and 1-(2-hydroxyethyl)-pyrrolidine (0.66 g, 5.7 mmol) under a nitrogen atmosphere. Diisopropyl azodicarboxylate (1.15 ml, 5.8 mmol) was slowly added to the solution at room temperature. After 2 days, the solvent was removed and the residue was dissolved in a 2:1 mixture of Et$_2$O:EtOAc (150 ml). The solution was washed with 1.0M aqueous NaOH. The product was extracted into 1.0 M hydrochloric acid and the combined acid extracts were washed with Et$_2$O. The extracts were cooled and the pH of the extracts was adjusted to pH 12 with 50% aqueous NaOH. The basic solution was extracted with CH$_2$Cl$_2$ and the organic layer was dried over anhydrous MgSO$_4$, and concentrated to give 5-(2-pyrrolidin-1-yl-ethoxy)benzofuran-2-carboxylic acid methyl ester (0.96 g) as an amber colored solid.

Step 4

To an ice-cooled solution of 5-(2-pyrrolidin-1-ylethoxy)benzofuran-2-carboxylic acid methyl ester (960 mg, 3.3 mmol) anhydrous ethylene glycol dimethyl ether (10 ml) was added dropwise degassed aqueous lithium hydroxide solution (2.0 ml, 2.0M). After stirring at room temperature for 4 h, the solution was cooled down and the pH was adjusted to 2 with 4.0 M HCl in dioxane. A gummy tan precipitate formed. The solvent was removed and the gummy residue was frozen and lyophilized. The tan colored solid was dissolved in boiling 2-propanol (90 ml), the solution was filtered hot and then cooled to give 5-(2-pyrrolidin-1-yl-ethoxy)-benzofuran-2-carboxylic acid as beige colored needles (528 mg). Additional 153 mg was obtained from the mother liquor.

Step 5

To a solution of 5-(2-pyrrolidin-1-ylethoxy)benzofuran-2-carboxylic acid (156 mg, 0.50 mmol) and 4-(2-aminoethoxy)benzoic acid methyl ester hydrochloride (129 mg, 0.56 mmol) in DMF (4.5 ml) in a 20 ml vial was added diisopropylethylamine (0.88 ml, 5.1 mmol). A solution of O-(7-azabenzotriazol-1-yl)-1,1,3,3-tetramethyluronium hexafluorophosphate (740 µL, 0.82 M, 0.61 mmol) in DMF was added to give a bright yellow solution. The vial was purged with nitrogen and stirred at room temperature for 18 h. The solution was removed and the residue was dissolved in EtOAc (25 ml) and washed with H$_2$O, 1.0M aqueous K$_2$CO$_3$, and brine. The organic layer was dried over anhydrous MgSO$_4$ and solvent was removed on a rotary evaporator. Purification of the residue by column chromatography on a silica gel column using 93:5:2 CH$_2$Cl$_2$:MeOH:TEA eluent provided 4-{2-[5-(2-pyrrolidin-1-ylethoxy)benzofuran-2-carbonylamino]-ethoxy}-benzoic acid methyl ester as a beige solid (174 mg).

Step 6

To a solution of 4-{2-[5-(2-pyrrolidin-1-ylethoxy)benzofuran-2-carbonylamino]-ethoxy}-benzoic acid methyl ester (169 mg, 0.37 mmol) in methanol (8 ml) and tetrahydrofuran (4 ml) was added hydroxylamine in water (2.9 ml of a 50 wt. % solution) and 4.0 M aqueous solution of sodium hydroxide (0.65 ml). After stirring for 18 h, the organics were removed and the aqueous solution was cooled in an ice/water bath and the pH was adjusted to ~8 with 4.4 ml 1.0 M hydrochloric acid to give precipitates. The heterogeneous solution was warmed to room temperature and acetonitrile was added till the precipitates dissolved. The solution was chromatographed on C-18 reverse phase HPLC. Fractions with absorbance at 214 nm, were collected, frozen, and lyophilize to give the title compound (31 mg). $^1$H NMR (400 MHz, DMSO-d$_6$) δ: 11.05 (s, 1H), 10.4 (s, 1H), 8.91 (s, 2H), 7.70 (d, 2H, J=7.4), 7.59 (dd, 1H, J=3.7, 9.1 Hz), 7.51 (d, 1H, J=3.7 Hz), 7.35 (s, 1H), 7.13 (d, 1H, J=9.0 Hz), 7.00 (d, 2H, J=7.4 Hz), 4.37 (m, 2H), 4.18 (m, 2H), 3.62 (m, 6H), 3.12 (m, 2H), 2.02 (m, 2H), 1.89 (m, 2H). EM (calc.): 453.2; MS (ESI) m/e (M+1H)$^+$: 454.1, (M−1H)$^-$: 452.2.

Example 7

Synthesis of N-hydroxy-4-[2-(3-dimethylaminobenzofuran-2-ylcarbonylamino)-ethoxy]-benzamide hydrochloride

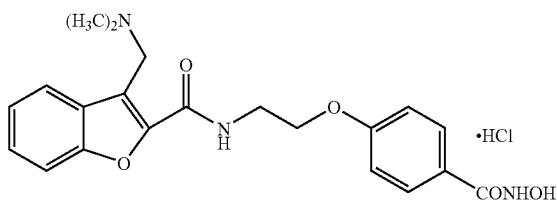

Step 1

(2-Hydroxyethyl)carbamic acid tert-butyl ester (152.0 g, 0.942 mol) and 4-hydroxybenzoic acid methyl ester (174.0 g, 1.12 mol) were dissolved in tetrahydrofuran (2000 ml) and cooled to 0-5° C. Triphenylphosphine (292.8 g 1.116 mol) was added to the cooled mixture. A solution of diisopropyl azodicarboxylate (246.0 g, 1.218 mol) in tetrahydrofuran (400 ml) was added dropwise over a period of one to two hours keeping the reaction temperature below 10° C. After addition, the reaction was allowed to warm slowly to ambient temperature and stirred overnight. After completion of reaction, solvent was distilled under reduced pressure and the resulting oil was dissolved in ethanol (500 ml) and ethyl acetate (2000 ml). Acetyl Chloride (222.0 g, 2.826 mol) was added drop wise over fifteen minutes with the temperature allowed to rise to 40° C. The resulting suspension was stirred at 40° C. until completion of reaction. After completion of reaction, the resulting crystals were filtered on a coarse frit and washed with ethyl Acetate (300 mL). The material is dried in vacuo to give of 4-(2-aminoethoxy)benzoic acid methyl ester hydrochloride (204.1 g) as a white crystalline solid.

Step 2

4-(2-Aminoethoxy)benzoic acid methyl ester hydrochloride (78.90 g, 0.340 mol) and 3-methylbenzofuran-2-carboxylic acid (60.0 g, 0.340 mol) were suspended in acetonitrile (360 ml) and cooled to 0-5° C. Pyridine (137.6 mL, 1.702 mol) was added quickly. A solution of phosphorous oxychloride (52.2 g, 0.340 mol) in acetonitrile (60 ml) was added drop wise over thirty to forty-five minutes with the temperature kept below 20° C. The reaction mixture was allowed to stir for one hour and warm slowly to ambient temperature. After completion of reaction, the solution was added to a rapidly stirred 0-5° C. mixture of chlorobenzene (1000 ml) and 1N hydrochloric acid (1000 ml). The reaction mixture was stirred rapidly and allowed to warm to room temperature. The organic layer was washed with water, 3% potassium hydroxide, and again with water. Chlorobenzene (100 ml) was added to the washed organic layer. Solvent (100 ml) was then distilled at atmospheric pressure until the pot temperature reached 132° C. After cooling to ambient temperature, 4-{2-[(3-methylbenzofuran-2-carbonyl)amino]ethoxy}benzoic acid methyl ester was stored in solution for use in the next step.

Step 3

A solution of 4-{2-[(3-methylbenzofuran-2-carbonyl)amino]ethoxy}benzoic acid methyl ester (0.340 mol) in chlorobenzene (1000 ml) was treated with 2,2'-azobisisobutyronitrile (5.60 g, 0.017 mol) and N-bromosuccinimide (75.76 g, 0.426 mol). The resulting mixture is heated to 80° C. and stirred for one hour. After completion of reaction, the reaction mixture was cooled to ambient temperature and washed with water, 3% sodium hydrogensulfite, and again with water. Solvent was distilled under reduced pressure and after cooling to ambient temperature, dichloromethane was added and to give 4-{2-[(3-bromomethylbenzofuran-2-carbonyl)amino]ethoxy}benzoic acid methyl ester which was used in the next step.

Step 4

A solution of 4-{2-[(3-bromomethylbenzofuran-2-carbonyl)amino]ethoxy}-benzoic acid methyl ester (0.340 mol) in chlorobenzene (200 ml) and dichloromethane (800 ml) was added dropwise to a 0-5° C. solution of 2M dimethylamine in tetrahydrofuran (510 ml, 1.022 mol) over 30 minutes with the temperature below 20° C. The resulting mixture was stirred for one hour and allowed to warm to ambient temperature. After completion of reaction, the reaction mixture was washed with 5% potassium carbonate and water. Solvent was distilled at atmospheric pressure until the pot temperature reached 100° C. After cooling to ~50° C., acetonitrile (400 ml) and ethyl Acetate (400 ml) were added to the pot. The reaction mixture was heated to reflux until all solids dissolved. The reaction mixture was allowed to cool to give 4-{2-[(3-dimethylaminomethyl-benzofuran-2-carbonyl)amino]ethoxy}benzoic acid methyl ester (76.6 g) as an off white powder.

Step 5

4-{2-[(3-Dimethylaminomethylbenzofuran-2-carbonyl)amino]ethoxy}benzoic acid methyl ester (70.0 g, 0.177 mol) was suspended in methanol (350 ml). 50% Potassium hydroxide (139.8 g, 1.062 mol) was added and the reaction mixture was heated to 60° C. until completion of reaction. After cooling to room temperature, the resulting crystals were filtered on a coarse frit and washed with methanol. The crystals were dried in vacuo to give 4-{2-[(3-dimethylaminomethylbenzofuran-2-carbonyl)amino]ethoxy}benzoic acid potassium salt (72.0 g) as a white solid.

Step 6

4-{2-[(3-Dimethylaminomethylbenzofuran-2-carbonyl)amino]ethoxy}benzoic acid potassium salt (20.0 g, 0.0476 mol) was suspended in N,N-Dimethylformamide (100 ml). 4 Molar hydrochloric acid in dioxane (11.9 ml, 0.0476 mol) was added to the suspension. After stirring for thirty minutes at ambient temperature, the reaction mixture was filtered through a medium frit. 1-[3-(Dimethylamino)propyl]-3-ethylcarbodiimide hydrochloride (10.94 g, 0.0571 mol) and 1-hydroxybenzotriazole (7.71 g, 0.0571 mol) were added to the solution and the reaction mixture was stirred one hour at ambient temperature. In a separate pot, hydroxylamine hydrochloride (13.2 g, 1.904 mol) was suspended in N,N-dimethylformamide (100 ml) and treated with triethylamine (33.1 ml, 2.380 mol). After stirring the reaction mixture for 1 h, the salt was filtered off and the resulting solution was added to the above activated acid solution and stirred at ambient temperature until completion of reaction. After the product began to crystallize, methanol (150 ml) was added slowly over thirty min. The reaction mixture was stirred for 1 h at ambient temperature then cooled to 0-5° C. and stirred another hour. The crystals were filtered and washed with methanol (40 ml) before being dried in vacuo to give 3-dimethylaminomethylbenzofuran-2-carboxylic acid [2-(4-hydroxy-carbamoylphenoxy)ethyl]amide (11.88 g) as a white solid. The crude material (13.25 g, 0.033 mol) was suspended in N,N-dimethylformamide (80 ml) and heated to 100° C. to give a solution. After cooling, ethanol (80 ml) was added drop-wise over thirty minutes and the resulting suspension was allowed to cool for an hour. The crystals were filtered and washed with ethanol (40 ml) and dried to give pure product (9.82 g) as a white solid.

Step 7

N-hydroxy-4-[2-(3-dimethylaminobenzofuran-2-ylcarbonylamino)ethoxy]-benzamide (22.7 g, 0.057 mol) was suspended in 2-propanol (220 ml). 12 M HCl (5.2 ml, 0.063 mol) was added in one portion and the resulting mixture was heated to reflux. Water (44 ml) was added dropwise until a homogenous solution was obtained. The reaction mixture was allowed to cool and crystallize overnight. After cooling below 5° C. for one h, the crystals were filtered and washed with 2-propanol before being dried in vacuo to give the title compound (22.0 g) as a white solid.

Example 8

Synthesis of N-hydroxy-4-[2-(benzofuran-2-ylcarbonylamino)ethylsulfanyl]-benzamide

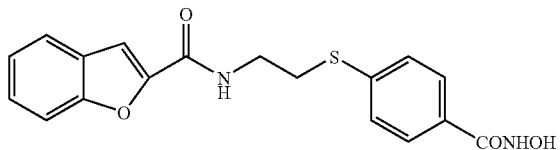

Step 1

To a solution of diisopropyl azodicarboxylate (DIAD, 4.04 g, 20 mmol) in THF (100 ml) at 0° C. was added triphenylphosphine (5.25 g, 20 mmol). After 1 h, a solution of Boc-ethanolamine (3.22 g, 20 mmol) in THF (10 ml) was added. After 20 min., a solution of methyl 4-mercaptobenzoate (3.86 g, 20 mmol) in THF (10 ml) was added and the reaction mixture was stirred overnight at room temperature. The reaction mixture was concentrated and ethyl acetate (150 ml) was added. The solution was washed with 1M HCl, saturated aqueous NaHCO₃, brine, dried over MgSO₄, filtered, and evaporated to dryness. The oily yellow residue was eluted through a plug of silica gel (0-20 ethyl acetate in hexane as mobile phase) and the product was then recrystallized from ether and hexane to give methyl 4-(2-tert-butoxycarbonylaminoethylsulfanyl)benzoate (4.00 g).

Step 2

A solution of methyl 4-(2-tert-butoxycarbonylaminoethylsulfanyl)benzoate (1.00 g, 3.21 mmol) in dichloromethane (8 ml) was treated with a solution of HCl in dioxane (4M, 8 ml, 10 eq.) at room temperature for 3 h. Ether (100 ml) was added and the mixture was filtered, washed with ether and pumped dry to give methyl 4-(2-aminoethylsulfanyl)benzoate hydrochloride.

Step 3

Methyl 4-(2-aminoethylsulfanyl)benzoate hydrochloride (0.248 g, 1.00 mmol), was combined with benzofuran-2-carboxylic acid (0.162 g, 1.00 mmol) and HBTU (0.379 g, 1.00 mmol) in DMF (5 ml) at room temperature. Triethylamine (0.307 ml, 2.2 mmol) was added and the reaction mixture was stirred at room temperature overnight. Saturated aqueous NaHCO₃ (15 ml) was added to give precipitates which was broken up by the addition of water (20 ml). The solid was filtered and the cake was dissolved in ethyl acetate. The residual water was removed by pipette and hexane was added to give methyl 4-{2-[(benzofuran-2-ylcarbonyl)-amino]ethylsulfanyl}benzoate (0.138 g) as a gum which was used in the next step without further purification.

Step 4

To a solution of methyl 4-{2-[(benzofuran-2-yl-carbonyl)amino]ethylsulfanyl}-benzoate in THF (2 ml) was added a solution of 50% hydroxylamine in water (4 ml). Methanol (2 ml) and 0.1 M NaOH (0.1 ml) were added. The reaction mixture was stirred for three days at room temperature. The solvents were evaporated and the residue was crystallized from dichloromethane/ethyl acetate, to give the title compound (46 mg).

¹H NMR (DMSO-d⁶): 3.12 (2H, m); 3.5 (2H, m); 7.33 (1H, t); 7.42 (2H, d); 7.45 (1H, m*); 7.53 (1H, s); 7.62 (1H, d); 7.7 (2H, d); 7.78 (1H, d); 8.96 (1H, t); 8.99 (1H, br. s). MS (M+1): 357.

Example 9

Synthesis of N-hydroxy-4-[2-(benzofuran-2-ylcarbonylamino)ethylsulfonyl]-benzamide

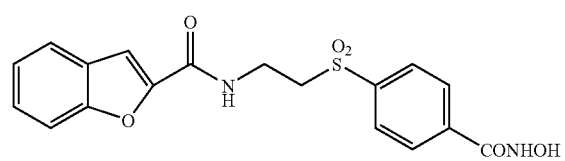

Step 1

To a solution of methyl 4-(2-tert-butoxycarbonylaminoethylsulfanyl)-benzoate (3.00 g, 9.63 mmol) in methanol/water (1:1, 100 ml) was added Oxone® (13.03 g, 21.19 mmol). After 48 h, methanol was removed under reduced pressure, and the residue was partitioned between ethyl acetate (150 ml) and saturated aqueous NaHCO₃ (150 ml). The organic phase was washed with brine (100 ml), dried over MgSO₄, filtered, concentrated in vacuo, and the residue was recrystallized from ethyl acetate/hexane to give methyl 4-(2-tert-butoxycarbonylamino-ethanesulfonyl)benzoate (2.86 g) of the product.

Step 2

A solution of methyl 4-(2-tert-butoxycarbonylaminoethanesulfonyl)benzoate (2.86 g, 8.33 mmol) in dichloromethane (20 ml) was treated with 4M HCl in dioxane (20 ml) for 2 h. Ether (200 ml) was added and the suspension was filtered, washed with ether (2×50 ml), hexane (50 ml) and pumped dry to give methyl 4-(2-aminoethylsulfonyl)benzoate hydrochloride (2.23 g) which was coupled with benzofuran 2-carboxylic acid as described above to afford the title compound. MS (M+1): 388.

Proceeding as described in Example 1-3 above but using appropriate commercially available starting materials the following compounds of Table I-IV were prepared.

TABLE 1

Cpd. 1

¹H NMR(400MHz, DMSO-d₆) δ 8.69(t, J=5.8Hz, 1H), 7.83(d, J=7.5Hz, 2H), 7.69(d, J=9.1Hz, 2H), 7.46(m, 3H), 6.99(d, J=9.1Hz, 2H), 4.16(t, J=5.8Hz, 2H), 3.63(q, J=5.8Hz, 2H). EM(calc.): 300.1; MS(ESI) m/e: 301.1(M−1)⁺, 299.0(M+1)⁻.

TABLE 1-continued

Cpd. 2

$^1$H NMR(400MHz, DMSO-d$_6$) δ 11.08(s, 1H), 8.92(s, 1H), 8.41(t, J=6Hz, 1H), 7.74(d, J=8.8Hz, 2H), 7.58(d, J=6.8Hz, 2H), 7.46(d, J=15.6Hz, 1H), 7.45-7.37(m, 3H), 7.03(d, J=8.8Hz, 2H0, 6.72(d, J=15.6Hz, 1H), 4.13(t, J=5.2Hz, 2H), 3.60(q, J=5.6Hz, 2H). EM(calc.): 326.1; MS(ESI) m/e(M+1H)$^+$: 327.1, (M−1H)$^-$: 325.2.

Cpd. 3

$^1$H NMR(400MHz, DMSO-d$_6$) δ 11.07(s, 1H), 8.91(s, 1H), 8.42(t, J=4.8Hz, 1H), 7.72(d, J=8.4Hz, 2H), 7.27(t, J=7.2Hz, 2.0Hz), 7.18(t, J=7.2Hz, 1H), 7.13(d, J=7.2Hz, 2H), 7.01(d, J=8.8Hz, 2H), 4.07(t, J=5.6Hz, 2H), 3.49(dq, J$_1$=5.6Hz, J$_2$=1.6Hz, 2H), 2.28(ddd, J$_1$=4.0Hz, J$_2$=5.6Hz, J$_3$=9.6Hz, 1H), 1.95(ddd, J$_1$=4.1Hz, J$_2$=5.2Hz, J$_3$=8.4Hz, 1H), 1.39(ddd, J$_1$=4.0Hz, J$_2$=5.2Hz, J$_3$=9.2Hz, 1H), 1.24(ddd, J$_1$=4.0Hz, J$_2$=6.4Hz, J$_3$=10.4Hz, 1H). EM(calc.): 340.1; MS(ESI) m/e(M+1H)$^+$: 341.2, (M−1H)$^-$: 339.2.

Cpd. 4

$^1$H NMR(400MHz, DMSO-d$_6$) δ 11.08(s, 1H), 8.92(s, 1H), 8.31(t, J=5.6Hz, 1H), 7.73(d, J=9.2Hz, 2H), 7.52(d, J=9.2Hz, 2H), 7.41(d, J=15.6Hz, 1H), 7.03(d, J=8.8Hz, 2H), 6.99(d, J=8.8Hz, 2H), 6.55(d, J=15.6Hz, 1H), 4.12(t, J=5.6Hz, 2H), 3.81(s, 3H), 3.58(q, J=5.6Hz, 2H). EM(calc.): 356.1; MS(ESI) m/e(M+1H)$^+$: 357.2, (M−1H)$^-$: 355.2.

Cpd. 5

$^1$H NMR(400MHz, DMSO-d$_6$) δ 10.96(s, 1H), 8.80(s, 1H), 8.01(t, J=4.8Hz, 1H), 7.61(d, J=8.8Hz, 2H), 7.14-7.02(m, 5H), 6.86(d, J=8.8Hz, 2H), 3.32(q, J=5.6Hz, 2H), 2.71(t, J=7.2, 2H), 2.30(t, J=7.6Hz, 2H). EM(calc.): 328.1; MS(ESI) m/e (M+1H)$^+$: 329.2, (M−1H)$^-$: 327.0.

Cpd. 6

$^1$H NMR(400MHz, DMSO-d$_6$) δ 11.11(s, 1H), 10.89(s, 1H), 8.95(br s, 1H), 8.22(t, J=5.6Hz, 1H), 7.76(d, J=8.8Hz, 2H), 7.56(d, J=8.0Hz, 1H), 7.37(d, J=8.4Hz, 1H), 7.22(d, J=2.0Hz, 1H), 7.08(t, J=7.6Hz, 1H), 7.02(d, J=8.4Hz, 2H), 6.93(t, J=8.4Hz, 1H), 4.09(pseudo t, J=6.0Hz, 2H), 3.58(s, 2H), 3.50(pseudo q, J=5.6Hz, 2H). EM (calc.): 353.1; MS(ESI) m/e(M+1H)$^+$: 353.9, (M−1H)$^-$: 252.0.

Cpd. 7

$^1$H NMR(400MHz, DMSO-d$_6$) δ 11.11(s, 1H), 8.80(t, J=5.6Hz, 1H), 7.82(d, J=7.6Hz, 1H), 7.81(d, J=8.0Hz, 1H), 7.76(d, J=8.4Hz, 2H), 7.19(t, J$_1$=5.2Hz, 1H), 7.06(d, J=8.8Hz, 2H), 4.21(pseudo t, J=6.0Hz, 2H), 3.67(pseudo q, J=5.6Hz, 2H). EM (calc.): 306.1; MS(ESI) m/e(M+1H)$^+$: 307.0, (M−1H)$^-$: 304.9.

Cpd. 8

$^1$H NMR(400MHz, DMSO-d$_6$) δ 8.98(s, 1H), 8.9(t, J=5.4Hz, 1H), 8.67(d, J=4.6Hz, 1H), 8.16(d, J=8.1Hz, 1H), 7.69(d, J=8.9Hz, 2H), 7.48(m, 1H), 6.99(d, J=8.9Hz, 2H), 4.17(t, J=5.4Hz, 2H), 3.65(m, 2H). EM(calc.): 301.11; MS(ESI) m/e(M−1H)$^-$: 300.0.

Cpd. 9

$^1$H NMR(400MHz, DMSO-d$_6$) δ 11.03(1H, s), 8.87(1H, bs), 8.74(1H, t, J=5.6Hz), 7.93(2H, d, J=8.0Hz), 7.75(2H, d, J=8.0Hz), 7.69(3H, m), 7.47(1H, t, J=8.0Hz), 7.39(2H, m), 6.99(2H, d, J=8.9Hz), 4.18(2H, t, J=5.6Hz), 3.66(2H, m). EM(calc.): 376.41; MS(ESI) m/e(M+1H)$^+$: 377.1, (M−1H)$^-$: 375.0.

Cpd. 10

EM(calc.): 376.1; MS(ESI) m/e(M+1)$^+$: 376.9, (M−1)$^-$: 375.1.

Cpd. 11

$^1$H NMR(400MHz, DMSO-d$_6$) δ 11.11(s, 1H0, 8.95(s, 1H), 8.84(t, J=6.0Hz, 1H), 7.83(d, J=4.0Hz, 1H), 7.77(d, J=9.2Hz, 2H), 7.75(d, J=7.2Hz, 2H), 7.59(d, J=4.0Hz, 1H), 7.49(pseudo t, J=7.2Hz, 2H), 7.41(pseudo t, J=7.6Hz, 1H), 7.07(d, J=8.8Hz, 2H), 4.22(pseudo t, J=5.6Hz, 2H), 3.69(pseudo q, J=5.2Hz, 2H). EM(calc.): 382.1; MS(ESI) m/e(M+1H)$^+$: 383.1, (M−1H)$^-$: 381.0.

Cpd. 12

$^1$H NMR(400MHz, DMSO-d$_6$) δ 11.05(s, 1H), 10.15(s, 1H), 8.36(t, J=5.6Hz, 1H), 7.70(d, J=8.8Hz, 2H), 7.32(m, 1H), 6.97(d, J=8.8Hz, 2H), 6.92(m, 1H), 6.88(m, 1H), 4.04(t, J=5.6Hz, 2H), 3.66(s, 2H), 3.45(m, 2H). EM(calc.): 320.1; MS(ESI) m/e (M+1H)$^+$: 320.9, (M−1H)$^-$: 319.0.

Cpd. 13

$^1$H NMR(400MHz, DMSO-d$_6$) δ 11.04(s, 1H), 8.87(m, 2H), 8.45(s, 1H), 7.97(m, 4H), 7.71(d, J=8.8Hz, 2H), 7.59(m, 2H), 7.02(d, J=8.8Hz, 2H), 4.21(t, J=5.6Hz, 2H), 3.71(m, 2H). EM(calc.): 350.1; MS(ESI) m/e(M+1H)$^+$: 350.9, (M−1H)$^-$: 349.1.

TABLE 1-continued

Cpd. 14

$^1$H NMR(400MHz, DMSO-d$_6$) δ 11.04(s, 1H), 8.98(m, 2H), 8.52(m, 2H),
8.19(d, J=8.8Hz, 1H), 8.08(d, J=8.8Hz, 1H), 7.71(d, J=8.8Hz, 2H), 7.62(m, 1H),
7.02(d, J=8.8Hz, 2H), 4.22(t, J=5.6Hz, 2H), 3.72(m, 2H). EM(calc.): 351.1; MS(ESI) m/e
(M+1H)$^+$: 351.8, (M−1H)$^−$: 349.9.

Cpd. 15

EM(calc.): 383.1; MS(ESI) m/e(M+1)$^+$: 383.9, (M−1)$^−$: 382.2.

Cpd. 16

$^1$H NMR(400MHz, DMSO-d$_6$) δ 11.04(s, 1H), 8.88(s, 1H), 8.61(t, J=4.8Hz,
1H), 7.78(d, J=8.4Hz, 2H), 7.70(d, J=8.8Hz, 2H), 7.46(d, J=8.8Hz, 2H), 6.99(d, J=8.6Hz,
2H), 4.15(t, J=5.6Hz, 2H), 3.62(m, 2H), 1.29(s, 9H). EM(calc.): 356.2; MS
(ESI) m/e(M+1H)$^+$: 357.0, (M−1H)$^−$: 355.1.

Cpd. 17

$^1$H NMR(400MHz, DMSO-d$_6$) δ 11.06(s, 1H), 8.95(s, 1H), 8.72(d, J=5.2Hz,
1H), 8.56(t, J=4.8Hz, 1H), 8.40(d, J=7.6Hz, 1H), 7.80(m, 1H), 7.71(d, J=8.8Hz,
2H), 7.55(d, J=16.0Hz, 1H), 7.00(d, J=8.8Hz, 2H), 6.90(d, J=16.0Hz, 1H), 4.12(t, J=5.6Hz,
2H), 3.59(m, 2H). EM(calc.): 327.1; MS(ESI) m/e(M+1H)$^+$: 328.1, (M−1H)$^−$: 326.1.

Cpd. 18

$^1$H NMR(400MHz, DMSO-d$_6$) δ 11.04(s, 1H), 8.88(s, 1H), 8.73(t, J=5.6Hz,
1H), 7.93(d, J=9.2Hz, 2H), 7.69(m, 4H), 7.47(t, J=2.4Hz, 2H), 7.01(d, J=9.2Hz,
2H), 6.29(t, J=2.4Hz, 2H), 4.18(t, J=5.6Hz, 2H), 3.66(m, 2H). EM(calc.): 365.1; MS
(ESI) m/e(M+1H)$^+$: 366.0, (M−1H)$^−$: 364.2.

Cpd. 19

$^1$H NMR(400MHz, DMSO-d$_6$) δ 11.04(s, 1H), 8.53(t, J=5.6Hz, 1H),
7.80(d, J=9.2Hz, 2H), 7.70(d, J=9.2Hz, 2H), 6.99(m, 4H), 5.95(m, 1H), 5.80(m, 1H), 4.96(s,
1H), 4.14(t, J=5.6Hz, 2H), 3.60(m, 2H), 2.00(m, 3H), 1.72(m, 3H). EM(calc.): 396.2; MS
(ESI) m/e(M+1H)$^+$: 397.1, (M−1H)$^−$: 395.2.

Cpd. 20

$^1$H NMR(400MHz, DMSO-d$_6$) δ 11.08(s, 1H), 9.35(t, J=5.6Hz, 1H),
8.25(d, J=7.6Hz, 1H), 8.15(d, J=8.0Hz, 1H), 7.73(d, J=8.8Hz, 2H), 7.68-7.58(m, 2H),
7.03(d, J=9.2Hz, 2H), 4.23(pseudo t, J=6.4Hz, 2H), 3.74(pseudo q, J=6.0Hz, 2H). EM
(calc.): 357.1; MS(ESI) m/e(M+1H)$^+$: 358.1, (M−1H)$^−$: 356.0.

Cpd. 21

$^1$H NMR(400MHz, DMSO-d$_6$) δ 11.07(s, 1H), 9.47(t, J=5.6 Ha, 1H),
7.90(pseudo t, J=9.2Hz, 2H), 7.73(d, J=8.8Hz, 2H), 4.59(td, J$_1$=7.6Hz, J$_2$=0.8Hz, 1H),
7.52(td, J$_2$=8.0Hz, J$_2$=1.2Hz, 1H), 7.03(d, J=8.8Hz, 2H), 4.24(t, J=6.0Hz, 2H),
3.72(pseudo q, J=6.0Hz, 2H). EM(calc.): 341.1; MS(ESI) m/e(M+1H)$^+$: 342.1, (M−1H)$^−$:
340.2.

Cpd. 22

$^1$H NMR(400MHz, DMSO-d$_6$) δ 11.08(s, 1H), 9.70(s, 1H), 8.91, (t, J=5.6Hz,
1H), 7.72(d, J=8.4Hz, 2H), 6.97(d, J=8.4Hz, 2H), 4.10(m, 2H), 3.93(m, 2H),
3.54(m, 2H), 3.27(m, 2H), 3.08(m, 2H), 2.21(m, 1H), 2.01(m, 1H), 1.51(m, 10H). EM(calc.):
375.2; MS(ESI) m/e(M+1H)$^+$: 376.1, (M−1H)$^−$: 374.1.

Cpd. 23

$^1$H NMR(400MHz, DMSO-d$_6$) δ 11.09(s, 1H), 8.35(d, J=6.8Hz, 2H),
7.72(d, J=9.2Hz, 2H), 7.25(d, J=6.8Hz, 2H), 6.98(d, J=9.2Hz, 2H), 4.10(t, J=5.6Hz, 2H),
3.97(m, 2H), 3.54(m, 10H). EM(calc.): 399.2; MS(ESI) m/e(M+1H)$^+$: 400.1, (M−1H)$^−$:
398.1.

Cpd. 24

EM(calc.): 290.1; MS(ESI) m/e(M+1)$^+$: 291.1, (M−1)$^−$: 289.2.

Cpd. 25

EM(calc.): 377.1; MS(ESI) m/e(M+1)$^+$: 377.9, (M−1)$^−$: 376.0.

Cpd. 26

EM(calc.): 377.1; MS(ESI) m/e(M+1)$^+$: 378.0, (M−1)$^−$: 375.9.

Cpd. 27

$^1$H NMR(400MHz, DMSO-d$_6$) δ 11.04(s, 1H), 9.11(t, J=5.6Hz, 1H),
7.70(d, J=9.2Hz, 2H), 7.62(m, 2H), 7.29(m, 2H), 7.01(d, J=9.2Hz, 2H), 4.21(t, J=5.6Hz,
2H), 3.71(m, 2H). EM(calc.): 340.1; MS(ESI) m/e(M+1H)$^+$: 341.0, (M−1H)$^−$: 339.1.

Cpd. 28

EM(calc.): 289.1; MS(ESI) m/e(M+1H)$^+$: 290.0, (M−1H)$^−$: 287.8.

Cpd. 29

$^1$H NMR(400MHz, DMSO-d$_6$) δ 11.04(s 1H), 10.43(s, 1H), 8.62(t, J=6.0Hz,
1H), 7.94(d, J=6.4Hz, 2H), 7.853(m, 4H), 7.70(d, J=9.2Hz, 2H), 7.60(m, 1H),

TABLE 1-continued 7.52(m, 2H), 7.00(d, J=9.2Hz, 2H), 4.16(t, J=6.0Hz, 2H), 3.63(dt, J$_1$=5.6Hz, J$_2$=6.0Hz, 2H). EM(calc.): 419.2; MS(ESI) m/e(M+1H)$^+$: 420.2, (M−1H)$^−$: 418.3.
Cpd. 30

$^1$H NMR(400MHz, DMSO-d$_6$) δ 11.04(s, 1H), 9.23(t, J=6.0Hz, 1H), 9.01(s, 1H), 8.89(d, J=6.8Hz, 2H), 8.38(d, J=6.4Hz, 2H), 7.70(d, J=9.2Hz, 2H), 7.00(d, J=9.2Hz, 2H), 4.22(t, J=5.6Hz, 2H), 3.71(m, 2H). EM(calc.): 384.1; MS(ESI) m/e (M+1H)$^+$: 384.9, (M−1H)$^−$: 382.9.
Cpd. 31

$^1$H NMR(400MHz, DMSO-d$_6$) δ 11.04(s, 1H), 7.69(d, J=8.4Hz, 2H), 7.56(t, J=5.6Hz, 1H), 7.01(d, J=8.8Hz, 2H), 4.01(t, J=5.6Hz, 2H), 3.40(m, 2H), 1.95(m, 3H), 1.69(m, 12H). EM(calc.): 358.2; MS(ESI) m/e(M+1H)$^+$: 358.9, (M−1H)$^−$: 357.2.
Cpd. 32

EM(calc.): 336.09; MS(ESI) m/e(M−1H)$^−$: 335.3.
Cpd. 33

EM(calc.): 370.12; MS(ESI) m/e(M−1H)$^−$: 369.0.
Cpd. 34

EM(calc.): 344.10; MS(ESI) m/e(M+1H)$^+$: 345.0, (M−1H)$^−$: 343.1.
Cpd. 35

EM(calc.): 360.13; MS(ESI) m/e(M−1H)$^−$: 359.1.
Cpd. 36

EM(calc.): 344.10; MS(ESI) m/e(M−1H)$^−$: 358.8.
Cpd. 37

EM(calc.): 336.09; MS(ESI) m/e(M+1H)$^+$: 337.2, (M−1H)$^−$: 335.0.
Cpd. 38

EM(calc.): 328.14; MS(ESI) m/e(M+1H)$^+$: 329.2, (M−1H)$^−$: 327.2.
Cpd. 39

EM(calc.): 368.03; MS(ESI) m/e(M−1H)$^−$: 367.0.
Cpd. 40

EM(calc.): 328.14; MS(ESI) m/e(M+1H)$^+$: 328.8, (M−1H)$^−$: 327.2.
Cpd. 41

EM(calc.): 364.08; MS(ESI) m/e(M+1H)$^+$: 365.1, (M−1H)$^−$: 363.2.
Cpd. 42

EM(calc.): 344.14; MS(ESI) m/e(M+1H)$^+$: 345.1, (M−1H)$^−$: 343.1.
Cpd. 43

EM(calc.): 344.14; MS(ESI) m/e(M+1H)$^+$: 345.0, (M−1H)$^−$: 343.2.
Cpd. 44

EM(calc.): 348.11; MS(ESI) m/e(M+1H)$^+$: 348.8, (M−1H)$^−$: 346.9.
Cpd. 45

EM(calc.): 412.11; MS(ESI) m/e(M+1H)$^+$: 413.3, (M−1H)$^−$: 411.0.
Cpd. 46

EM(calc.): 412.11; MS(ESI) m/e(M+1H)$^+$: 413.2, (M−1H)$^−$: 411.1.
Cpd. 47

EM(calc.): 376.14; MS(ESI) m/e(M+1H)$^+$: 377.0, (M−1H)$^−$: 375.2.
Cpd. 48

EM(calc.): 339.12; MS(ESI) m/e(M+1H)$^+$: 340.1, (M−1H)$^−$: 338.3.
Cpd.49

$^1$H NMR(400MHz, DMSO-d$_6$) δ 11.53(s, 1H), 11.04(s, 1H), 8.12(d, J=7.6Hz, 2H), 8.01(s, 1H), 7.70(d, J=9.2Hz, 2H), 7.40(d, J=8.0,Hz, 1H), 7.10(m, 2H), 7.017(d, J=8.8Hz, 2H), 4.16(t, J=5.6Hz, 2H), 3.64(m, 2H). EM(calc.): 339.1; MS(ESI) m/e (M+1H)$^+$: 340.0, (M−1H)$^−$: 338.1.
Cpd. 50

$^1$H NMR(400MHz, DMSO-d$_6$) δ 9.37(s, 1H), 9.21(t, J=5.2Hz, 1H), 9.02(s, 1H), 8.15(t, J=9.2Hz, 2H), 7.94(m, 1H), 7.74(m, 3H), 7.02(d, J=8.8Hz, 2H), 4.24(t, J=5.6Hz, 2H), 3.75(m, 2H). EM(calc.): 351.1; MS(ESI) m/e(M+1H)$^+$: 352.0, (M−1H)$^−$: 349.9.
Cpd. 51

$^1$H NMR(400MHz, DMSO-d$_6$) δ 11.11(s, 1H) 9.09(d, J=4.4Hz, 1H), 8.70(d, J=7.6Hz, 1H), 8.65(d, J=7.6Hz, 1H), 8.29(d, J=8.0Hz, 1H), 7.79(m, 4H), 7.10(d, J=8.8Hz,

TABLE 1-continued

2H), 4.30(t, J=5.6Hz, 2H), 3.89(m, 2H). EM(calc.): 351.1; MS(ESI) m/e
(M+1H)⁺: 352.0, (M−1H)⁻: 349.9.
Cpd. 52

¹H NMR(400MHz, DMSO-d₆) δ 13.57(s, 1H), 11.04(s, 1H), 8.88(s, 1H),
8.53(t, J=5.6Hz, 1H), 8.16(d, J=8.0Hz, 1H), 7.70(d, J=8.8Hz, 2H), 7.60(d, J=8.4Hz,
1H), 7.40(t, J=8.0Hz, 1H), 7.23(t, J=8.0Hz, 1H), 7.01(d, J=8.8Hz, 2H), 4.19(t, J=6.0Hz,
2H), 3.68(m, 2H). EM(calc.): 340.1; MS(ESI) m/e(M+1H)⁺: 341.1, (M−1H)⁻: 339.2.
Cpd. 53

¹H NMR(400MHz, DMSO-d₆) δ 11.04(s, 1H), 8.89(m, 2H), 8.45(s, 1H),
7.93(s, 2H), 7.70(d, J=8.4Hz, 2H), 7.01(d, J=8.8Hz, 2H), 4.20(t, J=5.6Hz, 2H),
3.69(m, 2H). EM(calc.): 341.1; MS(ESI) m/e(M+1H)⁺: 341.8, (M−1H)⁻: 340.0.
Cpd. 54

¹H NMR(400MHz, DMSO-d₆) δ 9.07(s, 1H), 9.24(d, J=8.0Hz, 1H),
8.53(m 1H), 8.03(m, 2H), 7.82(t, J=6.8Hz, 1H), 7.71(m, 3H), 7.03(d, J=8.4Hz, 2H), 4.24(t, J=4.8Hz,
2H), 3.76(m, 2H). EM(calc.): 351.1; MS(ESI) m/e(M+1H)⁺: 351.9, (M−1H)⁻:
350.1.
Cpd. 55

¹H NMR(400MHz, DMSO-d₆) δ 9.39(s, 1H), 9.11(s, 1H), 8.59(s, 1H),
8.25(m, 1H), 7.87(m, 2H), 7.70(m, 2H), 7.02(m, 2H), 4.23(s, 2H), 3.76(s, 2H). EM(calc.):
351.1; MS(ESI) m/e(M+1H)⁺: 351.8, (M−1H)⁻: 349.9.
Cpd. 56

¹H NMR(400MHz, DMSO-d₆) δ 11.04(s, 1H), 9.47(m, 1H), 9.23(m, 1H),
8.19(m, 2H), 7.98(m, 2H), 7.70(d, J=8.8Hz, 2H), 7.02(d, J=8.4Hz, 2H), 4.25(t, J=5.2Hz,
2H), 3.78(m, 2H). EM(calc.): 352.1; MS(ESI) m/e(M+1H)⁺: 352.8, (M−1H)⁻: 350.9.
Cpd. 57

EM(calc.): 350.11; MS(ESI) m/e(M+1H)⁺: 351.1, (M−1H)⁻: 349.1.
Cpd. 58

EM(calc.): 351.12; MS(ESI) m/e(M+1H)⁺: 352.2, (M−1H)⁻: 350.0.
Cpd. 59

EM(calc.): 365.14; MS(ESI) m/e(M+1H)⁺: 366.0, (M−1H)⁻: 364.2.
Cpd. 60

EM(calc.): 368.12; MS(ESI) m/e(M+1H)⁺: 369.0, (M−1H)⁻: 367.1.
Cpd. 61

¹H NMR(400MHz, DMSO-d₆) δ 11.04(s, 1H), 8.88(s, 1H), 8.68(t, J=5.6Hz,
1H), 8.34(s, 1H), 8.14(s, 1H), 7.75(d, J=8.0Hz, 1H), 7.70(d, J=8.4Hz, 2H), 7.61(d, J=8.0Hz,
1H), 7.01(d, J=8.8Hz, 2H), 4.18(t, J=6.0Hz, 2H), 3.66(m, 2H). EM(calc.):
340.1; MS(ESI) m/e(M+1H)⁺: 341.0, (M−1H)⁻: 339.2.
Cpd. 62

¹H NMR(400MHz, DMSO-d₆) δ 11.04(s, 1H), 8.11(m, 2H), 7.98(s, 1H),
7.70(d, J=9.2Hz, 2H), 7.47(d, J=7.6Hz, 1H), 7.20(t, J=8.4Hz, 1H), 7.13(t, J=6.8Hz,
1H), 7.01(d, J=9.2Hz, 2H), 4.15(t, J=6.0Hz, 2H), 3.82(s, 3H), 3.62(m, 2H). EM(calc.):
353.1; MS(ESI) m/e(M+1H)⁺: 354.0, (M−1H)⁻: 351.9.
Cpd. 63

¹H NMR(400MHz, DMSO-d₆) δ 11.05(s, 1H), 9.14(t, J=5.6Hz, 1H),
8.19(d, J=8.4Hz, 1H), 8.08(d, J=8.4Hz, 1H), 7.85(t, J=8.4Hz, 1H), 7.69(m, 4H), 7.03(d, J=8.8Hz,
2H), 4.24(t, J=6.0Hz, 2H), 4.15(s, 3H), 3.78(m, 2H). EM(calc.): 381.1; MS(ESI)
m/e(M+1H)⁺: 381.9, (M−1H)⁻: 380.1.
Cpd. 64

EM(calc.): 380.14; MS(ESI) m/e(M+1H)⁺: 381.0, (M−1H)⁻: 379.0.
Cpd. 65

EM(calc.): 380.14; MS(ESI) m/e(M+1H)⁺: 381.2, (M−1H)⁻: 378.9.
Cpd. 66

EM(calc.): 351.12; MS(ESI) m/e(M+1H)⁺: 352.0, (M−1H)⁻: 350.0.
Cpd. 67

¹H NMR(400MHz, DMSO-d₆) δ 11.05(s, 1H), 8.26(t, J=5.6Hz, 1H),
7.70(d, J=8.8Hz, 2H), 7.41-7.35(m, 4H), 7.29(m, 1H), 7.21(s, 1H), 7.00(d, J=9.2, 2H),
4.12(t, J=6.0Hz, 2H), 3.54(pseudo q, J=6.0Hz, 2H), 2.01(s, 3H). EM(calc.): 340.1; MS(ESI)
m/e M+1H)⁺: 340.9, (M−1H)⁻: 339.2.
Cpd. 68

¹H NMR(400MHz, DMSO-d₆) δ 11.08(s, 1H), 10.72(br s, 1H), 8.81(t, J=5.2Hz,
1H), 7.94(dd, J₁=8.4Hz, J₂=2.0Hz, 1H), 7.73(d, J=8.8Hz, 2H), 7.32(s, 1H),

TABLE 1-continued 7.03(d, J=9.2Hz, 2H), 4.60(s, 2H), 4.13(pseudo t, J=5.6Hz, 2H), 3.70(pseudo q, J=5.2Hz, 2H), 2.83(s, 6H). EM(calc.): 397.2; MS(ESI) m/e(M+1H)$^+$: 398.1, (M−1H)$^-$: 396.0.
Cpd. 71

$^1$H NMR(DMSO-d$_6$): 0.92(3H, t, 7Hz); 1.53(1H, m); 1.72(1H, m); 2.48(3H, s); 3.94(1H, m); 4.03(2H, m); 6.62(1H, s); 6.78(1H, dd); 6.92(1H, d); 7.01(2H, d); 7.08(1H, s); 7.31(1H, d); 7.7(2H, d); 8.27(2H, d, 7Hz); 9.25(1H, s). MS(M+1): 425.
Cpd. 72

$^1$H NMR(DMSO-d$_6$): 0.90(2H, dd); 0.91(3H, t, 7Hz); 1.1(2H, br. S); 1.52(1H, m); 1.68(1H, m); 1.92(1H, m); 2.0-2.1(3H, m*); 2.25(1H, m); 2.48(3H, s); 3.24(1H, m); 3.37(4H, m); 3.54(1H, m); 3.95(1H, m); 4.03(2H, m); 6.66(1H, s); 6.97(1H, m); 6.99(2H, d, 9Hz); 7.07(1H, dd, 9, 2Hz); 7.12(1H, d, 6Hz); 7.28(1H, dd, 20, 2Hz); 7.45(1H, t, 9Hz); 7.7(2H, d, 9Hz); 8.29(1H, d, 8Hz). MS(M+1): 548.
Cpd. 73

$^1$H NMR(DMSO-d$_6$): 2.00(2H, m); 2.64(1H, m); 2.75(1H, m); 4.1(1H, m); 4.18(1H, m); 4.39(1H, m); 6.98(2H, d, 9Hz); 7.14(1H, m); 7.19-7.28(5H, m); 7.32(1H, t, 8Hz); 7.45(1H, m); 7.58(1H, s); 7.65(1H, d, 7Hz); 7.68(2H, d, 9Hz); 7.76(1H, d, J=7Hz) 8.74(1H, d, 7Hz). MS(M−1): 443.
Cpd. 78

$^1$H NMR(DMSO-d$_6$): 3.56(2H, m); 4.15(1H, m); 4.23(1H, m); 4.57(2H, s); 4.94(1H, m); 6.99(2H, d, 9Hz); 7.33(1H, t, 7Hz); 7.38(5H, s); 7.47(1H, t, 7Hz) 7.58(1H, s); 7.65(1H, d, 8Hz); 7.70(2H, d, 9Hz); 7.77(1H, d, 8Hz); 8.90(1H, s); 9.0(1H, d, 8Hz). MS(M+1): 509.
Cpd. 79

$^1$H NMR(DMSO-d$_6$): 2.7-2.81(2H, m); 3.78(2H, s); 4.12(1H, dd, 10.5Hz); 4.22(1H, dd, 10.7Hz); 4.51(1H, m); 6.97(2H, d, 9Hz); 7.22(1H, m); 7.28(2H, m); 7.29(2H, s); 7.33(1H, t, 7Hz); 7.46(1H, td, 7.1Hz); 7.58(1H, s); 7.65(1H, d, 8Hz); 7.70(2H, d, 9Hz); 7.77(2H, d, 8Hz); 8.79(1H, d, 8Hz). MS(M+1): 475.
Cpd. 80

$^1$H NMR(DMSO-d$_6$): 2.47(3H, d, 1Hz); 3.57-3.62(3H, m); 3.77(3H, s); 4.08(1H, t, 6Hz); 6.64(1H, s); 6.92(1H, dd, 9, 3Hz); 6.99(2H, d, 9Hz); 7.12-7.15(2H, s+d); 7.42(1H, d, 9Hz); 7.7(2H, d, 9Hz); 8.49(1H, t, 6Hz); 8.88(1H, s). MS(M+1): 411.
Cpd. 91

$^1$H NMR(400MHz, DMSO-d$_6$) δ 11.07(s, 1H), 8.91(s, 1H), 8.24(t, J=5.6Hz, 1H), 7.73(d, J=9.2Hz, 2H), 7.57(d, J=6.8Hz, 2H), 7.44(d, J=16.0Hz, 1H, buried under m at 7.41), 7.41(m, 3H), 7.00(d, J=8.8Hz, 2H), 6.63(d, J=16.0Hz, 1H), 4.10(pseudo t, J=6.0Hz, 2H), 3.37(pseudo q, J=6.4Hz, 2H), 1.96(pseudo p, J=6.4Hz, 2H). EM(calc.): 340.1; MS(ESI) m/e(M+1H)$^+$: 341.2, (M−1H)$^-$: 339.3.
Cpd. 92

$^1$H NMR(400MHz, DMSO-d$_6$) δ 11.07(s, 1H), 8.15(s, 1H), 7.73(d, J=8.4Hz, 2H), 7.51(d, J=8.4Hz, 2H), 7.38(d, J=15.6Hz, 1H), 6.99(m, 4H), 6.48(d, J=15.6Hz, 1H), 4.09(pseudo t, J=6.0Hz, 2H), 3.80(s, 3H), 3.35(pseudo q, J=5.2Hz, 2H), 1.94(pseudo q, J=6.0Hz, 2H). EM(calc.): 370.2; MS(ESI) m/e(M+1H)$^+$: 371.0, (M−1H)$^-$: 368.9.
Cpd. 93

$^1$H NMR(400MHz, DMSO-d$_6$) δ 10.96(s, 1H), 8.90(t, J=5.6Hz, 1H), 8.31(s, 1H), 7.98(dd, J$_1$=7.2Hz, J$_2$=1.6Hz, 2H), 7.62(d, J=8.4Hz, 2H), 7.40(pseudo t, J=7.2Hz, 2H), 7.31(pseudo tt, J$_1$=7.2Hz, J$_2$=2.0Hz, 1H), 6.90(d, J=9.2Hz, 2H), 4.03(t, J=5.6Hz, 2H), 3.42(pseudo q, J=6.0Hz, 2H), 1.98(pseudo p, J=6.0Hz, 2H). EM(calc.): 397.1; MS(ESI) m/e(M+1H)$^+$: 397.9, (M−1H)$^-$: 396.0.
Cpd. 94

$^1$H NMR(400MHz, DMSO-d$_6$) δ 11.09(s, 1H), 8.26(d, J=7.2Hz, 1H), 7.74(d, J=8.4Hz, 2H), 7.58(d, J=7.2Hz, 2H), 7.44(m, 4H), 6.68(d, J=16.4Hz, 1H), 4.27(m, 1H), 4.07(m, 1H), 3.96(m, 1H), 1.25(d, J=6.8Hz, 3H). EM (calc.): 340.1; MS(ESI) m/e(M+1H)$^+$: 341.1, (M−1H)$^-$: 339.1.
Cpd. 95

$^1$H NMR(400MHz, DMSO-d$_6$) δ 11.09(s, 1H), 8.27(d, J=8.0Hz, 1H), 7.74(d, J=8.8Hz, 2H), 7.58(d, J=7.2Hz, 2H), 7.46(d, J=16.0Hz, 1H), 7.42(m, 3H), 7.04(d, J=9.2Hz, 2H), 6.68(d, J=16.4Hz, 1H), 4.27(pseudo p, J=6.8Hz, 1H) 4.07(dd, J$_1$=5.6Hz, J$_2$=10.0Hz, 1H), 3.96(dd, J$_1$=5.6Hz, J$_2$=9.6Hz, 1H), 1.25(d, J=7.2Hz, 3H). EM (calc.): 340.1; MS(ESI) m/e(M+1H)$^+$: 341.1, (M−1H)$^-$: 339.1.
Cpd. 96

$^1$H NMR(400MHz, DMSO-d$_6$) δ 11.05(s, 1H), 8.87(s, 1H), 8.12(d J=8.0Hz, 1H), 7.67(dt, J$_1$=8.8Hz, J$_2$=2.0Hz, 1H), 7.54(dd, J=8.4Hz, J$_2$=1.6Hz, 2H), 7.43-7.33(m, 4H), 6.99(dt J$_1$=9.2Hz, J$_2$=2Hz, 2H), 6.65(d, J=15.6Hz, 1H), 4.26(m, 1H), 4.01(dd, J$_1$=9.6Hz, J$_2$=4.8Hz, 1H), 3.94(dd J$_1$=9.6Hz, J$_2$=5.6Hz, 1H), 1.66(m, 1H), 1.49(m, 2H), 0.91(d J=6.8Hz, 3H), 0.87(d, J=6.4Hz, 3H). EM(calc.): 382.2; MS(ESI) m/e (M+1H)$^+$: 383.0, (M−1H)$^-$: 381.1.

TABLE 1-continued

Cpd. 97

¹H NMR(400MHz, DMSO-d$_6$) δ 10.95(s, 1H), 8.81(s, 1H), 8.05(d, J=8.4Hz, 1H), 7.62(d, J=8.8Hz, 2H), 7.47(d, J=6.8Hz, 2H), 7.37-7.28(m, 4H), 6.92(dt, J$_1$=8.4Hz, J$_2$=1.6Hz, 2H), 6.61(d, J=16Hz, 1H), 4.21(m, 1H), 3.94(m, 1H), 3.86(m, 1H), 1.69(d. J=12.4Hz, 1H), 1.59-1.52(m, 4H), 1.42(t, J=7.2Hz, 2H), 1.28(m, 1H), 1.15-1.05(m, 3H), 090(m, 1H), 0.77(m, 1H). EM(calc.): 422.2; MS(ESI) m/e(M+1H)⁺: 423.2, (M−1H)⁻: 421.2.

Cpd. 98

¹H NMR(400MHz, DMSO-d$_6$) δ 11.03(s, 1H), 8.88(s, 1H), 8.09(d, J=8.4Hz, 1H), 7.69(dt, J$_1$=8.8Hz, J$_2$=2.8Hz, 2H), 7.432-7.32(series m, 4H), 6.99(dt, J$_1$=9.2Hz, J$_2$=2.4Hz, 2H), 6.73(d, J=15.6Hz, 1H), 4.05(s, 3H), 1.98(m, 1H), 0.95(d, J=2.4Hz, 3H), 0.93(d, J=2.4Hz, 3H). EM(calc.): 368.2; MS(ESI) m/e(M+1H)⁺: 368.7, (M−1H)⁻: 367.1.

Cpd. 99

¹H NMR(400MHz, DMSO-d$_6$) δ 11.04(s, 1H), 8.32(d, J=8Hz, 1H), 7.69(d, J=9.2Hz, 2H), 7.53(m, 2H), 7.43-7.34(m, 4H), 7.28-7.22(m, 3H), 7.18(m, 2H), 6.99(d, J=9.2Hz, 2H), 6.63(d, J=16Hz, 1H), 4.38(m, 1H), 4.02(d, J=6.4Hz, 2H), 2.99(m, 1H), 2.88(m, 1H). Missing OH or NH. EM(calc.): 416.2; MS(ESI) m/e(M+1H)⁺: 417.3, (M−1H)⁻: 415.2.

Cpd. 100

¹H NMR(400MHz, DMSO-d$_6$) δ 11.04(s, 1H), 8.78(s, 1H), 8.32(d, J=8Hz, 1H), 7.69(d, J=8.8Hz, 2H), 7.52(dd, J$_1$=8.4Hz, J$_2$=1.6Hz, 2H), 7.41-7.34(m, 4H), 7.28-7.23(m, 4H), 7.19-7.15(m, 1H), 6.99(d, J=9.2Hz, 2H), 6.63(d, J=15.6Hz, 1H), 4.38(m, 1H), 4.01(d, J=4.4Hz, 2H), 2.99(dd, J$_1$=13.6Hz, J$_2$=6Hz, 1H), 2.88(dd, J$_1$=14Hz, J$_2$=8Hz, 1H). EM(calc.): 416.2; MS(ESI) m/e(M+1H)⁺: 417.2, (M−1H)⁻: 415.2.

Cpd. 101

¹H NMR(400MHz, DMSO-d$_6$) δ 11.05(s, 1H), 8.87(s, 1H), 8.12(d, J=8.0Hz, 1H), 7.69(d, J=8.4Hz, 2H), 7.53(d, J=7.2Hz, 2H), 7.43-7.33(m, 4H), 6.99(d, J=9.2Hz, 2H), 6.65(d, J=15.6Hz, 1H), 4.25(m, 1H), 4.01(dd, J=9.6Hz, 4.8Hz, 1H), 3.94(dd J$_1$=9.6Hz, J$_2$=5.6Hz, 1H), 1.66(m, 1H), 11.48(m, 2H), 0.91(d J=6.8Hz, 3H), 0.87(d, J=6.4Hz, 3H). EM(calc.): 382.2; MS(ESI) m/e(M+1H)⁺: 383.2, (M−1H)⁻: 381.2.

Cpd. 102

¹H NMR(400MHz, DMSO-d$_6$) δ 11.03(s, 1H), 8.87(s, 1H), 8.08(d, J=8Hz, 1H), 7.69(d, J=8.8Hz, 2H), 7.55(d, J=1.2Hz, 2H), 7.43-7.32(m, 4H), 6.99(d, J=9.2Hz, 2H), 6.73(d, J=16Hz, 1H), 4.05(s, 3H), 1.98(m, 1H), 0.946(d, J=2Hz, 3H), 0.93(d, J=2.4Hz, 3H). EM(calc.): 368.2; MS(ESI) m/e(M+1H)⁺: 369.1, (M−1H)⁻: 367.1.

Cpd. 103

¹H NMR(400MHz, DMSO-d$_6$) δ 11.04(s, 1H), 8.14(d, J=8.4Hz, 1H), 7.69(dt, J$_1$=8.8Hz, J$_2$=2.8Hz, 2H), 7.54(dd, J$_1$=6.8, J$_2$=1.2Hz, 2H), 7.43-7.32(m, 4H), 6.99(dt, J$_1$=8.8Hz, J$_2$=3.2Hz, 2H), 6.66(d, J=15.6Hz, 1H), 4.16(m, 1H), 4.03(dd, J$_1$=10Hz, J$_2$=5.6Hz, 1H), 3.96(dd, J$_1$=10Hz, J$_2$=5.2Hz, 1H), 1.67(m, 1H), 1.53(m, 1H), 1.36-1.27(m, 4H), 0.87(t, J=6.4Hz, 3H). Missing 1H, NH or OH. EM(calc.): 382.2; MS(ESI) m/e(M+1H)⁺: 383.1, (M−1H)⁻: 381.1.

Cpd. 104

¹H NMR(400MHz, DMSO-d$_6$) δ 10.97(s, 1H), 8.25(d, J=8.4Hz, 1H), 7.64(dt, J$_1$=8.8Hz, J$_2$=2Hz, 2H), 7.46(dd, J$_1$=7.6Hz, J$_2$=2Hz, 2H), 7.34-7.18(series m, 6H), 6.93(dt, J$_1$=9.2Hz, J$_2$=2.8Hz, 2H), 6.54(d, J=15.6Hz, 1H), 4.31(m, 1H), 3.95(d, J=4.8Hz, 2H), 2.93(dd, J$_1$=13.6Hz, J$_2$=5.6Hz, 1H), 2.79(dd, J$_1$=13.6Hz, J$_2$=8.4Hz, 1H). EM(calc.): 450.1; MS(ESI) m/e(M+1H)⁺: 451.2;(M−1H)⁻: 449.2.

Cpd. 105

¹H NMR(400MHz, DMSO-d$_6$) δ 10.97(s, 1H), 8.07(d, J=8Hz, 1H), 7.62(dt, J$_1$=8.8Hz, J$_2$=2.8Hz, 2H), 7.47(dd, J$_1$=8.8Hz, J$_2$=1.6Hz, 2H), 7.34-7.26(series m, 4H), 6.93(dt, J$_1$=8.8Hz, J$_2$=2.8Hz, 2H), 6.61(d, J=15.6Hz, 1H), 4.04(m, 1H), 3.98(dd, J$_1$=15.6Hz, J$_2$=5.6Hz, 1H), 3.90(dd, J$_1$=9.2, J$_2$=5.6Hz, 1H), 1.64(m, 1H), 1.46(m, 1H), 0.85(t, J=6.8Hz, 3H). EM(calc.): 354.2; MS(ESI) m/e(M+1H)⁺: 354.6, (M−1H)⁻: 353.2.

Cpd. 106

¹H NMR(400MHz, DMSO-d$_6$) δ 10.97(s, 1H), 8.07(d, J=8Hz, 1H), 7.62(d J=8.8Hz, 2H), 7.47(dd, J$_1$=6.8Hz, J$_2$=1.6Hz, 2H), 7.35-7.62(series m, 4H), 6.93(dt, J$_1$=9.2, J$_2$=2Hz, 2H), 6.61(d, J=15.6Hz, 1H), 3.98(dd, J$_1$=9.6Hz, J$_2$=5.6Hz, 1H), 3.90(dd, J$_1$=9.6, J$_2$=4.8Hz, 1H), 1.65(m, 1H), 1.49(m, 1H), 0.85(t, J=7.2Hz, 3H). EM(calc.): 354.2; MS(ESI) m/e(M+1H)⁺: 354.8, (M−1H)⁻: 353.1.

Cpd. 107

EM(calc.): 400.49; MS(ESI) m/e(M+1): 401.0, (M−1H): 399.0.

Cpd. 108

EM(calc.): 400.49; MS(ESI) m/e(M+1): 401.1, (M−1): 399.2.

TABLE 1-continued

Cpd. 109

$^1$H NMR(400MHz, DMSO-d$_6$) δ 10.97(s, 1H), 8.80(br s, 1H), 8.73(d, J=8.4Hz, 1H), 7.62(d, J=9.2Hz, 2H), 7.48(d, J=6.8Hz, 2H), 7.38-7.27(series m, 8H), 7.21(t, J=7.2Hz, 1H), 6.93(d, J=8.8, 2H), 6.69(d, J=15.6Hz, 1H), 5.30(dd, J$_1$=13.6Hz, J$_2$=7.6Hz, 1H), 4.19(d, J=6.4Hz, 2H). EM(calc.): 402.2; MS(ESI) m/e(M+1H)$^+$: 403.2, (M−1H)$^-$: 400.9.

Cpd. 110

$^1$H NMR(400MHz, DMSO-d$_6$) δ 10.97(s, 1H), 8.80(br s, 1H), 8.74(d, J=8Hz, 1H), 7.62(dt, J$_1$=8.8Hz, J$_2$=2Hz, 2H), 7.48(dd, J$_1$=6.4Hz, J$_2$=1.6Hz, 2H), 7.39-7.27(series m, 8H), 7.21(tt, J$_1$=7.6Hz, J$_2$=1.2Hz, 1H), 6.93(dt, J$_1$=9.2Hz, J$_2$=2.4Hz, 2H), 6.69(d, J=15.6, 1H), 5.29(dd, J$_1$=8Hz, J$_2$=6.4Hz, 1H), 4.18(d, J=6.4Hz, 2H). EM(calc.): 402.2; MS(ESI) m/e(M+1H)$^+$: 402.9, (M−1H)$^-$: 401.2.

Cpd. 111

$^1$H NMR(400MHz, DMSO-d$_6$) δ 8.25(d, J=8Hz, 1H), 7.83(d, J=8.8Hz, 2H), 7.48(d, J=6.4Hz, 2H), 7.39-7.27(series m, 4H), 7.01(d, J=8.8Hz, 2H), 6.58(d, J=16.4Hz, 1H), 4.25(m, 1H), 4.03(m, 2H), 3.73(s, 3H), 3.12(m, 2H), 2.06(m, 1H), 1.93(m, 1H). EM(calc.): 432.1; MS(ESI) m/e(M+1H)$^+$: 433.2, (M−1H)$^-$: 430.0.

Cpd. 112

$^1$H NMR(400MHz, DMSO-d$_6$) δ 8.24(d, J=8Hz, 1H), 7.82(d, J=8.8Hz, 2H), 7.48(d, J=8.8Hz, 2H), 7.84-7.29(series m, 4H), 7.01(d, J=8.8Hz, 2H), 6.58(d, J=16.4Hz, 1H), 4.35(m, 1H), 4.03(m, 2H), 3.70(s, 3H), 3.13(m, 2H), 2.06(m, 1H), 1.93(m 1H). EM(calc.): 432.1; MS(ESI) m/e(M+1H)$^+$: 432.2, (M−1H)$^-$: 430.2.

Cpd. 113

$^1$H NMR(400MHz, DMSO-d$_6$) δ 8.50(d, J=8.0Hz, 1H), 7.83(dt, J$_1$=9.2Hz, J$_2$=2.8Hz, 2H), 7.48(dd, J$_1$=6Hz, J$_2$=1.6Hz, 2H), 7.39(d, J=16Hz, 1H), 7.31(m, 9H), 6.97(dt, J$_1$=9.2Hz, J$_2$=2.4Hz, 2H), 6.57(d, J=16Hz, 1H), 4.72(m, 1H), 4.50(s, 1H), 4.16(dd, J$_1$=9.6Hz, J$_2$=5.2Hz), 1H, 4.08(dd, J$_1$=10Hz, J$_2$=4.8Hz, 1H), 3.45(dd, J$_1$=14.4Hz, J$_2$=5.6Hz, 1H), 3.36(dd, J$_1$=14.4Hz, J$_2$=6.8Hz, 1H). EM(calc.): 492.2; MS (ESI) m/e(M+1H)$^+$: 494.3, (M−1H)$^-$: 492.2.

Cpd. 114

$^1$H NMR(400MHz, DMSO) δ 11.07(br s, 1H), 8.38(d, J=7.6Hz, 2H), 7.84(dd, J$_1$=3.6Hz, J$_2$=1.2Hz, 1H), 7.77(dd, J$_1$=4.8Hz, J$_2$=1.2Hz, 1H), 7.72(d, J=8.4Hz, 2H), 7.16(dd, J$_1$=3.6Hz, J$_2$=5.2Hz, 1H), 7.02(d, J=8.4Hz, 2H), 4.20(m, 1H), 4.13(dd, J$_1$=6.4Hz, J$_2$=9.6Hz, 1H), 4.04(dd, J$_1$=5.2Hz, J$_2$=9.2Hz, 2H) 1.77(m 1H), 1.63(m, 1H), 1.21(d, J=6.4Hz, 1H), 0.96(t, J=7.2Hz, 3H). EM(calc.): 334.1; MS(ESI) m/e(M+1H)$^+$: 335.0, (M−1H)$^-$: 333.0.

Cpd. 115

$^1$H NMR(400MHz, DMSO-d$_6$) δ 11.03(s, 1H), 8.37(d, J=8.0Hz, 1H), 7.94(d, J=8.4Hz, 2H), 7.72(m, 6H), 7.48(m, 2H), 7.39(m, 1H), 7.00(d, J=8.4Hz, 2H), 4.24(m, 1H), 4.06(m, 2H), 1.74(m, 2H), 0.95(t, J=7.2Hz, 3H). EM(calc.): 404.2; MS(ESI) m/e(M+1H)$^+$: 405.2, (M−1H)$^-$: 403.2.

Cpd. 116

$^1$H NMR(400MHz, DMSO-d$_6$) δ 11.03(s, 1H), 8.87(s, 1H), 8.50(d, J=8.4Hz, 1H), 8.44(s, 1H), 7.97(m, 4H), 7.70(d, J=8.8Hz, 2H), 7.59(m, 2H), 7.02(d, J=8.8Hz, 2H), 4.29(m, 1H), 4.14(m, 2H), 1.68(m, 2H), 0.98(t, J=7.2Hz, 3H). EM(calc.): 378.2; MS (ESI) m/e(M+1H)$^+$: 378.9, (M−1H)$^-$: 377.0.

Cpd. 117

$^1$H NMR(400MHz, DMSO-d$_6$) δ 10.98(s, 1H), 8.82(s, 1H), 8.27(d, J=8.4Hz, 1H), 7.64(d, J=9.2Hz, 2H), 7.48(dd, J$_1$=6.4Hz, J$_2$=1.6Hz, 2H), 7.38(d, J=15.6Hz, 1H), 7.36-7.27(m, 3H), 7.23-7.19(m, 4H), 7.14(m, 1H), 6.92(d, J=8.8Hz, 2H), 6.61(d, J=15.6Hz, 1H), 4.29(m, 1H), 4.08(dd, J$_1$=9.6Hz, J$_2$=5.6Hz, 1H), 3.98(dd, J$_1$=9.6Hz, J$_2$=4.4Hz, 1H), 3.70(d, J=2.4Hz, 2H), 2.67(dd, J$_1$=6.8Hz, J$_2$=13.6Hz, 1H), 2.58(dd, J$_1$=13.2Hz, J$_2$=7.2Hz, 1H). EM(calc.): 460.2; MS(ESI) m/e(M−1H)$^-$: 460.8.

Cpd. 118

$^1$H NMR(400MHz, DMSO-d$_6$) δ 11.02(s, 1H), 8.31(d, J=8.4Hz, 1H), 7.83(d, J=7.2Hz, 2H), 7.68(d, J=8.8Hz, 2H), 7.52-7.42(m, 3H), 6.99(d, J=9.2Hz, 2H), 4.22(m, 1H), 4.11(dd, J$_1$=6.4Hz, J$_2$=10.0Hz, 1H), 4.01(dd, J$_1$=6.0Hz, J$_2$=9.6Hz, 1H), 1.73(m 1H0, 1.62(m, 1H), 0.93(t, J=7.6Hz, 3H). EM(calc.): 328.1; MS(ESI) m/e (M+1H)$^+$: 329.1.(M−1H)$^-$: 327.0.

Cpd. 119

$^1$H NMR(400MHz, DMSO-d$_6$) δ 11.03(s, 1H), 8.08(d, J=7.2Hz, 1H), 7.69(d, J=8.8Hz, 2H), 7.24(m, 5H), 6.96(d, J=9.2Hz, 2H), 3.94(m 3H), 3.43(s, 2H), 1.64(m, 1H), 1.47(m, 1H), 0.86(t, 7.2Hz, 3H). EM(calc.): 342.2; MS(ESI) m/e(M+1H)$^+$: 343.0, (M−1H)$^-$: 341.1.

Cpd. 120

$^1$H NMR(400MHz, DMSO-d$_6$) δ 11.03(s, 1H), 7.81(d, J=7.6Hz, 1H), 7.69(d, J=8.4Hz, 2H), 7.23-7.10(m, 5H), 6.94(d, J=9.2Hz, 2H), 3.94(m, 2H), 3.84(m, 1H),

TABLE 1-continued 2.81(t, J=7.2Hz, 2H), 2.40(t, J=7.6Hz, 2H), 1.61(ddd, $J_1$=4.4Hz, $J_2$=7.6Hz, $J_3$=18.4Hz, 1H), 1.41(m, 1H), 0.81(t, J=6.8Hz, 3H). EM(calc.): 356.2; MS(ESI) m/e(M+1H)$^+$: 357.1, (M−1H)$^-$: 355.1.
Cpd. 121

EM(calc.): 356.38; MS(ESI) m/e(M+1): 357.0, (M−1): 355.1.
Cpd. 122

$^1$H NMR(400MHz, DMSO-d$_6$) δ 10.96(s, 1H), 8.65(d, J=8.8Hz, 1H), 8.33(s, 1H), 8.00(d, J=7.2Hz, 2H), 7.62(d, J=8.4Hz, 2H), 7.39(pseudo t, J=7.2Hz, 2H), 7.30(pseudo t, J=7.6Hz, 1H), 6.93(d, J=9.2Hz, 2H), 4.20(m, 1H), 4.23(dd partially buried under peak at 4.20,, $J_1$=9.2Hz, $J_2$=16.8Hz, 1H), 4.05(dd, $J_1$=10.0Hz, $J_2$=4.8Hz, 1H), 1.69(m 1H), 1.62(m, 1H), 0.88(t, J=7.2Hz, 3H). EM(calc.): 411.1; MS(ESI) m/e(M−1H)$^-$: 410.1.
Cpd. 123

$^1$H NMR(400MHz, DMSO-d$_6$) δ 11.03(s, 1H), 8.03(d, J=7.6Hz, 1H), 7.69(d, J=8.8Hz, 2H), 7.48(d, J=9.2Hz, 2H), 7.36(d, J=15.6Hz, 1H), 6.99(d, J=9.2Hz, 2H), 6.95(d, J=8.8Hz, 2H), 6.52(d, J=15.6Hz, 1H), 4.09(m, 1H), 4.04(dd, $J_1$=5.2Hz, $J_2$=9.6Hz, 1H), 3.95(dd, $J_1$=5.2Hz, $J_2$=9.6Hz, 1H), 3.77(s, 3H), 1.71(m, 1H), 1.52(m, 1H), 0.91(t, J=6.8Hz, 3H). EM(calc.): 384.2; MS(ESI) m/e(M+1H)$^+$: 385.0, (M−1H)$^-$: 383.2.
Cpd. 124

$^1$H NMR(400MHz, DMSO-d$_6$ δ 11.07(s, 1H), 10.62(br s, 1H), 8.43(d, J=8.0Hz, 1H), 8.28(d, J=1.6Hz, 1H), 7.94(dd, $J_1$=8.4Hz, $J_2$=2.0Hz, 1H), 7.23(d, J=8.4Hz, 2H), 7.32(s, 1H), 7.03(d, J=8.8Hz, 2H), 4.60(s, 2H), 4.28(m, 1H), 4.17(dd, $J_1$=10.0Hz, $J_2$=6.8Hz, 1H), 4.08(dd, $J_1$=10.4Hz, $J_2$=6.0Hz, 1H), 2.84(s, 6H), 1.80(m, 1H), 1.65(m, 1H), 0.98(t, J=7.6Hz, 3H). EM(calc.): 425.2; MS(ESI) m/e(M+1H)$^+$: 426.2, (M−1H)$^-$: 424.1.
Cpd. 125

$^1$H NMR(400MHz, DMSO-d$_6$) δ 10.96(s, 1H), 8.80(s, 1H), 8.27(t, J=5.2Hz, 1H), 7.62(J=8.8Hz, 2H), 7.46(d, J=6.8Hz, 2H), 7.36(d, J=12.8Hz, 1H), 7.33-7.28(m, 3H), 6.95(d, J=8.4Hz, 2H0, 6.60(d, J=12.8Hz, 1H), 4.53(ddd, J=5.6Hz, 1H), 3.40(m, 1H), 3.29(m, 1H, buried under water peak), 1.19(d, J=6.4Hz, 3H). EM(calc.): 340.1.
Cpd. 126

$^1$H NMR(400MHz, DMSO-d$_6$) δ 11.02(s, 1H), 8.87(s, 1H), 8.34(t, J=5.6Hz, 1H), 7.68(d, J=8.4Hz, 2H), 7.53(d, J=8.8Hz, 2H), 7.43(d, J=13.2Hz, 1H), 7.40-7.35(m, 3H), 7.02(d, J=8.8Hz, 2H), 6.67(d, J=16Hz, 1H), 4.60(ddd, $J_1$=6.0Hz, $J_2$=11.6Hz, $J_3$=17.6Hz, 1H), 3.47(m, 1H), 3.36(m 1H, buried under water peak), 1.26(d, J=6.0Hz, 3H). EM(calc.): 340.1; MS(ESI) m/e(M+1H)$^+$: 341.0, (M−1H)$^-$: 339.2.
Cpd. 127

EM(calc.): 397.1; MS(ESI) m/e(M−1H)$^-$: 396.1.
Cpd. 128

EM(calc.): 397.1; MS(ESI) m/e(M+1H)$^+$: 398.2, (M−1H)$^-$: 396.2.
Cpd. 129

$^1$H NMR(400MHz, DMSO-d$_6$) δ 10.96(s, 1H), 8.69(t, J=5.6Hz, 1H), 7.84(d, J=8.4Hz, 2H), 7.67(d, J=8.4Hz, 1H), 7.63(m, 4H), 7.40(t, J=7.6Hz, 2H), 7.32(m, 1H), 6.98(d, J=12.0Hz, 2H), 4.62(ddd, $J_1$=6.0Hz, $J_2$=12.0Hz, $J_3$=18.0Hz, 1H), 3.52(ddd, $J_1$=6.4Hz, $J_2$=13.6Hz, $J_3$=19.6Hz, 1H), 3.31(m, 1H, buried under water peak), 1.23(d, J=6.0Hz, 3H). EM(calc.): 390.2; MS(ESI) m/e(M+1H)$^+$: 391.3, (M−1H)$^-$: 389.0.
Cpd. 130

$^1$H NMR(400MHz, DMSO-d$_6$) δ 11.03(s, 1H), 8.24(t, J=5.2Hz, 1H), 7.68(d, J=8.8Hz, 2H), 7.48(d, J=8.8Hz, 2H), 7.37(d, J=15.6Hz, 1H), 7.02(d, J=8.8Hz, 2H), 6.95(d, J=8.8Hz, 2H), 6.51(d, J=15.6Hz, 1H0), 4.58(pseudo q, J=5.6Hz, 1H), 3.77(s, 3H), 3.46(ddd, $J_1$=4.8Hz, $J_2$=13.2Hz, $J_3$=19.2Hz, 1H), 3.32(ddd, $J_1$=5.2Hz, $J_2$=10.8Hz, $J_3$=13.2Hz, 1H), 1.25(d, J=6.0Hz, 3H). EM(calc.): 370.2; MS(ESI) m/e (M+1H)$^+$: 371.0, (M−1H)$^-$: 369.1.
Cpd. 131

$^1$HNMR(DMSO-d$_6$): 3.67(q, 2H), 4.18(t, 2H), 7.01(d, 2H), 7.7(d, 2H), 7.98(d, 2H), 8.12(d, 2H), 8.17(d, 2H), 8.55(s, 1H), 8.79(m, 3H), 11.05(s, 1H). LC\MS:(M+1)$^{+1}$ 461.2, (M−1)$^{-1}$ 459.0.
Cpd. 132

$^1$H NMR(400MHz, DMSO-d$_6$) δ: 11.08(s, 1H), 8.94(m, 2H), 7.75(m, 3H), 7.47(d, 1H, J=8.1Hz), 7.16(d, 1H, J=8.1Hz), 7.04(d, 2H, J=9.6Hz), 4.22(t, 2H, J=5.5Hz), 3.71(t, 2H, J=5.5Hz), 3.36(s, 3H). EM(calc.): 388.08; MS(ESI) m/e(M+1H)$^+$: 388.9, (M−1H)$^-$: 387.1.

TABLE 1-continued

Cpd. 133

¹HNMR(DMSO-d₆): 2.85(s, 3H), 3.4(s, 8H), 3.65(q, 2H), 4.17(t, 2H), 7.00(d, 2H), 7.54(s, 1H), 7.7(d, 2H), 7.9(dd, 4H), 8.74(t, 1H), 8.9(s, 1H), 10.2(s, 1H), 11.05(s, 1H). LC\MS:(M+1)⁺¹ 482.0, (M−1)⁻¹ 480.2.

Cpd. 134

¹HNMR(DMSO-d₆): 3.66(q, 2H), 4.18(t, 2H), 7.01(d, 2H), 7.69(m, 4H), 7.91(d, 2H), 8.02(d, 3H), 8.33(dd, 2H), 8.75(t, 1H), 9.16(s, 1H), 10.99(s, 1H), 11.05(s, 1H). LC\MS:(M+1)⁺¹ 476.1, (M−1)⁻¹ 474.2.

Cpd. 135

¹HNMR(DMSO-d₆): 2.85(s, 3H), 3.01(m, 4H), 3.51(d, 2H), 3.60(q, 2H), 4.00(d, 2H), 4.13(t, 2H), 6.98(dd, 4H), 7.74(dd, 4H), 8.48(t, 1H), 9.97(s, 1H), 11.05(s, 1H). LC\MS:(M+1)⁺¹ 399.3, (M−1)⁻¹ 397.2.

Cpd. 136

¹HNMR(DMSO-d₆): 1.4(m, 2H), 1.8(m, 2H), 2.95(m, 2H), 3.6(m, 5H), 4.12(t, 2H), 4.69(s, 1H), 6.91(d, 2H), 6.99(d, 2H), 7.7(dd, 4H), 8.36(t, 1H), 8.87(s, 1H), 11.03(s, 1H). LC\MS:(M+1)⁺¹ 400.2, (M−1)⁻¹ 398.3.

Cpd. 138

¹H NMR(400MHz, DMSO-d₆) δ: 9.02(t, 2H, J=5.3Hz), 7.77-7.72(m, 3H), 7.27(m, 1H), 7.11(m, 1H), 7.03(d, 2H, J=8.8Hz), 4.22(t, 2H, J=5.3Hz), 3.70(t, 2H, J=5.3Hz), 2.51(s, 3H). EM(calc.): 372; MS(ESI) m/e(M+1H)⁺: 373.0, (M−1H)⁻: 371.0.

Cpd. 139

¹H NMR(400MHz, DMSO-d₆) δ: 11.04(s, 1H), 10.04(s, 1H), 9.02(t, 1H, J=5.7Hz), 7.74(d, 1H, J=2.7Hz), 7.70(d, 2H, J=8.5Hz), 7.32(m, 1H), 7.25(m, 1H), 7.00(d, 2H, J=8.5Hz), 4.72(s, 2H), 4.19(t, 2H, J=5.7Hz), 3.67(m, 2H), 3.59(m, 2H), 3.48(m, 2H), 3.24(s, 3H). EM(calc.): 446.15; MS(ESI) m/e(M+1H)⁺: 447.4, (M−1H)⁻: 445.3.

Cpd. 140

¹H NMR(400MHz, DMSO-d₆) δ: 11.04(br s, 1H), 9.25(t, 1H, J=5.9Hz), 8.07(d, 1H, J=8.6Hz), 7.96(d, 1H, J=8.6Hz), 7.70(m, 3H), 7.39(t, 1H, J=7.6Hz), 7.01(d, 2H, J=9.1Hz), 6.88(br s, 1H), 4.21(t, 2H, J=5.9Hz), 3.70(q, 2H, J=5.9Hz). EM(calc.): 367; MS(ESI) m/e(M+1H)⁺: 368.0, (M−1H)⁻: 366.2.

Cpd. 141

¹H NMR(400MHz, DMSO-d₆) δ: 11.04(br s, 1H), 9.04(t, 1H, J=5.9Hz), 7.80(d, 1H, J=2.6Hz), 7.70(d, 1H, J=8.7Hz), 7.40(m, 2H), 7.28(t, 1H, J=8.1Hz), 7.05-6.92(m, 5H), 5.35(s, 2H), 4.18(t, 2H, J=5.9Hz), 3.66(q, 2H, J=5.9Hz). EM(calc.): 464; MS(ESI) m/e(M+1H)⁺: 465.3, (M−1H)⁻: 463.1.

Cpd. 143

¹HNMR(DMSO-d₆): 2.55(t, 3H), 2.80(s, 3H), 3.07(d, 3H), 3.4(d, 2H), 3.65(q, 2H), 4.02(s, 2H), 4.17(t, 2H), 6.99(d, 2H), 7.69(d, 2H), 7.91(d, 2H), 8.01(d, 2H), 8.23(s, 1H), 8.75(t, 1H), 9.6(s, 1H), 11.05(s, 1H). LC\MS:(M+1)⁺¹ 496.3, (M−1)⁻¹ 494.4

Cpd. 144

MS(ESI) m/e:(M+1H)⁺: 302.0, (M−1H)⁻: 300.2.

Cpd. 145

MS(ESI) m/e:(M+1H)⁺: 318.1, (M−1H)⁻: 316.1.

Cpd. 146

MS(ESI) m/e:(M+1H)⁺: 318.1, (M−1H)⁻: 316.2.

Cpd. 147

¹H NMR(400MHz, DMSO-d₆) δ 11.04(s, 1H), 8.28(m, 2H), 8.15(m, 1H), 7.94(m, 2H), 7.66(m, 2H), 7.41(m, 3H), 6.89(m, 2H), 4.10(m, 2H), 3.63(m, 2H). MS(ESI) m/e:(M+1H)⁺: 439.2, (M−1H)⁻: 437.2.

Cpd. 148

¹H NMR(400MHz, DMSO-d₆) δ 11.04(s, 1H), 9.10(t, J=8.0Hz, 1H), 8.18(d, J=8.0Hz, 1H), 8.06(d, J=8.0Hz, 1H), 7.85(t, J=8.0Hz, 1H), 7.67(m, 4H), 7.04(d, J=8.0Hz, 2H), 4.45(m, 2H), 4.23(t, J=8.0Hz, 2H), 3.84(m, 2H), 3.76(m, 2H). MS(ESI) m/e: (M+1H)⁺: 426.3, (M−1H)⁻: 424.2.

Cpd. 149

¹H NMR(400MHz, DMSO-d₆) δ 11.06(s, 1H), 10.31(s, 1H), 9.10(t, J=8.0Hz, 1H), 8.40(d, J=8.0Hz, 1H), 8.07(d, J=8.0Hz, 1H), 7.86(t, J=8.0Hz, 1H), 7.69(m, 4H), 7.02(d, J=8.0Hz, 2H), 4.74(m, 2H), 4.23(t, J=8.0Hz, 2H), 3.77(m, 2H), 3.70(m, 2H). MS(ESI) m/e:(M+1H)⁺: 439.3, (M−1H)⁻: 437.3.

Cpd. 150

MS(ESI) m/e:(M+1H)⁺: 379.9, (M−1H)⁻: 379.9.

TABLE 1-continued

Cpd. 151

MS(ESI) m/e:(M+1H)$^+$: 379.9, (M−1H)$^-$: 379.9.
Cpd. 152

$^1$H NMR(400MHz, DMSO-d$_6$) δ: 11.04(br s, 1H), 8.85(d, 1H, J=9.0Hz),
8.20(d, 1H, J=1.2Hz), 8.18(d, 1H, J=1.2Hz), 7.85(m, 1H), 7.70-7.65(m, 4H), 7.01(t, 2H,
J=8.7Hz), 4.32(m, 1H), 4.25(m, 1H), 4.15(s, 3H), 4.13(m, 1H), 1.77(m, 2H), 0.95(t, 3H, J=7.0).
EM(calc.): 409; MS(ESI) m/e(M+1H)$^+$: 410.2, (M−1H)$^-$: 408.2.
Cpd. 153

$^1$H NMR(400MHz, DMSO-d$_6$) δ: 11.05(s, 1H), 10.17(s, 1H), 8.65(m, 1H),
8.14(m, 1H), 7.95(m, 1H), 7.88(d, 1H, J=8.2Hz), 7.73-7.66(m, 3H), 7.62-7.59(m, 2H),
7.05(m, 2H), 4.24(m, 2H), 3.89(s, 3H), 3.73(m, 2H). EM(calc.): 380; MS(ESI) m/e
(M+1H)$^+$: 381.0, (M−1H)$^-$: 379.1.
Cpd. 154

$^1$H NMR(400MHz, DMSO-d$_6$) δ: 11.04(s, 1H), 9.14(t, 1H, J=6.0Hz),
8.18(d, 1H, J=7.7Hz), 8.07(d, 1H, J=8.2Hz), 7.85(t, 1H, J=7.7Hz), 7.72-7.64(m, 4H), 7.08(d,
2H, J=9.1Hz), 4.78(m, 1H), 4.14(s, 3H), 3.66(m, 1H), 3.55(m, 1H), 1.31(d, 3H, J=6.1Hz).
EM(calc.): 395; MS(ESI) m/e(M+1H)$^+$: 396.1, (M−1H)$^-$: 394.2.
Cpd. 155

MS(ESI) m/e:(M+1H)$^+$: 377.9, (M−1H)$^-$: 376.1.
Cpd. 156

MS(ESI) m/e:(M+1H)$^+$: 408.3, (M−1H)$^-$: 406.2.
Cpd. 157

MS(ESI) m/e:(M+1H)$^+$: 373.9, (M−1H)$^-$: 372.1.
Cpd. 158

MS(ESI) m/e:(M+1H)$^+$: 422.3, (M−1H)$^-$: 420.3.
Cpd. 159

$^1$H NMR(400MHz, DMSO-d$_6$) δ: 11.04(s, 1H), 9.10(t, 1H, J=5.9Hz),
8.16(d, 1H, J=8.4Hz), 8.07(d, 1H, J=8.4Hz), 7.85(t, 1H, J=7.9Hz), 7.71-7.65(m, 4H), 7.03(d,
2H, J=8.9Hz), 4.60(t, 2H, J=5.9Hz), 4.23(t, 2H, J=5.1Hz), 3.75(q, 2H, J=5.9Hz),
3.00(m, 2H). EM(calc.): 463; MS(ESI) m/e(M+1H)$^+$: 464.3, (M−1H)$^-$: 462.2.
Cpd. 160

$^1$H NMR(400MHz, DMSO-d$_6$) δ: 11.04(s, 1H), 8.78(d, 1H, J=9.0Hz), 8.15(d, 1H,
J=8.3Hz), 8.09(d, 1H, J=8.5Hz), 7.85(t, 1H, J=6.7Hz), 7.68(m, 4H), 7.00(d, 2H, J=9.0Hz),
4.61(t, 2H, J=5.9Hz), 4.32(m, 1H), 4.24(m, 1H), 4.14(m, 1H), 3.00(m, 2H),
1.76(m, 2H), 0.95(t, 3H, J=7.0Hz). EM(calc.): 491; MS(ESI) m/e(M+1H)$^+$: 492.1, (M−1H)$^-$:
490.1.
Cpd. 161

$^1$H NMR(400MHz, DMSO-d$_6$) δ: 9.13(t, 1H, J=6.1Hz), 8.15(d, 1H, J=8.1Hz),
8.07(d, 1H, J=8.3Hz), 7.86(t, 1H, J=6.7Hz), 7.71-7.67(m, 4H), 7.08(d, 2H, J=8.7Hz),
4.78(m, 1H), 4.61(t, 1H, J=5.5Hz), 3.65(m, 1H), 3.55(m, 1H), 3.00(m, 2H),
1.31(d, 3H, J=6.0Hz). EM(calc.): 477; MS(ESI) m/e(M+1H)$^+$: 477.9, (M−1H)$^-$: 476.1.
Cpd. 162

$^1$HNMR(DMSO-d$_6$): 3.56(s, 2H), 4.09(t, 2H), 6.57(d, 1H), 6.77(d, 1H), 6.95(m,
3H), 7.18(t, 1H), 7.32(d, 2H), 7.69(d, 2H), 8.38(t, 1H), 9.6(s, 1H), 11.05(s, 1H). LC\MS:
(M+1)$^{+1}$ 343.2, (M−1)$^{-1}$ 341.3.
Cpd. 163

$^1$HNMR(DMSO-d$_6$): 3.55(s, 2H), 4.08(t, 2H), 6.4(d, 1H), 6.8(d, 1H), 7.0(d,
2H), 7.35(d, 1H), 7.4(d, 2H), 7.69(d, 2H), 8.25(t, 1H), 9.85(s, 1H), 11.05(s, 1H). LC\MS:
(M+1)$^{+1}$ 343.1, (M−1)$^{-1}$ 341.1.
Cpd. 164

EM(calc.): 420.17; MS(ESI) m/e(M+1H)$^+$: 421.2, (M−1H)$^-$: 419.5.
Cpd. 165

EM(calc.): 420.17; MS(ESI) m/e(M+1H)$^+$: 421.3, (M−1H)$^-$: 419.3.
Cpd. 166

EM(calc.): 420.17; MS(ESI) m/e(M+1H)$^+$: 421.3, (M−1H)$^-$: 419.3.
Cpd. 167

$^1$HNMR(DMSO-d$_6$): δ 8.89(1H, s), 8.58(1H, m), 7.71(2H, m), 7.65(1H, d),
7.56(1H, d), 7.41(1H, d), 7.36(1H, t), 7.25(1H, t), 7.21(1H, s), 7.00(2H, d), 6.74(1H, dd),
4.11(2H, t), 3.58(2H, q).
Cpd. 168

EM(calc.): 420.17; MS(ESI) m/e(M+1H)$^+$: 421.2, (M−1H)$^-$: 419.3.

TABLE 1-continued

Cpd. 169

¹H NMR(400MHz, DMSO-d₆) δ 11.07(s, 1H), 9.14(s, 1H), 9.11(t, J=8.0Hz, 1H), 8.93(s, 1H), 8.63(t, J=4.0Hz, 1H), 8.17(m, 1H), 7.72(m, 4H), 7.00(d, J=8.0Hz, 2H), 4.20(t, J=8.0Hz, 2H), 3.71(m, 2H). MS(ESI) m/e:(M+1H)⁺: 384.1, (M−1H)⁻: 382.0.

Cpd. 170

MS(ESI) m/e:(M+1H)⁺: 451.0, (M−1H)⁻: 449.2.

Cpd. 171

MS(ESI) m/e:(M+1H)⁺: 409.3, (M−1H)⁻: 407.2.

Cpd. 172

¹HNMR(DMSO-d₆): 3.54(q, 2H), 3.84(s, 3H), 4.08(t, 2H), 6.6(d, 1H), 6.98(m, 4H), 7.35(t, 1H), 7.5(d, 1H), 7.65(d, 1H), 7.69(d, 2H), 8.36(t, 1H), 8.9(s, 1H), 11.04(s, 1H). LC\MS:(M+1)⁺¹ 356.9, (M−1)⁻¹ 355.2.

Cpd. 173

¹HNMR(DMSO-d₆): 3.56(q, 2H), 3.77(s, 3H), 4.09(t, 2H), 6.66(d, 1H), 6.93(m, 2H), 6.99(d, 2H), 7.1(d, 2H), 7.29(t, 1H), 7.39(d, 1H), 7.70(d, 2H), 7.87(d, 1H), 8.36(t, 1H), 8.9(s, 1H), 11.05(s, 1H). LC\MS:(M+1)⁺¹ 357.1, (M−1)⁻¹ 355.1.

Cpd. 174

¹H NMR(400MHz, DMSO-d₆) δ 11.05(s, 1H), 9.21(t, J=8.0Hz, 1H), 9.07(s, 1H), 8.92(s, 1H), 8.67(s, 1H), 7.70(m, 4H), 7.01(d, J=8.0Hz, 2H), 6.92(m, 1H), 4.21(t, J=8.0Hz, 2H), 3.71(m, 2H). MS(ESI) m/e:(M+1H)⁺: 421.2, (M−1H)⁻: 419.4.

Cpd. 175

¹HNMR(DMSO-d₆): δ 8.91(1H, s), 8.44(1H, t), 7.73(2H, d), 7.72(1H, s), 7.57(1H, d), 7.44(1H, d), 7.02(2H, d), 6.50(1H, d), 4.11(2H, t), 3.58(2H, q). LC/MS, M+1: 413.1.

Cpd. 176

¹HNMR(DMSO-d₆): 3.54(q, 2H), 4.07(t, 2H), 6.36(d, 1H), 6.68(s, 1H), 6.98(d, 2H), 7.32(d, 1H), 7.69(m, 3H), 7.98(s, 1H), 8.27(t, 1H), 8.9(s, 1H), 11.04(s, 1H). LC\MS: (M+1)⁺¹ 316.9, (M−1)⁻¹ 315.3.

Cpd. 177

¹HNMR(DMSO-d₆): 3.55(q, 2H), 4.08(t, 2H), 6.47(d, 1H), 6.98(d, 2H), 7.31(d, 1H), 7.42(d, 1H), 7.58(m, 1H), 7.69(d, 2H), 7.78(s, 1H), 8.30(t, 1H), 8.9(s, 1H), 11.04(s, 1H). LC\MS:(M+1)⁺¹ 333.0, (M−1)⁻¹ 331.0.

Cpd. 178

¹HNMR(DMSO-d₆): δ 8.91(1H, s), 8.40(1H, t), 7.73(2H, d), 7.61(2H, m), 7.38(1H, d), 7.11(1H, dd), 7.01(2H, d), 6.43(1H, d), 4.11(2H, t), 3.57(2H, q). LC/MS, M+1: 333.0.

Cpd. 179

¹HNMR(DMSO-d₆): 2.31(s, 3H), 3.55(q, 2H), 4.09(t, 2H), 6.6(d, 1H), 6.99(d, 2H), 7.2-7.4(m, 6H), 7.70(d, 2H), 8.33(t, 1H), 8.9(s, 1H), 11.04(s, 1H). LC\MS:(M+1)⁺¹ 341.1, (M−1)⁻¹ 339.1.

Cpd. 180

¹HNMR(DMSO-d₆): 2.31(s, 3H), 3.55(q, 2H), 4.09(t, 2H), 6.6(d, 1H), 6.99(d, 2H), 7.2(d, 2H), 7.38(d, 1H), 7.42(d, 2H), 7.69(d, 2H), 8.33(t, 1H), 8.9(s, 1H), 11.04(s, 1H). LC\MS:(M+1)⁺¹ 341.2, (M−1)⁻¹ 339.2.

Cpd. 181

¹HNMR(DMSO-d₆): δ 8.87(1H, s), 8.52(1H, t), 7.70(2H, d), 7.64(1H, d), 7.52(1H, d), 7.34(1H, m), 7.24(1H, t), 7.22(1H, s), 6.99(2H, d), 6.67(1H, m), 4.09(2H, t), 3.52(2H, q), 2.48(3H, m). LC/MS, M+1: 381.0.

Cpd. 182

¹HNMR(DMSO-d₆): δ 8.88(1H, s), 8.33(1H, t), 7.68(2H, d), 7.54(1H, m), 7.41(1H, d), 7.28(1H, s), 7.24(1H, m), 7.19(1H, m), 6.95(2H, d), 6.07(1H, m), 4.11(2H, t), 3.52(2H, q), 2.15(3H, m). LC/MS, M+1: 381.1.

Cpd. 183

¹HNMR(DMSO-d₆): 2.94(s, 6H), 3.54(q, 2H), 4.07(t, 2H), 6.38(d, 1H), 6.69(d, 2H), 6.98(d, 2H), 7.29(d, 1H), 7.35(d, 2H), 7.69(d, 2H), 8.15(t, 1H), 8.87(s, 1H), 11.04(s, 1H). LC\MS:(M+1)⁺¹ 370.1, (M−1)⁻¹ 368.3.

Cpd. 184

¹HNMR(DMSO-d₆): 3.57(q, 2H), 4.10(t, 2H), 6.65(d, 1H), 7.0(d, 2H), 7.14(m, 2H), 7.42(m, 1H), 7.6(d, 1H), 7.72(m, 3H), 7.87(d, 1H), 8.149(t, 1H), 8.87(s, 1H), 11.04(s, 1H), 11.52(s, 1H). LC\MS:(M+1)⁺¹ 366.2, (M−1)⁻¹ 364.4.

TABLE 1-continued

Cpd. 185

$^1$HNMR(DMSO-d$_6$): 2.36(s, 3H), 3.56(q, 2H), 4.10(t, 2H), 6.56(d, 1H), 7.00(d, 2H), 7.23(m, 3H), 7.5(d, 1H), 7.65(d, 1H), 7.7(d, 2H), 8.4(t, 1H), 8.87(s, 1H), 11.04(s, 1H). LC\MS:(M+1)$^{+1}$ 341.2, (M−1)$^{−1}$ 339.3.

Cpd. 186

$^1$HNMR(DMSO-d$_6$): 3.55(q, 2H), 3.93(s, 3H), 4.08(t, 2H), 6.66(d, 1H), 6.79(t, 1H), 6.86(d, 1H), 6.98(d, 2H), 7.15(m, 1H), 7.4(d, 1H), 7.65(d, 1H), 7.7(d, 2H), 8.31(t, 1H), 10.0(s, 1H), 11.04(s, 1H). LC\MS:(M+1)$^{+1}$ 343.1, (M−1)$^{−1}$ 340.9.

Cpd. 187

$^1$HNMR(DMSO-d$_6$): 3.57(q, 2H), 3.93(s, 3H), 4.09(t, 2H), 6.75(d, 1H), 6.98(m, 3H), 7.18(m, 3H), 7.38(d, 1H), 7.7(d, 2H), 8.5(t, 1H), 8.87(s, 1H), 11.04(s, 1H). LC\MS:(M+1)$^{+1}$ 396.7, (M−1)$^{−1}$ 395.0.

Cpd. 188

$^1$HNMR(DMSO-d$_6$): 0.922(t, 3H), 1.5-1.8(m, 2H), 3.93(s, 3H), 3.95-4.07(m, 3H), 6.8(d, 1H), 6.98(m, 3H), 7.19(m, 3H), 7.36(d, 1H), 7.69(d, 2H), 8.3(d, 1H), 11.03(s, 1H). LC\MS:(M+1)$^{+1}$ 425.2, (M−1)$^{−1}$ 423.2.

Cpd. 189

$^1$H NMR(DMSO-d$_6$): 0.95(3H, t, 7Hz); 1.53(1H, m); 1.72(1H, m); 2.52(3H, s); 3.79(3H, s); 3.94(1H, m); 4.06(2H, m); 6.66(1H, s); 6.93(1H, dd); 7.02(2H, d); 7.15(2H, m); 7.42(1H, d); 7.7(2H, d); 8.27(2H, d, 7Hz); 8.87(1H, d, 2Hz). MS(M+1): 439.

Cpd. 190

$^1$HNMR(DMSO-d$_6$): 3.54(q, 2H), 4.08(t, 2H), 6.44(d, 1H), 6.56(s, 1H), 6.75(s, 1H), 6.98(d, 2H), 7.23(d, 1H), 7.70(d, 2H), 7.75(s, 1H), 8.41(t, 1H), 8.9(s, 1H), 11.04(s, 1H). LC\MS:(M+1)$^{+1}$ 317.0, (M−1)$^{−1}$ 315.2.

Cpd. 191

$^1$HNMR(DMSO-d$_6$): 3.5-4.05(m, 14H), 4.18(t, 2H), 6.99(d, 2H), 7.69(d, 2H), 7.93(d, 2H), 8.02(d, 2H), 8.2(s, 1H), 8.76(t, 1H), 8.97(s, 1H), 11.05(s, 1H). LC\MS:(M+1)$^{+1}$ 497.4, (M−1)$^{−1}$ 495.4.

TABLE 2

Cpd. 1

EM(calc.): 370.2; MS(ESI) m/e(M+1)$^+$: 371.1, (M−1)$^−$: 369.2.

Cpd. 2

$^1$H NMR(400MHz, DMSO-d$_6$) δ 11.03(s, 1H), 8.88(s, 1H), 7.67 (d, J=9.2Hz, 2H), 7.51(m, 3H), 7.36(m, 8H), 6.92(d, J=9.2Hz, 2H), 6.27(d, J=15.2Hz, 1H), 4.16(m, 4H). EM(calc.): 402.2; MS(ESI) m/e(M+1H)$^+$: 403.1, (M−1H)$^−$: 401.1.

Cpd. 3

EM(calc.): 340.1; MS(ESI) m/e(M+1H)$^+$: 341.0, (M−1H)$^−$: 339.4.

Cpd. 4

EM(calc.): 398.13; MS(ESI) m/e(M+1H)$^+$: 399.0, (M−1H)$^−$: 397.1.

Cpd. 5

EM(calc.): 368.17; MS(ESI) m/e(M+1H)$^+$: 368.8, (M−1H)$^−$: 367.2.

Cpd. 6

EM(calc.): 354.1; MS(ESI) m/e(M+1H)$^+$: 354.8, (M−1H)$^−$: 353.2.

TABLE 3

Cpd. 1

$^1$H NMR(400MHz, DMSO-d$_6$) δ 11.11(s, 1H), 9.07(t, J=5.2Hz, 1H), 8.94(s, 1H), 8.16(s, 1H), 8.07(dd, J$_1$=2.4Hz, J$_2$=8.4Hz, 1H), 7.99(dd, J$_1$=2.4Hz, J$_2$=6.8Hz, 1H), 7.77(d, J=9.2Hz, 2H), 7.50(m, 2H), 7.08(d, J=8.8Hz, 2H), 4.25(pseudo t, J=5.6Hz, 2H), 3.73(pseudo q, J=5.2Hz, 2H). EM(calc.): 358.1; MS(ESI) m/e(M+1H)$^+$: 357.0, (M−1H)$^−$: 355.1.

Cpd. 2

$^1$H NMR(400MHz, DMSO-d$_6$) δ 11.05(s, 1H), 8.92(t, J=5.6Hz, 1H), 8.88(s, 1H), 7.76(d, J=8.0Hz, 1H), 7.70(d, J=9.2Hz, 2H), 7.64(d, J=

TABLE 3-continued 8.0Hz, 1H), 7.55(s, 1H), 7.46(t, J=6.8Hz, 1H), 7.32(t, J=8.0Hz, 1H), 7.01 (d, J=8.2Hz, 2H), 4.18(t, J=5.6Hz, 2H), 3.67(m, 2H). EM(calc.): 340.1; MS(ESI) m/e: (M+1H)$^+$: 341.0, (M−1H)$^−$: 339.1.

Cpd. 3

$^1$H NMR(400MHz, DMSO-d$_6$) δ: 11.57(s, 1H), 11.04(s, 1H), 8.71(t, J=5.6Hz, 1H), 7.70(d, J=8.8Hz, 2H), 7.59(d, J=8.4Hz, 1H), 7.40(d, J=8.4Hz, 1H), 7.16(t, J=8.4Hz, 1H), 7.12(m, 1H), 7.00(m, 3H), 4.18(t, J=5.6Hz, 2H), 3.68(m, 2H). EM(calc.): 339.1; MS(ESI) m/e(M+1H)$^+$: 340.1, (M−1H)$^−$: 338.3.

Cpd. 4

EM(calc.): 353.1; MS(ESI) m/e(M+1)$^+$: 354.1, (M−1)$^−$: 352.2.

Cpd. 5

$^1$H NMR(400MHz, DMSO-d$_6$) δ 8.84(t, J=5.6Hz, 1H), 8.05(s, 1H), 7.99(dd, J$_1$=6.0Hz, J$_2$=2.0Hz, 1H), 7.91(dd, J$_1$=6.4Hz, J$_2$=2.0Hz, 1H), 7.65(d, J=8.8Hz, 2H), 7.42(m, 2H), 6.88(d, J=8.4Hz, 2H), 4.06(t, J=6.0Hz, 2H), 3.43(pseudo q, J=5.6Hz, 2H), 2.00(pseudo p, J=6.0Hz, 2H). EM(calc.): 370.1; MS(ESI) m/e(M+1H)$^+$: 371.1, (M−1H)$^−$: 369.0.

Cpd. 6

$^1$H NMR(400MHz, DMSO-d$_6$) δ 10.96(s, 1H), 8.74(t, J=6.0Hz, 1H), 7.67(d, J=7.6Hz, 1H), 7.62(d, J=8.4Hz, 2H), 7.44(s, 1H), 7.55(dd, J$_1$=8.4Hz, J$_2$=0.8Hz, 1H), 7.43(d, J=0.8Hz, 1H), 7.37(td, J$_1$=7.2Hz, J$_2$=1.2Hz, 1H), 7.241(td, J$_1$=8.0Hz, J$_2$=0.8Hz, 1H), 6.89(d, J=8.8Hz, 2H), 4.01(t, J=6.4Hz, 2H), 3.37(pseudo q, J=6.0Hz, 2H), 1.94(pseudo p, J=6.0Hz, 2H). EM(calc.): 354.1; MS(ESI) m/e(M+1H)$^+$: 355.2, (M−1H)$^−$: 353.1.

Cpd. 7

$^1$H NMR(400MHz, DMSO-d$_6$) δ 11.07(s, 1H), 8.91(s, 1H), 8.65(br d, J=7.2Hz, 1H), 8.20(s, 1H), 8.03(m, 1H), 7.95(m, 1H), 7.72(d, J=8.4Hz, 2H), 7.46(m, 2H), 7.03(d, J=8.8Hz, 2H), 4.20(m, 3H), 2.08(m, 1H), 1.02(d, J=6.8Hz, 6H). EM(calc.): 398.1; MS(ESI) m/e(M+1H)$^+$: 399.0, (M−1H)$^−$: 397.1.

TABLE 3-continued

Cpd. 8

$^1$H NMR(400MHz, DMSO-d$_6$) δ 11.07(s, 1H), 8.91(s, 1H), 8.68(d, J=8.0Hz, 1H), 8.17(s, 1H), 8.03(dd, J$_1$=2.0Hz, J$_2$=6.4Hz, 1H), 7.96(dd, J$_1$=4.0Hz, J$_2$=6.8Hz, 1H), 7.73(d, J=8.8Hz, 2H), 7.46(m, 4H), 7.04(d, J=9.2Hz, 2H), 4.24(m, 1H), 4.18(dd, J$_1$=6.8Hz, J$_2$=10.0Hz, 1H), 4.09(dd, J$_1$=5.2Hz, J$_2$=9.6Hz,), 1.81(m, 1H), 1.67(m, 1H), 0.99(t, J=7.6Hz, 3H). EM(calc.): 384.1; MS(ESI) m/e(M+1H)$^+$: 385.0, (M−1H)$^−$: 383.1.

Cpd. 9

$^1$H NMR(400MHz, DMSO-d$_6$) δ 11.11(s, 1H), 8.95(br s, 1H), 8.80(d, J=8.0Hz, 1H), 8.19(s, 1H), 8.06(dd, J$_1$=5.6Hz, J$_2$=1.6Hz, 1H), 7.98(dd, J$_1$=6.8Hz, J$_2$=1.6Hz, 1H), 7.76(d, J=8.4Hz, 2H), 7.49(m, 2H), 7.08(d, J=8.8Hz, 2H), 4.42(p, J=6.4Hz, 1H), 4.20(dd, J$_1$=9.6Hz, J$_2$=6.4Hz, 1H), 4.07(dd, J$_1$=9.6Hz, J$_2$=5.6Hz, 1H), 1.36(d, J=6.8Hz, 3H). EM(calc.): 370.1; MS(ESI) m/e(M+1H)$^+$: 371.0, (M−1H)$^−$: 368.9.

Cpd. 10

$^1$H NMR(400MHz, DMSO-d$_6$) δ 10.95(s, 1H0, 8.65(d, J=7.6Hz, 1H), 8.04(s, 1H), 7.91(d, J=7.2Hz, 1H), 7.83(d, J=6.4Hz, 1H), 7.61(d, J=8.8Hz, 2H), 7.34(m, 2H), 6.93(d, J=8.8Hz, 2H), 4.27(p. J=6.4Hz, 1H), 4.05(dd, J$_1$=6.8Hz, J$_2$=10.0Hz, 1H), 3.92(dd, J$_1$=10.0Hz, J$_2$=6.0Hz, 1H), 1.21(d, J=5.2Hz, 3H). EM(calc.): 370.1; MS(ESI) m/e(M+1H)$^+$: 370.9, (M−1H)$^−$: 369.0.

Cpd. 11

$^1$H NMR(400MHz, DMSO-d$_6$) δ 10.96(s, 1H), 8.54(d, J=8.4Hz, 1H), 7.68(d, J=7.6Hz, 1H), 7.61(d, J=8.4Hz, 2H), 7.58(d, J=8.4Hz, 1H), 7.48(d, J=0.8Hz, 1H), 7.38(td, J$_1$=8.0Hz, J$_2$=0.8Hz, 1H), 7.25(td, J$_1$=7.2Hz, J$_2$=0.8Hz, 1H), 6.92(d, J=8.8Hz, 2H), 4.19(m, 1H), 4.07(dd, J$_1$=10.4Hz, J$_2$=6.4Hz, 1H), 3.99(dd, J$_1$=10.0Hz, J$_2$=5.6Hz, 1H), 1.68(m, 1H), 1.55(m, 1H), 0.86(t, J=7.2Hz, 3H). EM(calc.): 368.1; MS(ESI) m/e(M−1H)$^−$: 367.1.

Cpd. 12

$^1$H NMR(400MHz, DMSO-d$_6$) δ 11.06(s, 1H), 9.03(t, J=6.0Hz, 1H), 8.11(s, 1H), 8.03(d, J=7.2Hz, 1H), 7.94(d, J=6.4Hz, 1H), 7.72(d, J=8.8Hz, 2H), 7.46(m, 2H), 7.07(d, J=9.2Hz, 2H), 4.72(pseudo q, J=5.6Hz, 1H), 3.62(m, 1H), 3.42(m, 1H), 1.34(d, J=6.4Hz, 3H). EM(calc.): 370.1; MS(ESI) m/e(M+1H)$^+$: 371.0, (M−1H)$^−$: 369.1.

Cpd. 13

$^1$H NMR(400MHz, DMSO-d$_6$) δ 11.06(s, 1H), 9.03, (t, J=5.6Hz, 1H), 8.11(s, 1H), 8.03(d, J=6.8Hz, 1H), 7.94(d, J=7.2Hz, 1H), 7.72(d, J=8.4Hz, 2H), 7.46(pseudo p, J=5.6Hz, 2H), 7.07(d, J=8.4Hz, 2H), 4.74 (pseudo q, J=5.6Hz, 1H), 3.63(m, 1H), 3.42(m, 1H), 1.34(d, J 6.0Hz, 3H). EM(calc.): 370.1; MS(ESI) m/e(M+1H)$^+$: 371.0, (M−1H)$^−$: 369.1.

Cpd. 14

$^1$H NMR(400MHz, DMSO-d$_6$) δ 11.02(s, 1H), 8.92(t, J=6.0Hz, 1H), 7.75(d, J=7.6Hz, 1H), 7.68(d, J=8.8Hz, 2H), 7.54(d, J=0.8Hz, 1H), 7.44(td, J$_1$=7.2Hz, J$_2$=0.8Hz, 1H), 7.31(td, J=7.6Hz, J$_2$=0.8Hz, 1H), 7.03(d, J=9.2Hz, 2H), 4.69(pseudo q, J=6.4Hz, 1H), 3.59(ddd, J$_1$=6.4Hz, J$_2$=13.6Hz, J$_3$=19.6Hz, 1H), 3.39(ddd, J$_1$=6.0Hz, J$_2$=12.4Hz, J$_3$=19.6Hz, 1H), 1.29(d, J=6.4Hz, 3H). EM(calc.): 354.1; MS(ESI) m/e(M+1H)$^+$: 354.7, (M−1H)$^−$: 353.1.

Cpd. 15

EM(calc.): 386.09; MS(ESI) m/e(M−1H)$^−$: 384.7.

Cpd. 16

EM(calc.): 370.10; MS(ESI) m/e(M−1H)$^−$: 369.0.

Cpd. 17

EM(calc.): 390.0; MS(ESI) m/e(M+1H)$^+$: 391.2.

Cpd. 18

EM(calc.): 354.12; MS(ESI) m/e(M−1H)$^−$: 353.2.

Cpd. 19

EM(calc.): 354.12; MS(ESI) m/e(M−1H)$^−$: 353.1.

Cpd. 20

EM(calc.): 424.07; MS(ESI) m/e(M−1H)$^−$: 423.9.

Cpd. 21

EM(calc.): 374.0; MS(ESI) m/e(M+1)$^+$: 375.0, (M−1)$^−$: 373.0.

Cpd. 22

EM(calc.): 386.1; MS(ESI) m/e(M+1)$^+$: 387.1, (M−1)$^−$: 384.7.

Cpd. 23

EM(calc.): 374.1; MS(ESI) m/e(M+1)$^+$: 374.9, (M−1)$^−$: 372.9.

Cpd. 24

EM(calc.): 370.1; MS(ESI) m/e(M+1)$^+$: 370.8, (M−1)$^−$: 369.0.

Cpd. 25

EM(calc.): 370.1; MS(ESI) m/e(M+1)$^+$: 371.0, (M−1)$^−$: 369.1.

Cpd. 26

EM(calc.): 414.14; MS(ESI) m/e(M+1H)$^+$: 415.2, (M−1H)$^−$: 413.2.

Cpd. 27

EM(calc.): 469.18; MS(ESI) m/e(M+1H)$^+$: 470.1, (M−1H)$^−$: 468.4.

Cpd. 28

EM(calc.): 447.14; MS(ESI) m/e(M+1H)$^+$: 448.1, (M−1H)$^−$: 446.2.

Cpd. 29

EM(calc.): 354.1; MS(ESI) m/e(M+1)$^+$: 355.1, (M−1)$^−$: 353.1.

Cpd. 30

EM(calc.): 370.1; MS(ESI) m/e(M+1)$^+$: 371.0, (M−1)$^−$: 368.9.

Cpd. 31

EM(calc.): 400.1; MS(ESI) m/e(M+1H)$^+$: 401.0, (M−1H)$^−$: 399.2.

Cpd. 32

EM(calc.): 427.1; MS(ESI) m/e(M+1H)$^+$: 428.2, (M−1H)$^−$: 426.2.

Cpd. 33

EM(calc.): 414.1; MS(ESI) m/e(M+1H)$^+$: 415.4, (M−1H)$^−$: 413.2.

Cpd. 34

EM(calc.): 469.2; MS(ESI) m/e(M+1H)$^+$: 470.1, (M−1H)$^−$: 468.3.

Cpd. 35

EM(calc.): 447.1; MS(ESI) m/e(M+1H)$^+$: 448.2, (M−1H)$^−$: 446.5.

Cpd. 36

EM(calc.): 368.1; MS(ESI) m/e(M+1)$^+$: 369.0, (M−1)$^−$: 367.2.

Cpd. 37

$^1$H NMR(400MHz, DMSO-d$_6$) δ 11.69(s, 1H), 11.04(s, 1H), 8.77(t, J=5.6Hz, 1H), 7.70(d, J=8.4Hz, 2H), 7.39(m, 2H), 7.11(s, 1H), 7.05(m, 1H), 7.01(d, J=8.4Hz, 2H), 4.18(t, J=6.0Hz, 2H), 3.67(m, 2H). EM(calc.): 357.1; MS(ESI) m/e(M+1H)$^+$: 357.8, (M−1H)$^−$: 356.2.

Cpd. 38

$^1$H NMR(400MHz, DMSO-d$_6$) δ 11.42(s, 1H), 11.05(s, 1H), 8.66, (t, J=5.6Hz, 1H), 7.70(d, J=9.2Hz, 2H), 7.29(d, J=8.4Hz, 1H), 7.03(m, 4H), 6.81(m, 1H), 4.17(t, J=5.6Hz, 2H), 3.75(s, 3H), 3.66(m, 2H). EM(calc.): 369.1; MS(ESI) m/e(M+1H)$^+$: 369.9, (M−1H)$^−$: 368.2.

Cpd. 39

EM(calc.): 384.13; MS(ESI) m/e(M+1H)$^+$: 384.9, (M−1H)$^−$: 383.2.

Cpd. 40

EM(calc.): 446.15; MS(ESI) m/e(M+1H)$^+$: 447.2, (M−1H)$^−$: 445.4.

Cpd. 41

$^1$H NMR(400MHz, DMSO-d$_6$) δ 11.28(s, 1H), 11.04(s, 1H), 8.53(t, J=5.6Hz, 1H), 7.70(d, J=9.2Hz, 2H), 7.02(m, 4H), 6.86(s, 1H), 4.16(t, J=5.6Hz, 2H), 3.76(s, 3H), 3.75(s, 3H), 3.63(m, 2H). EM(calc.): 399.1; MS(ESI) m/e(M+1H)$^+$: 400.0, (M−1H)$^−$: 398.1.

Cpd. 42

$^1$H NMR(400MHz, DMSO-d$_6$) δ 11.09(bs, 1H), 10.60(bs, 1H), 9.29(t, J=6.0Hz, 1H), 8.08(d, J=8.0Hz, 1H), 7.70(m, 3H), 7.57(t, J=7.2Hz, 1H), 7.45(t, J=7.2Hz, 1H), 7.00(d, J=9.2Hz, 2H), 4.83(m, 2H), 4.23(t, J=6.0Hz, 2H), 3.94(m, 2H), 3.73(m, 4H), 3.44(m, 2H), 3.27(m, 2H). EM(calc.): 439.2; MS(ESI) m/e(M+1H)$^+$: 439.8, (M−1H)$^−$: 438.2.

Cpd. 44

EM(calc.): 412.16; MS(ESI) m/e(M+1H)$^+$: 413.1, (M−1H)$^−$: 411.3.

TABLE 3-continued

Cpd. 45

¹H NMR(400MHz, DMSO-d₆) δ 11.05(s, 1H), 8.92(t, J=5.2Hz, 1H), 7.74(d, J=7.6Hz, 1H), 7.70(d, J=8.8Hz, 2H), 7.59(s, 1H), 7.55(d, J=6.8Hz, 1H), 7.32(m, 3H), 7.06(d, J=7.6Hz, 2H), 7.00(d, J=9.2Hz, 2H), 6.95(t, J=7.2Hz, 1H), 5.44(s, 2H), 4.19(t, J=6.0Hz, 2H), 3.69(m, 2H). EM(calc.): 446.2; MS(ESI) m/e(M+1H)⁺: 447.2, (M−1H)⁻: 445.3.

Cpd. 46

¹H NMR(400MHz, DMSO-d₆) δ 11.08(s, 1H), 8.91(t, J=5.6Hz, 1H), 7.71(m, 3H), 7.58(s, 1H), 7.44(d, J=7.6Hz, 1H), 7.32(t, J=7.6Hz, 1H), 7.03(d, J=8.8Hz, 2H), 4.78(s, 2H), 4.20(t, J=6.0Hz, 2H), 3.69(m, 2H), 3.36(m, 3H). EM(calc.): 384.1; MS (ESI) m/e(M+1H)⁺: 385.9, (M−1H)⁻: 383.2.

Cpd. 47

¹H NMR(400MHz, DMSO-d₆) δ 11.33(s, 1H), 11.09(s, 1H), 9.32(t, J=5.6Hz, 1H), 7.88(d, J=8.4Hz, 1H), 7.71(m, 3H), 7.61(s, 1H), 7.43(t, J=7.6Hz, 1H), 7.03(d, J=8.8Hz, 2H), 4.68(s, 2H), 4.23(t, J=5.6Hz, 2H), 3.83(m, 6H), 3.37(m, 2H), 3.20(m, 2H). EM(calc.): 439.2; MS(ESI) m/e(M+1H)⁺: 440.2, (M−1H)⁻: 438.4.

Cpd. 48

¹H NMR(400MHz, DMSO-d₆) δ 11.09(s, 1H) 10.74(s, 1H), 9.31(t, J=5.6Hz, 1H), 7.88(d, J=8.0Hz, 1H), 7.72(d, J=8.6Hz, 2H), 7.65(d, J=7.2Hz, 1H), 7.62(s, 1H), 7.42(d, J=8.0Hz, 1H), 7.02(d, J=8.8Hz, 2H), 4.63(d, J=5.2Hz, 2H), 4.23(t, J=6.0Hz, 2H), 3.70(m, 2H), 2.78(s, 3H), 2.770(s, 3H). EM(calc.): 397.2; MS(ESI) m/e(M+1H)⁺: 398.0, (M−1H)⁻: 396.1.

Cpd. 49

EM(calc.): 384.1; MS(ESI) m/e(M−1)⁻: 382.9.

Cpd. 50

EM(calc.): 400.1; MS(ESI) m/e(M−1)⁻: 398.7.

Cpd. 51

¹H NMR(400MHz, DMSO-d₆) δ 11.07(s, 1H), 8.78(t, J=6.0Hz, 1H), 7.71(m, 3H), 7.54(s, 1H), 7.43(t, J=7.2Hz, 1H), 7.32(t, J=7.6Hz, 1H), 6.99(d, J=8.4Hz, 2H), 4.77(s, 2H), 4.10(t, J=6.0Hz, 2H), 3.47(m, 2H), 3.36(s, 3H), 2.02(m, 2H). EM(calc.): 398.2; MS(ESI) m/e(M+1H)⁺: 399.1, (M−1H)⁻: 397.1.

Cpd. 52

¹H NMR(400MHz, DMSO-d₆) δ 8.82(t, J=5.6Hz, 1H), 7.71(m, 3H), 7.54(m, 2H), 7.31(m, 3H), 7.06(d, J=8.0Hz, 2H), 6.95(m, 3H), 5.43(s, 2H), 4.09(t, J=6.0Hz, 2H), 3.47(m, 2H), 2.02(m, 2H). EM(calc.): 460.2; MS(ESI) m/e(M+1H)⁺: 461.0, (M−1H)⁻: 459.1.

Cpd. 53

EM(calc.): 428.16; MS(ESI) m/e(M+1H)⁺: 428.9, (M−1H)⁻: 427.1.

Cpd. 54

¹H NMR(DMSO-d₆): 2.11(3H, s); 2.78(1H, dd, 14.8Hz); 2.86(1H, dd, 14.5Hz); 4.17(1H, dd, 10.4Hz); 4.23(1H, dd, 10.6Hz); 4.49(1H, m); 7.00(2H, d, 9Hz); 7.32(1H, t, 7Hz); 7.46(1H, td, 8.1Hz); 7.56(1H, s); 7.64(1H, d, 8Hz); 7.70(2H, d, 9Hz); 7.77(1H, d, 8Hz); 8.77(1H, d, 8Hz); 8.88(1H, s). MS(M+1): 401.

Cpd. 55

¹H NMR(DMSO-d₆): 3.31(3H, s); 3.53(1H, dd, 13, 3.5Hz); 3.66(1H, dd, 13.8Hz); 4.16(1H, dd, 9.6Hz); 4.24(1H, dd, 9.8Hz); 4.87(1H, m); 7.00(2H, d, 9Hz); 7.33(1H, t, 7Hz); 7.47(1H, t, 8Hz); 7.57(1H, s); 7.65(1H, d, 8Hz); 7.70(2H, d, 9Hz); 7.77(1H, d, 8Hz); 8.89(1H, s); 9.0(1H, d, 8Hz). MS(M−1): 431.

Cpd. 56

¹H NMR(400MHz, DMSO-d₆) δ: 7.92(br s, 1H), 8.76(t, 1H, J=5.9Hz), 7.75(m, 3H), 7.60(d, 1H, J=7.6Hz), 7.48(t, 1H, J=8.0Hz), 7.32(t, 1H, J=8.0Hz), 7.27(m, 5H), 7.17(m, 1H), 7.04(m, 2H), 4.21(t, 2H, J=5.9Hz), 3.69(m, 2H) 3.39(m, 2H), 2.96(t, 2H, J=8.3Hz). EM(calc.): 444; MS(ESI) m/e(M+1H)⁺: 445.3, (M−1H)⁻: 443.3.

Cpd. 57

¹H NMR(400MHz, DMSO-d₆) δ 11.07(s, 1H), 9.38(s, 1H), 8.90(s, 1H), 7.94(d, J=8.0Hz, 1H), 7.57(m, 10H), 6.97(d, J=8.0Hz, 2H), 4.80(m, 2H), 4.20(s, 2H), 3.70(m, 2H), 3.31(m, 3H), 2.66(m, 2H). MS(ESI) m/e: (M+1H)⁺: 474.4, (M−1H)⁻: 472.1.

Cpd. 58

¹H NMR(400MHz, DMSO-d₆) δ 11.05(s, 1H), 9.73(m, 1H), 8.89(s, 1H), 7.75(d, J=8.0Hz, 2H), 7.70(d, J=8.0Hz, 2H), 7.61(d, J=8.0Hz, 1H), 7.43(t, 8.0Hz, 1H), 7.18(m, 6H), 6.98(d, J=8.0Hz, 2H), 4.13(t, J=8.0Hz, 2H), 3.95(m, 2H), 3.58(m, 2H), 2.78(m, 2H), 2.65(m, 2H), 1.24(s, 3H). MS(ESI) m/e: (M+1H)⁺: 487.9, (M−1H)⁻: 486.1.

Cpd. 59

¹H NMR(400MHz, DMSO-d₆) δ 11.04(s, 1H), 8.88(s, 1H), 8.84(t, J=8.0Hz, 1H), 7.82(d, J=8.0Hz, 1H), 7.70(d, J=8.0Hz, 2H), 7.59(d, J=8.0Hz, 1H), 7.48(t, J=8.0Hz, 1H), 7.34(t, J=8.0Hz, 1H), 7.00(d, J=8.0Hz, 2H), 4.31(s, 2H), 4.18(t, J=8.0Hz, 2H), 3.66(m, 2H), 3.38(m, 2H), 2.45(t, J=8.0Hz, 2H), 1.65(m, 2H). MS(ESI) m/e: (M+1H)⁺: 445.2, (M−1H)⁻: 443.1.

Cpd. 60

¹H NMR(400MHz, DMSO-d₆) δ 11.05(s, 1H), 9.04(t, J=8.0Hz, 1H), 7.86(d, J=8.0Hz, 1H), 7.70(d, J=8.0Hz, 2H), 7.63(d, J=8.0Hz, 1H), 7.50(t, J=8.0Hz, 1H), 7.36(t, J=8.0Hz, 1H), 7.00(d, J=8.0Hz, 2H), 4.57(m, 2H), 4.18(t, J=8.0Hz, 2H), 3.65(m, 2H), 3.46(t, J=8.0Hz, 2H), 2.77(m, 2H), 1.80(m, 2H). MS(ESI) m/e: (M+1H)⁺: 461.0, (M−1H)⁻: 459.1.

Cpd. 61

¹H NMR(400MHz, DMSO-d₆) δ 11.04(s, 1H), 9.05(t, J=8.0Hz, 1H), 7.87(d, J=8.0Hz, 1H), 7.70(d, J=8.0Hz, 2H), 7.64(d, J=8.0Hz, 1H), 7.51(t, J=8.0Hz, 1H), 7.38(t, J=8.0Hz, 1H), 7.00(d, J=8.0Hz, 2H), 5.11(s, 2H), 4.19(t, J=8.0Hz, 2H), 3.68(m, 2H), 3.44(t, J=8.0Hz, 2H), 3.13(m, 2H), 1.83(m, 2H). MS(ESI) m/e: (M+1H)⁺: 477.0, (M−1H)⁻: 475.0.

Cpd. 62

MS(ESI) m/e: (M+1H)⁺: 527.6, (M−1H)⁻: 525.5.

Cpd. 63

¹H NMR(400MHz, DMSO-d₆) δ: 11.04(s, 1H), 8.88(br s, 1H), 8.73(t, 1H, J=5.9Hz), 7.75-7.69(m, 3H), 7.57-7.42(m, 6H), 7.28(t, 1H, J=7.7Hz), 7.00(d, 2H, J=8.7Hz), 4.17(t, 2H, J=5.9Hz), 3.65(q, 2H, J=5.9Hz) 3.40(t, 2H, J=6.9Hz), 3.04(t, 2H, J=6.9Hz). EM(calc.): 512; MS(ESI) m/e(M+1H)⁺: 513.3, (M−1H)⁻: 511.2.

Cpd. 64

¹H NMR(400MHz, DMSO-d₆) δ: 11.04(s, 1H), 8.87(br s, 1H), 8.83(t, 1H, J=5.9Hz), 7.70(m, 3H), 7.55(d, 1H, J=8.3Hz), 7.43(t, 1H, J=7.4Hz), 7.34(t, 1H, J=8.0Hz), 7.28-7.20(m, 3H), 7.11(d, 1H, 8.0Hz), 7.00(d, 2H, J=8.6Hz), 4.17(t, 2H, J=5.9Hz), 3.65(q, 2H, J=5.9Hz) 3.38(t, 2H, J=8.3Hz), 3.00(t, 2H, J=8.3Hz). EM(calc.): 528; MS(ESI) m/e(M+1H)⁺: 529.4, (M−1H)⁻: 527.5.

Cpd. 65

¹H NMR(400MHz, DMSO-d₆) δ 11.06(s, 1H), 10.93(s, 1H), 9.32(m, 2H), 9.23(s, 1H), 8.89(s, 1H), 7.96(d, J=8.0Hz, 1H), 7.70(m, 3H), 7.56(t, J=8.0Hz, 1H), 7.44(t, J=8.0Hz, 1H), 7.00(d, J=8.0Hz, 2H), 4.64(s, 2H), 4.23(t, J=8.0Hz, 2H), 3.71(m, 4H). MS(ESI) m/e: (M+1H)⁺: 443.4, (M−1H)⁻: 441.4.

Cpd. 66

¹H NMR(400MHz, DMSO-d₆) δ 11.06(s, 1H), 9.33(t, J=8.0Hz, 1H), 8.89(s, 1H), 8.00(d, J=8.0Hz, 1H), 7.71(m, 3H), 7.56(t, J=8.0Hz, 1H), 7.43(t, J=8.0Hz, 3H), 7.00(d, J=8.0Hz, 2H), 4.60(s, 2H), 4.23(t, J=8.0Hz, 2H), 3.71(m, 2H), 3.20(t, J=8.0Hz, 2H), 2.72(t, J=8.0Hz, 2H). MS(ESI) m/e: (M+1H)⁺: 442.3, (M−1H)⁻: 440.1.

Cpd. 67

¹H NMR(400MHz, DMSO-d₆) δ: , 9.11(t, 1H, J=6.0Hz), 7.82(d,, 1H, J=7.7Hz), 7.76(d, 2H, J=8.5Hz), 7.69(d, 1H, J=8.5Hz), 7.62(s, 1H), 7.51(t, 1H, J=8.5Hz), 7.40-7.30(m, 3H), 7.21(d, 2H, J=8.5Hz), 7.00-6.97(m, 3H), 4.99(m, 1H), 4.35(m, 1H), 4.27(m, 1H), 3.78(m, 1H), 3.70(m, 1H). EM(calc.): 446.15; MS(ESI) m/e(M+1H)⁺: 447.4, (M−1H)⁻: 445.3.

Cpd. 68

¹H NMR(400MHz, DMSO-d₆) δ 11.04(s, 1H), 8.86(J=4.0Hz, 1H), 7.83(d, J=8.0Hz, 1H), 7.70(d, J=8.0Hz, 2H), 7.61(d, J=8.0Hz, 1H), 7.47(t, J=8.0Hz, 1H), 7.33(t, J=4.0Hz, 1H), 7.00(d, J=8.0Hz, 2H), 5.02(s, 2H), 4.18(t, J=8.0Hz, 2H), 3.65(m, 2H), 3.52(t, J=8.0Hz, 2H), 3.44(t, J=8.0Hz, 2H), 1.68(m, 2H). MS(ESI) m/e: (M+1H)⁺: 429.1, (M−1H)⁻: 426.9.

Cpd. 69

¹H NMR(400MHz, DMSO-d₆) δ: 11.04(s, 1H), 9.03(t, 1H, J=5.9Hz), 7.86(d, 1H, J=9.2Hz), 7.70(d, 2H, J=8.3Hz), 7.63(d, 1H, J=8.3Hz), 7.49(t,

TABLE 3-continued

1H, J=8.8Hz), 7.36(t, 1H, J=7.0Hz), 7.29(t, 1H, J=8.8Hz), 7.18(m, 1H), 7.07(t, 1H, J=7.0Hz), 7.00(d, 1H, J=8.3Hz), 6.91(m, 1H), 5.78(s, 2H), 4.20(t, 2H, J=5.9Hz), 3.68(q, 2H, J=5.9Hz). EM(calc.): 464; MS(ESI) m/e(M+1H)$^+$: 465.1, (M−1H)$^−$: 463.1.
Cpd. 70

$^1$H NMR(400MHz, DMSO-d$_6$) δ: 11.04(s, 1H), 9.04(t, 1H, J=5.9Hz), 9.00(br s, 1H), 7.84(d, 1H, J=7.3Hz), 7.70(d, 2H, J=9.2Hz), 7.63(d, 1H, J=8.1Hz), 7.49(t, 1H, J=8.6Hz), 7.35(t, 1H, J=7.7Hz), 7.27(m, 1H), 7.18(m, 1H), 7.00(d, 1H, J=9.2Hz), 6.95(m, 1H), 6.87(m, 1H), 6.74(m, 1H), 5.71(s, 2H), 4.21(t, 2H, J=5.9Hz), 3.69(q, 2H, J=5.9Hz). EM(calc.): 464; MS(ESI) m/e(M+1H)$^+$: 465.0, (M−1H)$^−$: 463.1.
Cpd. 71

$^1$H NMR(400MHz, DMSO-d$_6$) δ: 11.04(s, 1H), 9.00(t, 1H, J=5.9Hz), 7.84(d, 1H, J=8.4Hz), 7.70(d, 2H, J=9.2Hz), 7.62(d, 1H, J=8.8Hz), 7.48(t, 1H, J=8.4Hz), 7.34(t, 1H, J=7.3Hz), 7.10-7.00(m, 6H), 5.67(s, 2H), 4.20(t, 2H, J=5.9Hz), 3.68(q, 2H, J=5.9Hz). EM(calc.): 464; MS(ESI) m/e(M+1H)$^+$: 464.9, (M−1H)$^−$: 463.0.
Cpd. 72

$^1$H NMR(400MHz, DMSO-d$_6$) δ 11.04(s, 1H), 8.88(m, 2H), 7.86(d, J=8.0Hz, 1H), 7.70(d, J=8.0Hz, 2H), 7.61(d, J=8.0Hz, 1H), 7.47(t, J=8.0Hz, 1H), 7.33(t, J=4.0Hz, 1H), 7.00(d, J=8.0Hz, 2H), 5.05(s, 2H), 4.19(t, J=8.0Hz, 2H), 3.65(m, 2H), 3.59(m, 2H), 3.47(m, 2H), 3.23(s, 3H). MS(ESI) m/e: (M+1H)$^+$: 428.9, (M−1H)$^−$: 426.9.
Cpd. 73

$^1$H NMR(400MHz, DMSO-d$_6$) δ 11.05(s, 1H), 9.20(t, J=4.0Hz, 1H), 8.83(d, J=8.0Hz, 2H), 7.86(d, J=8.0Hz, 1H), 7.71(d, J=8.0Hz, 2H), 7.66(d, J=8.0Hz, 1H), 7.51(t, J=8.0Hz, 1H), 7.38(t, J=8.0Hz, 1H), 7.25(d, J=8.0Hz, 2H), 6.98(d, J=8.0Hz, 2H), 6.07(s, 2H), 4.21(t, J=8.0Hz, 2H), 3.70(m, 2H). MS(ESI) m/e: (M+1H)$^+$: 448.0, (M−1H)$^−$: 446.4.
Cpd. 74

$^1$H NMR(400MHz, DMSO-d$_6$) δ: 8.86(m, 1H), 8.81(br s, 1H), 7.80(d, 1H, J=8.2Hz), 7.63(d, 2H, J=9.4Hz), 7.57(d, 1H, J=8.2Hz), 7.44(t, 1H, J=7.8Hz), 7.32(t, 1H, J=7.0Hz), 7.12(t, 1H, J=9.0Hz), 6.91(m, 1H, J=8.6Hz), 5.64(s, 2H), 4.06(t, 2H, J=6.0Hz), 3.54(t, 2H, J=6.0Hz). EM(calc.): 500.13; MS(ESI) m/e(M+1H)$^+$: 501.5, (M−1H)$^−$: 499.3.
Cpd. 75

$^1$H NMR(400MHz, DMSO-d$_6$) δ 11.04(s, 1H), 9.14(t, J=4.0Hz, 1H), 7.89(m, 1H), 7.70(m, 3H), 7.61(d, J=8.0Hz, 1H), 7.46(m, 1H), 7.40(m, 1H), 7.29(t, J=4.0Hz, 1H), 7.02(d, J=8.0Hz, 2H), 6.43(d, J=8.0Hz, 1H), 6.23(d, J=4.0Hz, 1H), 5.62(s, 2H), 4.23(t, J=4.0Hz, 2H), 3.72(m, 2H). MS(ESI) m/e: (M+1H)$^+$: 448.2, (M−1H)$^−$: 446.4.
Cpd. 76

$^1$H NMR(400MHz, DMSO-d$_6$) δ 11.04(s, 1H), 8.96(t, J=4.0Hz, 1H), 8.88(s, 1H), 7.82(d, J=8.0Hz, 1H), 7.70(d, J=8.0Hz, 2H), 7.63(d, J=8.0Hz, 1H), 7.50(t, J=8.0Hz, 1H), 7.36(t, J=8.0Hz, 1H), 7.00(d, J=8.0Hz, 2H), 5.24(s, 2H), 4.18(m, 4H), 3.66(m, 2H). MS(ESI) m/e: (M+1H)$^+$: 453.3, (M−1H)$^−$: 451.1.
Cpd. 77

$^1$H NMR(400MHz, DMSO-d$_6$) δ 11.05(s, 1H), 9.04(t, J=4.0Hz, 1H), 8.89(s, 1H), 8.09(s, 1H), 7.87(d, J=8.0Hz, 1H), 7.70(d, J=8.0Hz, 2H), 7.63(d, J=8.0Hz, 1H), 7.89(m, 1H), 7.50(m, 3H), 7.35(t, J=8.0Hz, 1H), 7.17(d, J=8.0Hz, 2H), 7.03(m, 3H), 5.77(s, 2H), 4.22(t, J=8.0Hz, 2H), 3.70(m, 2H). MS(ESI) m/e: (M+1H)$^+$: 513.1, (M−1H)$^−$: 511.1.
Cpd. 78

$^1$H NMR(400MHz, DMSO-d$_6$) δ: 9.05(s, 1H), 8.97(t, 1H, J=5.9Hz), 8.81(s, 1H), 8.08(s, 1H), 7.80(d, 1H, J=7.6Hz), 7.66-7.62(m, 4H), 7.56(d, 1H, J=8.6Hz), 7.42(t, 1H, J=8.1Hz), 7.28(t, 1H, J=7.6Hz), 7.15(m, 2H), 6.94(d, 2H, J=8.6Hz), 5.70(s, 2H), 4.15(t, 2H, J=5.9Hz), 3.64(t, 2H, J=5.9Hz). EM(calc.): 513.16; MS(ESI) m/e(M+1H)$^+$: 514.2, (M−1H)$^−$: 512.2.
Cpd. 79

$^1$H NMR(400MHz, DMSO-d$_6$) δ 11.08(s, 1H), 10.33(s, 1H), 9.25(t, J=4.0Hz, 1H), 8.11(d, J=8.0Hz, 1H), 7.70(m, 3H), 7.53(d, J=8.0Hz, 1H), 7.44(t, J=8.0Hz, 1H), 6.99(d, J=8.0Hz, 2H), 4.84(d, J=4.0Hz, 2H), 4.23(t, J=8.0Hz, 2H), 3.70(m, 2H), 3.48(m, 2H), 3.23(m, 2H), 2.04(m, 2H), 1.90(m, 2H). MS(ESI) m/e: (M+1H)$^+$: 424.1, (M−1H)$^−$: 422.3.
Cpd. 80

$^1$H NMR(400MHz, DMSO-d$_6$) δ 11.06(s, 1H), 9.87(s, 1H), 9.29(t, J=4.0Hz, 1H), 8.03(d, J=8.0Hz, 1H), 7.71(m, 3H), 7.57(t, J=8.0Hz, 1H), 7.45(t, J=8.0Hz, 1H), 6.99(d, J=8.0Hz, 2H), 4.77(s, 2H), 4.23(t, J=8.0Hz, 2H), 3.70(m, 2H), 3.48(m, 2H), 3.04(m, 2H), 1.73(m, 5H), 1.38(m, 1H). MS(ESI) m/e: (M+1H)$^+$: 438.0, (M−1H)$^−$: 436.3.
Cpd. 81

$^1$H NMR(400MHz, DMSO-d$_6$) δ 11.05(s, 1H), 9.55(t, J=4.0Hz, 1H), 8.89(s, 1H), 7.89(d, J=8.0Hz, 1H), 7.70(d, J=8.0Hz, 2H), 7.61(d, J=8.0Hz, 1H), 7.45(t, J=8.0Hz, 1H), 7.33(t, J=8.0Hz, 1H), 6.99(d, J=8.0Hz, 2H), 4.19(t, J=8.0Hz, 2H), 3.96(s, 2H), 3.68(m, 2H), 2.95(m, 2H), 2.28(m, 1H), 2.09(m, 2H), 1.78(m, 2H), 1.44(m, 2H). MS(ESI) m/e: (M+1H)$^+$: 506.1, (M−1H)$^−$: 504.2.
Cpd. 82

$^1$H NMR(400MHz, DMSO-d$_6$) δ 11.07(s, 1H), 9.18(s, 1H), 8.04(s, 1H), 7.70(m, 3H), 7.53(t, J=8.0Hz, 1H), 7.39(t, J=8.0Hz, 1H), 7.00(d, J=8.0Hz, 2H), 4.21(t, J=8.0Hz, 2H), 3.70(m, 12H), 2.76(s, 3H). MS(ESI) m/e: (M+1H)$^+$: 453.0, (M−1H)$^−$: 451.1.
Cpd. 83

$^1$H NMR(400MHz, DMSO-d$_6$) δ 11.05(s, 1H), 8.90(m, 2H), 7.83(d, J=8.0Hz, 1H), 7.70(d, J=8.0Hz, 2H), 7.61(d, J=8.0Hz, 1H), 7.48(t, J=8.0Hz, 1H), 7.34(t, J=8.0Hz, 1H), 7.00(d, J=8.0Hz, 2H), 5.08(s, 2H), 4.19(t, J=8.0Hz, 2H), 3.68(m, 4H), 2.58(m, 2H). MS(ESI) m/e: (M+1H)$^+$: 467.0, (M−1H)$^−$: 465.1.
Cpd. 84

$^1$H NMR(400MHz, DMSO-d$_6$) δ: 11.07(s, 1H), 8.91(m, 2H), 7.73(d, 2H, J=9.0Hz), 7.66(s, 1H), 7.47(d, 1H, J=8.7Hz), 7.37(t, 1H, J=8.4Hz), 7.15(d, 1H, J=7.4Hz), 7.04(d, 2H, J=9.0Hz), 4.21(t, 1H, J=5.7Hz), 3.69(t, 2H, J=5.7Hz), 3.36(s, 3H). EM(calc.): 354.12; MS(ESI) m/e(M+1H)$^+$: 354.7, (M−1H)$^−$: 353.1.
Cpd. 85

$^1$H NMR(400MHz, DMSO-d$_6$) δ 11.05(s, 1H), 8.88(s, 1H), 8.80(t, J=8.0Hz, 1H), 7.76(d, J=8.0Hz, 1H), 7.71(d, J=8.0Hz, 2H), 7.57(d, J=8.0Hz, 1H), 7.46(t, J=8.0Hz, 1H), 7.32(m, 3H), 7.03(m, 4H), 4.76(s, 2H), 4.15(t, J=8.0Hz, 2H), 3.62(m, 2H). MS(ESI) m/e: (M+1H)$^+$: 481.1, (M−1H)$^−$: 479.0.
Cpd. 86

$^1$H NMR(400MHz, DMSO-d$_6$) δ 11.05(s, 1H), 8.88(m, 2H), 7.71(d, J=8.0Hz, 2H), 7.55(m, 4H), 7.46(t, J=8.0Hz, 1H), 7.28(m, 3H), 7.00(d, J=8.0Hz, 2H), 4.77(s, 2H), 4.15(t, J=8.0Hz, 2H), 3.60(m, 2H). MS(ESI) m/e: (M+1H)$^+$: 497.3, (M−1H)$^−$: 495.1.
Cpd. 87

$^1$H NMR(400MHz, DMSO-d$_6$) δ 11.05(s, 1H), 8.89(s, 1H), 8.82(t, J=8.0Hz, 1H), 7.74(d, J=8.0Hz, 1H), 7.71(d, J=8.0Hz, 2H), 7.63(m, 3H), 7.50(t, J=8.0Hz, 1H), 7.34(m, 3H), 7.00(d, J=8.0Hz, 2H), 5.32(s, 2H), 4.06(t, J=8.0Hz, 2H), 3.49(m, 2H). MS(ESI) m/e: (M+1H)$^+$: 513.2, (M−1H)$^−$: 511.2.
Cpd. 88

$^1$H NMR(400MHz, DMSO-d$_6$) δ 11.03(s, 1H), 8.88(s, 1H), 8.68(d, J=8.0Hz, 1H), 7.81(d, J=8.0Hz, 1H), 7.69(d, J=8.0Hz, 2H), 7.64(d, J=8.0Hz, 1H), 7.50(t, J=8.0Hz, 1H), 7.36(t, J=8.0Hz, 1H), 6.98(d, J=8.0Hz, 2H), 5.25(s, 2H), 4.18(m, 5H), 1.72(m, 2H), 0.94(t, J=8.0Hz, 3H). MS(ESI) m/e: (M+1H)$^+$: 481.2, (M−1H)$^−$: 479.2.
Cpd. 89

$^1$H NMR(400MHz, DMSO-d$_6$) δ: 11.94(s, 1H), 11.04(m, 1H), 9.36(m, 1H), 8.88(br s, 1H), 8.63(s, 1H), 7.71(d, 2H, J=8.5Hz), 7.22(t, 1H, J=8.1Hz), 7.07(dd, 1H, J=8.1, 1.7Hz), 7.02(d, 2H, J=8.5Hz), 6.65(dd, 1H, J=7.6, 1.6Hz), 4.21(t, 2H, J=5.6Hz), 3.73(2H, q, J=5.2Hz). EM(calc.): 356; MS(ESI) m/e(M+1H)$^+$: 357.2, (M−1H)$^−$: 354.9.
Cpd. 90

$^1$H NMR(400MHz, DMSO-d$_6$) δ: 11.03(s, 1H), 8.69(d, 1H, J=8.3Hz), 7.86(d, 1H, J=2.1Hz), 7.69(m, 3H), 7.54(s, 1H), 7.47(dd, 1H, J=8.5Hz, 2.5Hz), 6.98(d, 2H, J=8.6Hz), 4.24(m, 1H), 4.13(m, 1H), 4.06(m, 1H), 1.75(m, 1H), 1.62(m, 1H), 0.93(t, 3H, J=7.3Hz). EM(calc.): 402; MS(ESI) m/e(M+1H)$^+$: 403.0, (M−1H)$^−$: 400.9.
Cpd. 91

$^1$H NMR(400MHz, DMSO-d$_6$) δ: 11.02(s, 1H), 9.00(t, 1H, J=5.8Hz), 7.85(d, 1H, J=1.9Hz), 7.68(m, 3H), 7.52(s, 1H), 7.46(dd, 1H, J=8.5Hz, 1.9Hz), 7.03(d, 2H, J=8.5Hz), 4.69(m, 1H), 3.57(m, 1H), 3.40(m, 1H), 1.32(d, 3H, J=5.9Hz). EM(calc.): 388; MS(ESI) m/e(M+1H)$^+$: 389.1, (M−1H)$^−$: 387.0.

TABLE 3-continued

Cpd. 92

$^1$H NMR(400MHz, DMSO-d$_6$) δ: 11.05(br s, 1H), 8.96(t, 1H, J=5.6Hz), 8.80(d, 1H, J=2.0Hz), 8.75(dd, 1H, J=5.6, 0.8Hz), 8.35, (d, 1H, J=8.0Hz), 7.87(dd, 1H, J=7.6, 5.6Hz), 7.71(m, 3H), 7.61(d, 1H, J=8.0Hz), 7.45(t, 1H, J=6.8Hz), 7.34(d, 1H, J=7.2Hz), 7.00(m, 2H), 4.91(s, 2H), 4.75(s, 2H), 4.18(t, 2H, J=5.6Hz), 3.66(q, 2H, J=6.0Hz). EM(calc.): 461; MS(ESI) m/e(M+1H)$^+$: 462.2, (M−1H)$^-$: 460.3.

Cpd. 93

$^1$H NMR(400MHz, DMSO-d$_6$) δ: 11.00(s, 1H), 8.82(m, 1H), 8.37(s, 1H), 7.67(dd, 2H, J=6.8, 1.6Hz), 7.32-7.24(m, 2H), 7.01(d, 2H, J=9.6Hz), 6.90(d, 1H, J=8.0Hz), 4.17(t, 2H, J=5.2Hz), 3.89(s, 3H), 3.69(m, 2H). EM(calc.): 370; MS(ESI) m/e(M+1H)$^+$: 371.2, (M−1H)$^-$: 369.1.

Cpd. 94

$^1$H NMR(400MHz, DMSO-d$_6$) δ: 11.04(s, 1H), 8.96(t, 1H, J=5.6Hz), 8.45(s, 1H), 7.70(d, 2H, J=8.4Hz), 7.37-7.30(m, 2H), 7.02(d, 2H, J=8.4Hz), 6.98(dd, 1H, J=7.6, 0.8Hz), 4.37(m, 2H), 4.17(t, 2H, J=5.6Hz), 3.82(m, 2H), 3.69(q, 2H, J=6.0Hz), 3.34(s, 3H). EM(calc.): 414; MS(ESI) m/e(M+1H)$^+$: 415.2, (M−1H)$^-$: 413.3.

Cpd. 95

$^1$H NMR(400MHz, DMSO-d$_6$) δ: 11.04(br s, 1H), 8.86(m, 1H), 8.65(t, 1H, 5.6Hz), 8.61(dd, 1H, J=4.8, 1.6Hz), 8.37(s, 1H), 8.13(m, 1H), 7.67(m, 2H), 7.54(m, 1H), 7.38-7.31(m, 2H), 7.07(dd, 1H, J=7.6, 0.8Hz), 6.88(m, 2H), 5.40(s, 2H), 3.91(t, 2H, J=6.0Hz), 3.40(m, 2H). EM(calc.): 447; MS(ESI) m/e(M+1H)$^+$: 448.2, (M−1H)$^-$: 446.1.

Cpd. 96

$^1$H NMR(400MHz, DMSO-d$_6$) δ: 11.57(s, 1H), 8.65(t, 1H, J=4.5Hz), 7.69(d, 2H, J=8.5Hz), 7.20(s, 1H), 7.09-6.98(m, 4H), 6.48(d, 1H, J=7.9Hz), 4.17(m, 2H), 3.85(s, 3H), 3.65(m, 2H). EM(calc.): 369; MS(ESI) m/e(M+1H)$^+$: 370.1, (M−1H)$^-$: 368.2.

Cpd. 97

$^1$H NMR(400MHz, DMSO-d$_6$) δ: 11.06(s, 1H), 8.62(d, 1H, J=8.7Hz), 7.88(d, 1H, J=7.6Hz), 7.72(d, 2H, J=8.5Hz), 7.65(d, 1H, J=8.5Hz), 7.50(t, 1H, J=8.5Hz), 7.36(t, 1H, J=8.5Hz), 7.02(d, 2H, J=8.5Hz), 5.08(s, 2H), 4.29(m, 1H), 4.18(m, 1H), 4.10(m, 1H), 3.62(m, 2H), 3.51(m, 2H), 3.26(s, 3H), 1.77(m, 1H), 1.67(m, 1H), 0.97(t, 3H, J=7.3Hz). EM(calc.): 456; MS(ESI) m/e(M+1H)$^+$: 457.1, (M−1H)$^-$: 455.2.

Cpd. 98

$^1$H NMR(400MHz, DMSO-d$_6$) δ: 11.05(s, 1H), 8.91(t, 1H, J=6.1Hz), 7.88(d, 1H, J=7.5Hz), 7.72(d, 2H, J=8.4Hz), 7.63(d, 1H, J=8.4Hz), 7.50(t, 1H, J=8.5Hz), 7.36(t, 1H, J=8.5Hz), 7.07(d, 2H, J=8.4Hz), 5.07(s, 2H), 4.74(q, 1H, J=6.0Hz), 3.60(m, 2H), 3.50(m, 2H), 3.45(m, 2H), 3.26(s, 3H), 1.32(d, 3H, J=6.1Hz). EM(calc.): 442; MS(ESI) m/e(M+1H)$^+$: 443.1, (M−1H)$^-$: 441.5.

Cpd. 99

$^1$H NMR(400MHz, DMSO-d$_6$) δ: 11.09(s, 1H), 9.54(s, 1H), 9.40(t, 1H, J=5.6Hz), 8.04(d, 1H, J=7.8Hz), 7.74(d, 2H, J=8.3Hz), 7.61(t, 1H, J=7.3Hz), 7.49(t, 1H, J=7.3Hz), 7.03(d, 2H, J=8.5Hz), 4.82(s, 2H), 4.26(t, 2H, J=5.6Hz), 3.75(q, 2H, J=5.6Hz), 3.50(m, 2H), 3.25(m, 4H), 1.32(t, 6H, J=7.4Hz). EM(calc.): 425; MS(ESI) m/e (M+1H)$^+$: 426.1, (M−1H)$^-$: 424.2.

Cpd. 109

$^1$H NMR(DMSO-d$_6$): 1.95(2H, m); 2.05(3H, s); 2.48-2.62(2H, m); 4.08(1H, dd, 11.6Hz); 4.16(1h, dd, 11.7Hz); 4.45(1H, m); 6.99(2H, d, 9Hz); 7.32(1H, t, 7Hz); 7.45(1H, td, 8.1Hz); 7.55(1H, d, 1Hz); 7.64(1H, d, 8Hz); 7.69(2H, d, 9Hz); 7.76(1H, d, 8Hz); 8.7(1H, d, 8Hz); 8.87(1H, s). MS(M+1): 415.

Cpd. 110

$^1$H NMR(DMSO-d$_6$): 2.03-2.21(2H, m); 2.99(1H, s, 3H); 3.22(2H, t, 7Hz); 4.12(1H, dd, 11.6Hz); 4.19(1h, dd, 11.7Hz); 4.46(1H, m); 7.00(2H, d, 9Hz); 7.33(1H, t, 7Hz); 7.46(1H, td, 8.1Hz); 7.57(1H, d, 1Hz); 7.64(1H, d, 8Hz); 7.70(2H, d, 9Hz); 7.77(1H, d, 8Hz); 8.79(1H, d, 8Hz); 8.88(1H, s). MS(M+1): 447.

TABLE 4

Cpd. 1

EM(calc.): 381.13; MS(ESI) m/e(M+1H)$^+$: 382.3, (M−1H)$^-$: 380.2.

Cpd. 2

EM(calc.): 395.15; MS(ESI) m/e(M+1H)$^+$: 396.1, (M−1H)$^-$: 394.2.

Cpd. 3

EM(calc.): 331.08; MS(ESI) m/e(M+1H)$^+$: 331.7, (M−1H)$^-$: 330.1.

Cpd. 4

EM(calc.): 317.10; MS(ESI) m/e(M+1H)$^+$: 318.10, (M−1H)$^-$: 315.9.

Cpd. 5

EM(calc.): 425.2; MS(ESI) m/e(M+1)$^+$: 426.1, (M−1)$^-$: 424.1.

Cpd. 6

EM(calc.): 381.1; MS(ESI) m/e(M+1)$^+$: 382.0, (M−1)$^-$: 380.1.

Cpd. 7

EM(calc.): 381.1; MS(ESI) m/e(M+1)$^+$: 382.0, (M−1)$^-$: 380.2.

Cpd. 8

EM(calc.): 341.1; MS(ESI) m/e(M+1)$^+$: 341.9, (M−1)$^-$: 340.1.

Cpd. 9

EM(calc.): 381.1; MS(ESI) m/e(M+1)$^+$: 381.8, (M−1)$^-$: 380.0.

Cpd. 10

EM(calc.): 411.1; MS(ESI) m/e(M+1)$^+$: 412.0, (M−1)$^-$: 410.3.

Cpd. 11

EM(calc.): 395.2; MS(ESI) m/e(M+1)$^+$: 396.0, (M−1)$^-$: 394.2.

Cpd. 12

EM(calc.): 388.1; MS(ESI) m/e(M+1)$^+$: 389.1, (M−1)$^-$: 387.0.

Cpd. 13

EM(calc.): 355.12; MS(ESI) m/e(M+1)$^+$: 355.9, (M−1)$^-$: 354.1.

Cpd. 14

EM(calc.): 355.1; MS(ESI) m/e(M+1)$^+$: 355.9, (M−1)$^-$: 353.8.

Cpd. 15

EM(calc.): 409.2; MS(ESI) m/e(M+1)$^+$: 410.2, (M−1)$^-$: 408.3.

Cpd. 16

EM(calc.): 341.1; MS(ESI) m/e(M+1)$^+$: 341.8, (M−1)$^-$: 340.2.

Cpd. 17

$^1$H NMR(400MHz, DMSO-d$_6$) δ 11.64(s, 1H), 8.66(d, J=8.0Hz, 1H), 7.76(d, J=8.0Hz, 1H), 7.64(d, J=8.0Hz, 1H), 7.55(s, 1H), 7.46(t, J=8.4Hz, 1H), 7.32(t, J=8.0Hz, 1H), 6.72(s, 1H), 4.30(m, 3H), 1.67(m, 2H), 0.92(t, J=7.2Hz, 3H). EM(calc.): 359.1; MS(ESI) m/e: (M+1H)$^+$: 359.8, (M−1H)$^-$: 358.1.

Cpd. 18

$^1$H NMR(400MHz, DMSO-d$_6$) δ 11.64(s, 1H), 9.48(s, 1H), 8.47(d, J=8.0Hz, 1H), 8.09(m, 1H), 7.82(m, 2H), 7.71(m, 2H), 7.55(t, J=8.0Hz, 1H), 7.49(m, 2H), 7.39(m, 1H), 4.30(m, 3H), 1.69(m, 2H), 0.94(t, J=7.2Hz, 3H). EM(calc.): 395.2; MS(ESI) m/e: (M+1H)$^+$: 395.8, (M−1H)$^-$: 394.0.

Cpd. 19

$^1$H NMR(400MHz, DMSO-d$_6$) δ 11.63(s, 1H), 8.93(d, J=5.6Hz, 1H), 7.75(d, J=7.6Hz, 1H), 7.63(d, J=7.6Hz, 1H), 7.54(s, 1H), 7.45(t, J=7.6Hz, 1H), 7.32(t, J=7.6Hz, 1H), 6.72(s, 1H), 4.90(m, 1H), 3.56(m, 2H), 0.35(d, J=7.2Hz, 3H). EM(calc.): 345.1; MS(ESI) m/e: (M+1H)$^+$: 345.8, (M−1H)$^-$: 344.0.

Cpd. 20

$^1$H NMR(400MHz, DMSO-d$_6$) δ 11.64(s, 1H), 9.480(s, 1H), 8.83(t, J=5.6Hz, 1H), 7.07(m, 1H), 7.80(d, J=7.6Hz, 1H), 7.70(d, J=7.6Hz, 1H), 7.53(t, J=7.6Hz, 1H), 7.48(m, 2H), 7.39(m, 1H), 6.72(s, 1H), 4.91(m, 1H), 3.58(m, 2H), 1.36(d, J=7.0Hz, 3H). EM(calc.): 381.1; MS(ESI) m/e: (M+1H)$^+$: 382.0, (M−1H)$^-$: 380.0.

TABLE 4-continued

Cpd. 21

EM(calc.): 367.1; MS(ESI) m/e(M+1)⁺: 367.8, (M−1)⁻: 366.2.

Cpd. 22

EM(calc.): 367.12; MS(ESI) m/e(M+1H)⁺: 368.0, (M−1H)⁻: 366.1.

Cpd. 23

EM(calc.): 374.0; MS(ESI) m/e(M+1)⁺: 374.7, (M−1)⁻: 372.9.

Cpd. 24

EM(calc.): 395.2; MS(ESI) m/e(M+1)⁺: 396.1.(M−1)⁻: 394.1

Cpd. 25

EM(calc.): 367.1; MS(ESI) m/e(M+1)⁺: 368.1, (M−1)⁻: 366.2.

Cpd. 26

EM(calc.): 381.1; MS(ESI) m/e(M+1)⁺: 382.0, (M−1)⁻: 380.1.

Cpd. 27

$^1$H NMR(400MHz, DMSO-d$_6$) δ 11.62(s, 1H), 9.45(s, 1H), 8.54(d, J= 7.6Hz, 1H), 8.43(s, 1H), 7.97(m, 4H), 7.60(m, 2H), 6.73(s, 1H), 4.33(m, 3H), 1.70(m, 2H), 0.96(t, J=7.6Hz, 3H). EM(calc.): 369.1; MS(ESI) m/e: (M+1H)⁺: 369.9, (M−1H)⁻: 368.0.

Cpd. 28

$^1$H NMR(400MHz, DMSO-d$_6$) δ 11.66(s, 1H), 9.50(s, 1H), 8.53(d, J= 7.6Hz, 1H), 8.11(m, 1H), 7.96(m, 2H), 7.55(m, 4H), 6.78(s, 1H), 4.33(m, 3H), 1.68(m, 2H), 1.01(t, J=7.2Hz, 3H). EM(calc.): 369.1; MS(ESI) m/e: (M+1H)⁺: 370.0, (M−1H)⁻: 368.2.

Cpd. 29

$^1$H NMR(400MHz, DMSO-d$_6$) δ 11.64(s, 1H), 8.86(t, J=5.6Hz, 1H), 8.40(s, 1H), 7.90(m, 4H), 7.59(m, 2H), 6.73(s, 1H), 4.94(m, 1H), 3.60(m, 2H), 1.38(d, J=6.0Hz, 3H). EM(calc.): 355.1; MS(ESI) m/e: (M+1H)⁺: 355.9, (M−1H)⁻: 353.9.

Cpd. 30

$^1$H NMR(400MHz, DMSO-d$_6$) δ 11.66(s, 1H), 8.78(t, J=5.6Hz, 1H), 8.09(d, J=7.6Hz, 1H), 7.96(m, 2H), 7.50(m, 4H), 6.74(s, 1H), 4.97(m, 1H), 3.61(m, 2H), 1.41(d, J=6.4Hz, 3H). EM(calc.): 355.1; MS(ESI) m/e: (M+1H)⁺: 356.1, (M−1H)⁻: 353.9.

Cpd. 31

EM(calc.): 345.1; MS(ESI) m/e(M+1)⁺: 345.8, (M−1)⁻: 344.0.

Cpd. 32

EM(calc.): 331.1; MS(ESI) m/e(M+1)⁺: 331.9, (M−1)⁻: 330.2.

Cpd. 33

EM(calc.): 437.12; MS(ESI) m/e(M+1H)⁺: 438.0, (M−1H)⁻: 436.2.

Example 4

Synthesis of acetyl-Gly-Ala-(N-acetyl-Lys)-AMC tert-Boc (N-Acetyl-Lys)-AMC (445 mg, 1 mmol, purchased from Bachem) was dissolved in 4 M HCL in dioxane to provide H-(N-acetyl-Lys)-AMC as a white solid. To a solution of H—(N-acetyl-Lys)-AMC in DMF (5 ml) was added Ac-Gly-Ala-OH (188 mg, 1 mmol) using PyBOP (520 mg, 1 mmol), HOBt (135 mg, 1 mmol), and NMM (0.296 ml, 2 mmol). The reaction mixture was stirred for 1 h and monitored by MS/LC for the presence of H—(N-acetyl-Lys)-AMC. Additional amounts of PyBOP (260 mg, 0.5 mmol), HOBt (70 mg, 0.5 mmol), and NMM (0.146 ml, 1 mmol) was added and the stirring was continued for additional 4 h after which the product was isolated in quantitative yield.

Biological Examples

Example 1

Inhibition of HDAC in Vitro

The HDAC inhibitory activity of the compounds of this invention in vitro was determined as follows.

Measurements were performed in a reaction volume of 100 µL using 96-well assay plates. HDAC-1 (200 pM final concentration) in reaction buffer (50 mM HEPES, 100 mM KCl, 0.001% Tween-20, 5% DMSO, pH 7.4) was mixed with inhibitor at various concentrations and allowed to incubate for 30 minutes, after which trypsin and acetyl-Gly-Ala-(N-acetyl-Lys)-AMC were added to final concentrations of 50 nM and 25 µM, respectively, to initiate the reaction. Negative control reactions were performed in the absence of inhibitor in replicates of eight.

The reactions were monitored in a fluorescence plate reader. After a 30 minute lag time, the fluorescence was measured over a 30 minute time frame using an excitation wavelength of 355 nm and a detection wavelength of 460 nm. The increase in fluorescence with time was used as the measure of the reaction rate. Inhibition constants were obtained using the program BatchKi (Kuzmic et al. *Anal. Biochem.* 2000, 286, 45-50). Most of the compounds of this invention had a Ki of <40 nm.

Example 2

Cell Proliferation Assay in Vitro

The ability of the compounds of Formula (I) to inhibit growth of tumor cells in vitro was determined as follows.

Stock cultures of the HCT116 colon carcinoma cell line were maintained in RPMI medium 1640 containing 10% (v/v) fetal bovine serum, 2 mM L-glutamine, 1 mM sodium pyruvate, 50 units/ml penicillin, and 50 µg/ml streptomycin at 37° C. in 5% $CO_2$ humidified atmosphere. Cells were cultured in 75-cm² culture flasks and subcultures were established every 3 to 4 days so as not to allow the cells to exceed 90% confluence.

HCT116 cells were harvested for proliferation assays by trypsinization (0.05% trypsin/0.53 mM EDTA), washed twice in culture medium, re-suspended in appropriate volume of medium, and then counted using a hemacytometer. Cells were seeded in wells of flat-bottom 96-well plates at a density of 5,000 cell/well in 100 µl. Cells were allowed to attach for 1.5 to 2 hours at 37° C.

Compounds were diluted from 10 mM stock solutions in DMSO. Serial 3-fold dilutions were performed in medium containing 0.6% DMSO in wells (in triplicate) of a 96-well U-bottom plates starting with a 60 µM solution. After dilutions were completed, 100 µl of each compound dilution (in triplicate) was transferred to designated triplicate wells of the 96-well plate containing cells in 100 µl of medium. Final concentrations of the dose-response for compounds in assay plates ranged from 0.12 to 30 µM. Control wells (cells with no treatment) received 100 µl of 0.6% DMSO in culture medium. Wells containing medium with no cells served as the background wells. Cells were cultured with the compounds for 48 and 72 hours at 37° C. in a humidified $CO_2$ incubator.

Cell proliferation was assessed by measuring fluorescence after the addition of the fluorogenic redox indicator, Alamar Blue™ (BioSource International). Ten μl of Alamar Blue™ was added to each well of the 96-well plate(s) 3 to 4 hours prior to the end of the incubation period. Assay plates were read in a fluorescence plate reader (excitation, 530 nM; emission, 620 nM). $G_{ISO}$ values (concentration at which the growth of the tumor cells was inhibited by 50%) for compounds were determined by plotting the percent control fluorescence against the logarithm of the compound concentration. The compounds of this invention inhibited the growth of the tumor cells.

Pharmaceutical Composition Examples

The following are representative pharmaceutical formulations containing a compound of Formula (I)

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 1.2 g |
| lactate buffer solution, 0.1 M | 10.0 ml |
| HCl (1 N) or NaOH (1 N) | q.s. to suitable pH |
| saline (optional) | q.s. to suitable osmolarity |
| water (distilled, sterile) | q.s. to 20 ml |

Compound (1.2 g) is combined with 0.1 M lactate buffer (10 ml) and gently mixed. Sonication can be applied for several minutes if necessary to achieve a solution. Appropriate amount of acid or base is added q.s. to suitable pH (preferable pH 4). A sufficient amount of water is then added q.s. to 20 ml.

Suppository Formulation

A suppository of total weight 2.5 g is prepared by mixing the compound of the invention with Witepsol™ H-15 (triglycerides of saturated vegetable fatty acid; Riches-Nelson, Inc., New York), and has the following composition:

| | |
| --- | --- |
| compound of the invention | 500 mg |
| Witepsol ™ H-15 | balance |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

We claim:

1. A compound of Formula (II):

Formula (II)

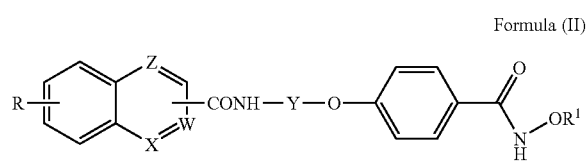

wherein X is C, CH or N;
W is C, CH or N;
Z is C, CH or N; wherein at least one of X, W, or Z is N;
$R^1$ is hydrogen or alkyl;
Y is alkylene optionally substituted with cycloalkyl, optionally substituted phenyl, alkylthio, alkylsulfinyl, alkylsulfonyl, optionally substituted phenylalkylthio, optionally substituted phenylalkylsulfonyl, hydroxyl, or optionally substituted phenoxy;

R is one or two optional substituents independently selected from alkyl, halo, haloalkyl, alkoxy, alkoxyalkyl, hydroxyalkoxy, hydroxyalkoxyalkyl, alkoxyalkyloxy, alkoxyalkyloxyalkyl, aminoalkyl, aminoalkoxy, haloalkoxy, haloalkoxyalkyl, optionally substituted phenyl, optionally substituted phenoxy, optionally substituted phenylalkyloxy, optionally substituted phenylalkyl, optionally substituted phenyloxyalkyl, optionally substituted heteroaryl, optionally substituted heteroaralkyloxy, optionally substituted heteroaryloxyalkyl, optionally substituted heterocycloalkylalkyl, optionally substituted heterocycloalkyloxy, optionally substituted heterocycloalkylalkyloxy, -alkylene-S(O)$_n$R$^a$, wherein n is 0 to 2 and R$^a$ is hydroxyalkyl or optionally substituted phenyl, -alkylene-NR$^e$-alkylene CONR$^c$R$^d$, wherein R$^c$ is hydroxyl and R$^d$ and R$^e$ are independently hydrogen or alkyl, or carboxyalkylaminoalkyl; and wherein

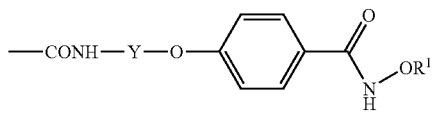

is bonded to any carbon atom on the aryl ring;

or a pharmaceutically acceptable salt thereof.

2. The compound of claim 1, wherein X is N, W is CH, and Z is CH.

3. The compound of claim 1, wherein X is CH, W is CH, and Z is N.

4. The compound of claim 1, wherein X is CH, W is N, and Z is CH.

5. The compound of claim 1, wherein X is N, W is CH, and Z is N.

6. The compound of claim 1, wherein Y is —CH$_2$CH$_2$—.

7. The compound of claim 2, wherein the quinoline group is monosubstituted.

8. The compound of claim 3, wherein the quinoline group is monosubstituted.

9. The compound of claim 4, wherein the isoquinoline group is monosubstituted.

10. The compound of claim 5, wherein the quinoxaline group is monosubstituted.

11. The compound of claim 7, wherein the substituent is N,N-dimethylaminomethyl, N,N-diethylaminomethyl, 2-fluorophenoxymethyl, 3-fluorophenoxymethyl, 4-fluorophenoxymethyl, hydroxyl-4-yloxymethyl, 2,4,6-trifluorophenoxy-methyl, 2-oxopyridin-1-ylmethyl, 2,2,2-trifluorethoxy-methyl, 4-imidazol-1-ylphenoxy-methyl, 4-[1.2.4]-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenyl)ethyl, N-methyl-N-benzylaminomethyl, N-methyl-N-2-phenylethylaminomethyl, 3-hydroxypropyl-thiomethyl, 3-hydroxypropylsulfinylmethyl, 3-hydroxypropylsulfonylmethyl, N-methyl-N-2-indol-3-ylethylaminomethyl, 2-(4-trifluoromethylphenyl)ethyl, N-hydroxyaminocarbonyl-methylaminomethyl, or 2-carboxyethylaminomethyl.

12. The compound of claim 8, wherein the substituent is N,N-dimethylaminomethyl, N,N-diethylaminomethyl, 2-fluorophenoxymethyl, 3-fluorophenoxymethyl, 4-fluorophenoxymethyl, hydroxyl-4-yloxymethyl, 2,4,6-trifluorophenoxy-methyl, 2-oxopyridin-1-ylmethyl, 2,2,2-trifluorethoxy-methyl, 4-imidazol-1-ylphenoxy-methyl, 4-[1.2.4]-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenyl)ethyl, N-methyl-N-benzylaminomethyl, N-methyl-N-2-phenylethylaminomethyl, 3-hydroxypropyl-thiomethyl, 3-hydroxypropylsulfinylmethyl, 3-hydroxypropylsulfonylmethyl, N-methyl-N-2-indol-3-ylethylaminomethyl, 2-(4-trifluoromethylphenyl)ethyl, N-hydroxyaminocarbonyl-methylaminomethyl, or 2-carboxyethylaminomethyl.

13. The compound of claim 9, wherein the substituent is N,N-dimethylaminomethyl, N,N-diethylaminomethyl, 2-fluorophenoxymethyl, 3-fluorophenoxymethyl, 4-fluorophenoxymethyl, hydroxyl-4-yloxymethyl, 2,4,6-trifluorophenoxy-methyl, 2-oxopyridin-1-ylmethyl, 2,2,2-trifluorethoxy-methyl, 4-imidazol-1-ylphenoxy-methyl, 4-[1.2.4]-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenyl)ethyl, N-methyl-N-benzylaminomethyl, N-methyl-N-2-phenylethylaminomethyl, 3-hydroxypropyl-thiomethyl, 3-hydroxypropylsulfinylmethyl, 3-hydroxypropylsulfonylmethyl, N-methyl-N-2-indol-3-ylethylaminomethyl, 2-(4-trifluoromethylphenyl)ethyl, N-hydroxyaminocarbonyl-methylaminomethyl, or 2-carboxyethylaminomethyl.

14. The compound of claim 10, wherein the substituent is N,N-dimethylaminomethyl, N,N-diethylaminomethyl, 2-fluorophenoxymethyl, 3-fluorophenoxymethyl, 4-fluorophenoxymethyl, hydroxyl-4-yloxymethyl, 2,4,6-trifluorophenoxy-methyl, 2-oxopyridin-1-ylmethyl, 2,2,2-trifluorethoxy-methyl, 4-imidazol-1-ylphenoxy-methyl, 4-[1.2.4]-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenyl)ethyl, N-methyl-N-benzylaminomethyl, N-methyl-N-2-phenylethylaminomethyl, 3-hydroxypropyl-thiomethyl, 3-hydroxypropylsulfinylmethyl, 3-hydroxypropylsulfonylmethyl, N-methyl-N-2-indol-3-ylethylaminomethyl, 2-(4-trifluoromethylphenyl)ethyl, N-hydroxyaminocarbonyl-methylaminomethyl, or 2-carboxyethylaminomethyl.

15. A pharmaceutical composition comprising a therapeutically effective amount of a compound of claim 1 or pharmaceutically acceptable salts thereof and a pharmaceutically acceptable excipient.

* * * * *